(12) United States Patent
Brucker et al.

(10) Patent No.: US 10,022,183 B2
(45) Date of Patent: Jul. 17, 2018

(54) TEMPERATURE-RESPONSIVE IRRIGATED ABLATION ELECTRODE WITH REDUCED COOLANT FLOW AND RELATED METHODS FOR MAKING AND USING

(71) Applicants: Gregory G. Brucker, Minneapolis, MN (US); Steven D. Savage, Paynesville, MN (US)

(72) Inventors: Gregory G. Brucker, Minneapolis, MN (US); Steven D. Savage, Paynesville, MN (US)

(73) Assignee: Innovations in Medicine, LLC, Minnetonka, MN (US)

( * ) Notice: Subject to any disclaimer, the term of this patent is extended or adjusted under 35 U.S.C. 154(b) by 561 days.

(21) Appl. No.: 14/676,789

(22) Filed: Apr. 1, 2015

(65) Prior Publication Data
US 2015/0272669 A1 Oct. 1, 2015

Related U.S. Application Data

(60) Provisional application No. 61/973,839, filed on Apr. 1, 2014.

(51) Int. Cl.
| | |
|---|---|
| *A61B 18/12* | (2006.01) |
| *A61B 18/14* | (2006.01) |
| *A61B 18/00* | (2006.01) |

(52) U.S. Cl.
CPC . *A61B 18/1492* (2013.01); *A61B 2018/00011* (2013.01); *A61B 2018/00029* (2013.01);
(Continued)

(58) Field of Classification Search
CPC ...... A61B 18/1492; A61B 2018/00011; A61B 2018/00029; A61B 2018/00712; A61B 2018/00791
See application file for complete search history.

(56) References Cited

U.S. PATENT DOCUMENTS

| | | | |
|---|---|---|---|
| 4,953,559 A | * | 9/1990 | Salerno .................. A61B 5/042 600/564 |
| 5,334,193 A | | 8/1994 | Nardella |
| | | (Continued) | |

FOREIGN PATENT DOCUMENTS

| | | |
|---|---|---|
| EP | 2062545 A2 | 5/2009 |
| EP | 2380519 A1 | 10/2011 |

OTHER PUBLICATIONS

Polyimide properties from www.goodfellow.com as of Nov. 15, 2008 as disclosed by the Internet Arcive at web.archive.org. Accessed on Sep. 14, 2017.*
(Continued)

*Primary Examiner* — Daniel Fowler
(74) *Attorney, Agent, or Firm* — Charles A. Lemaire; Jonathan M. Rixen; Lemaire Patent Law Firm, P.L.L.C.

(57) ABSTRACT

The present invention provides an irrigated ablation electrode that includes a plurality of high L/d interior fluid passageways and/or slit-shaped apertures to provide for a lower rate of fluid flow and a more uniform distribution of fluid over an exterior surface of the electrode and reduce propensity for aperture blockage. In some embodiments, the slit-shaped apertures have an aspect ratio of at least three, at least five, at least ten, or at least fifteen. Some embodiments include maintaining a pressure drop of at least 345 pascals between irrigation fluid inside the irrigated ablation electrode and fluid immediately outside the electrode when the irrigation fluid has a flow rate of no more than five milliliters per minute (5 ml/min). Some embodiments include a low-density insert with a plurality of fluid channels on its exterior surface to more efficiently cool the electrode and provide a faster thermal response.

20 Claims, 31 Drawing Sheets

(52) U.S. Cl.
CPC ............... *A61B 2018/00714* (2013.01); *A61B 2018/00791* (2013.01)

(56) References Cited

U.S. PATENT DOCUMENTS

| | | | |
|---|---|---|---|
| 5,348,554 | A | 9/1994 | Imran et al. |
| 5,540,681 | A * | 7/1996 | Strul .................. A61B 18/1206 606/1 |
| 5,688,267 | A | 11/1997 | Panescu et al. |
| 5,735,846 | A | 4/1998 | Panescu et al. |
| 5,800,428 | A | 9/1998 | Nelson et al. |
| 5,810,804 | A * | 9/1998 | Gough ............... A61B 18/1477 604/22 |
| 5,913,854 | A | 6/1999 | Shearon et al. |
| 5,919,188 | A | 7/1999 | Shearon et al. |
| 6,015,407 | A | 1/2000 | Rieb et al. |
| 6,017,338 | A | 1/2000 | Brucker et al. |
| 6,032,077 | A | 2/2000 | Pomeranz |
| 6,063,081 | A | 5/2000 | Mulier et al. |
| 6,080,151 | A | 6/2000 | Swartz et al. |
| 6,315,777 | B1 | 11/2001 | Comben |
| 6,405,078 | B1 * | 6/2002 | Moaddeb ................. A61N 1/06 604/113 |
| 6,488,680 | B1 | 12/2002 | Francischelli et al. |
| 6,522,930 | B1 | 2/2003 | Schaer et al. |
| 7,104,989 | B2 | 9/2006 | Skarda |
| 7,156,843 | B2 | 1/2007 | Skarda |
| 7,163,537 | B2 | 1/2007 | Lee et al. |
| 7,235,070 | B2 | 6/2007 | Vanney |
| 7,435,250 | B2 | 10/2008 | Francischelli et al. |
| 7,776,034 | B2 | 8/2010 | Kampa |
| 7,815,635 | B2 | 10/2010 | Wittkampf et al. |
| 7,819,866 | B2 | 10/2010 | Bednarek |
| 7,819,868 | B2 | 10/2010 | Cao et al. |
| 7,879,030 | B2 | 2/2011 | Paul et al. |
| 7,959,628 | B2 | 6/2011 | Schaer et al. |
| 8,187,267 | B2 | 5/2012 | Pappone et al. |
| 8,394,093 | B2 | 3/2013 | Wang et al. |
| 8,449,539 | B2 | 5/2013 | Wang et al. |
| 8,702,697 | B2 | 4/2014 | Curley |
| 8,920,415 | B2 | 12/2014 | Govari |
| 9,510,894 | B2 | 12/2016 | Clark et al. |
| 2003/0144656 | A1 * | 7/2003 | Ocel ..................... A61B 5/042 606/41 |
| 2004/0143257 | A1 * | 7/2004 | Fuimaono .......... A61B 18/1482 606/41 |
| 2008/0161800 | A1 * | 7/2008 | Wang ................. A61B 18/1492 606/41 |
| 2009/0005768 | A1 * | 1/2009 | Sharareh ............ A61B 18/1492 606/17 |
| 2010/0057072 | A1 | 3/2010 | Roman et al. |
| 2010/0057074 | A1 * | 3/2010 | Roman ............... A61B 18/1492 606/33 |
| 2011/0009856 | A1 | 1/2011 | Jorgensen et al. |
| 2011/0264089 | A1 * | 10/2011 | Zirkle .................... A61B 5/042 606/41 |
| 2011/0270244 | A1 | 11/2011 | Clark et al. |
| 2011/0282342 | A1 | 11/2011 | Leo et al. |
| 2011/0288392 | A1 | 11/2011 | de la Rama et al. |
| 2013/0172873 | A1 | 7/2013 | Govari et al. |
| 2013/0267779 | A1 * | 10/2013 | Woolford ........... A61B 1/00039 600/156 |
| 2014/0187893 | A1 | 7/2014 | Clark et al. |

OTHER PUBLICATIONS

Nakagawa, Hiroshi, "Comparison of 12 and 56 Hole Electrodes for Open Irrigated Radiofrequency Ablation in a Canine Thigh Muscle Preparation: Improvement in Thrombus Reduction with 56 Small Irrigation Holes", "downloadable from internet: http://bsw.envisiongrouptest.com/docs/Nakagawa.pdf", 2010, Publisher: Biosense Webster, Inc.

European Patent Office, "EPO Supplementary Search Report/Written Opinion for related application EP 15772821.3, dated Mar. 10, 2017, 8 pages."

"PCT Search Report/Written Opinion for related PCT/US2015/023955 application, dated Aug. 27, 2015, 12 pages."

Shah, D, "ThermoCool SF Catheter provides 'uniform cooling' with a reduced volume load. Case Report: anti-arrhythmic drug resistant atrial fibrillation ablation in a chronic end-stage renal failure patient", "downloaded from internet: www.biosensewebster.com/docs/Shah.pdf? ", 2011, Publisher: Biosense Webster, Inc.

"PCT International Preliminary Report on Patentability for related PCT/US2015/023955 application, dated May 3, 2016."

* cited by examiner

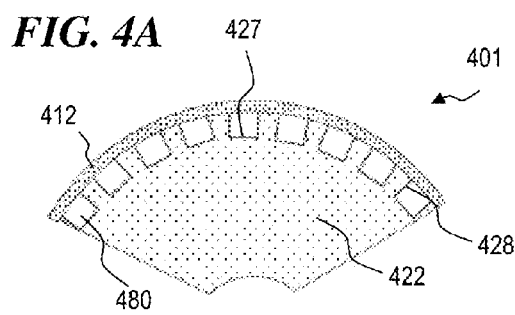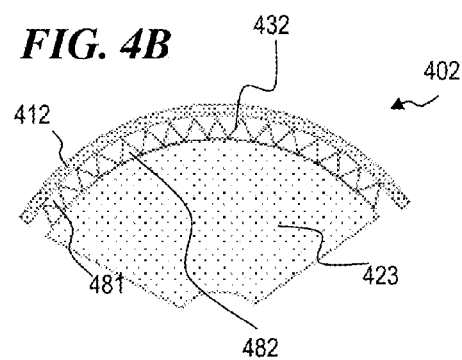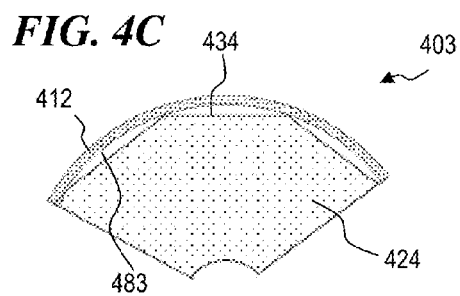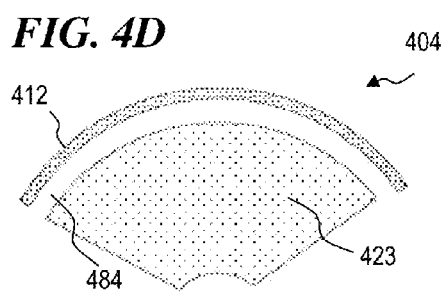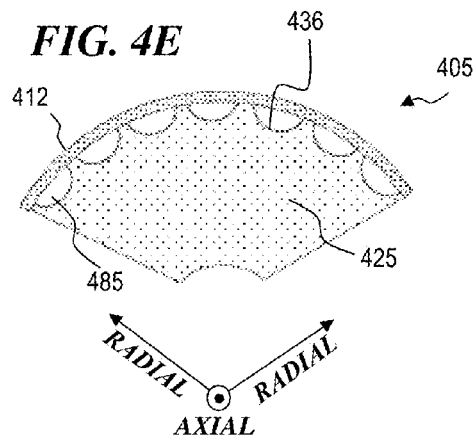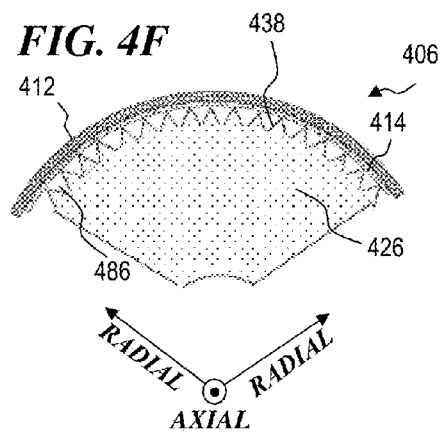

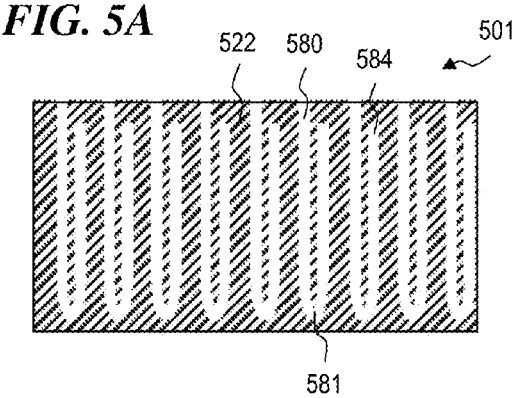
FIG. 5A
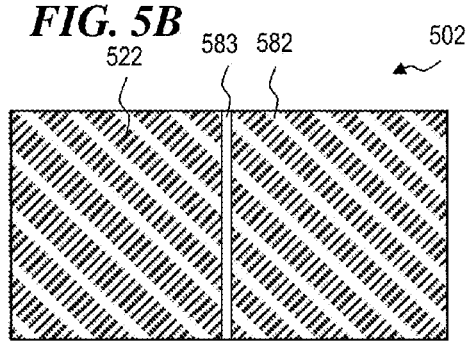
FIG. 5B
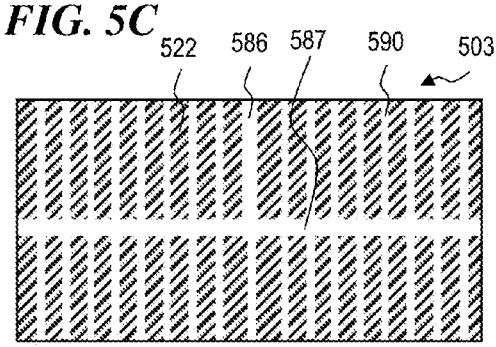
FIG. 5C
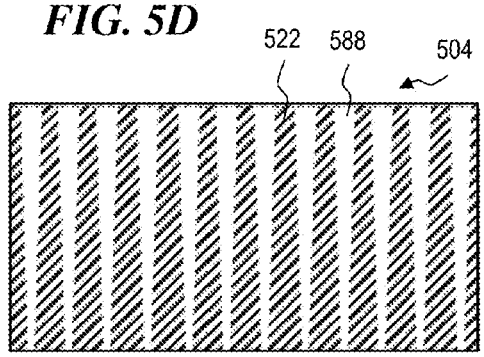
FIG. 5D
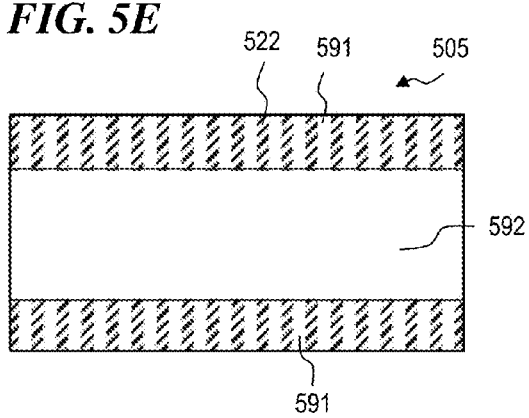
FIG. 5E
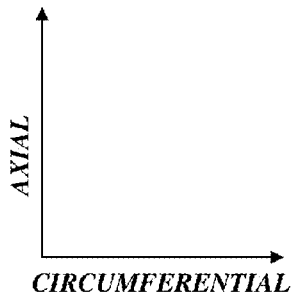

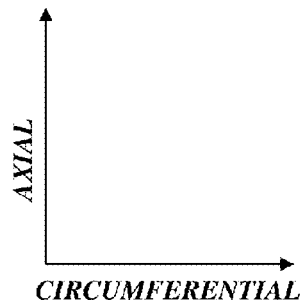

*FIG. 11A*  *FIG. 11B*
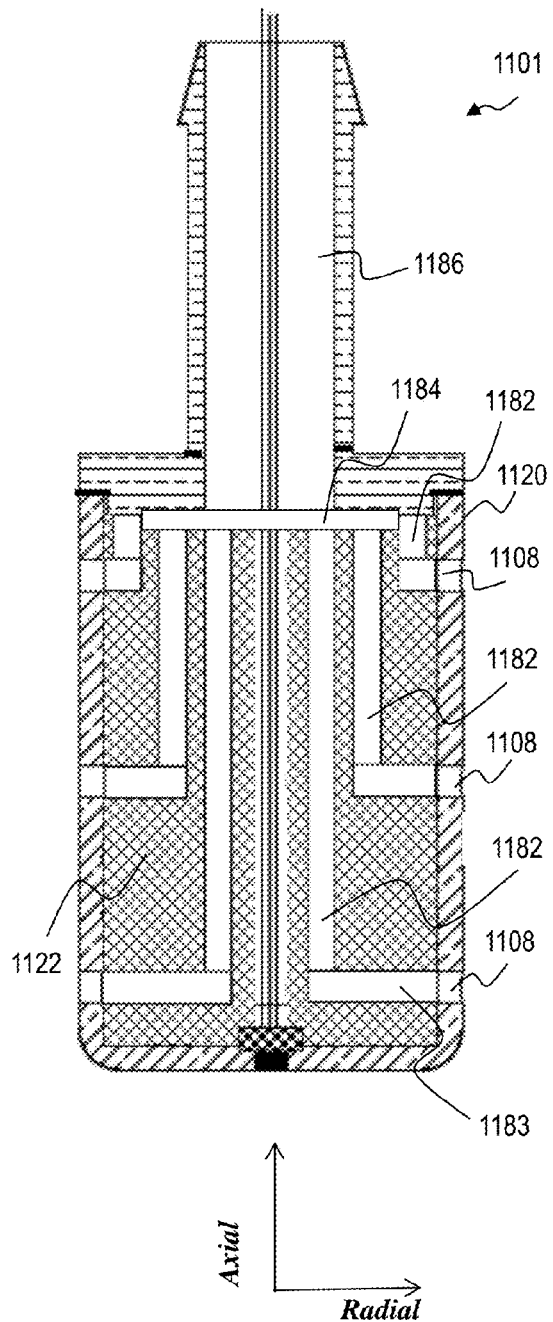
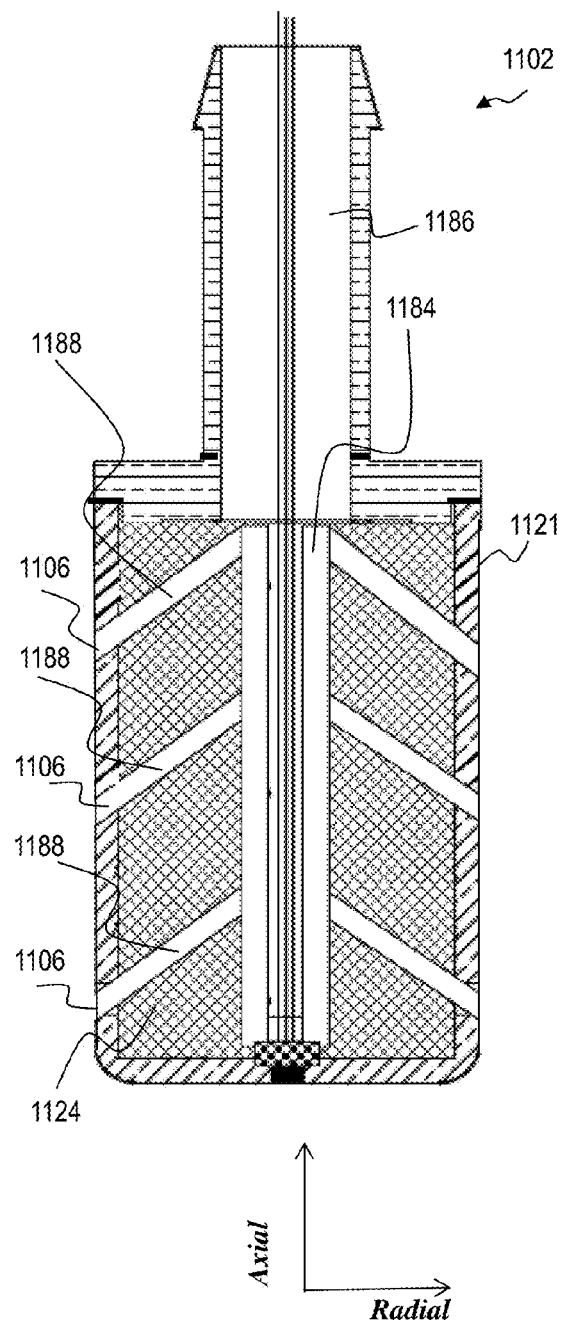

L

W

*CROSS-SECTIONAL VIEWS OF VARIOUS SLIT TYPES THROUGH THE ELECTRODE SHELL WALL*

2308

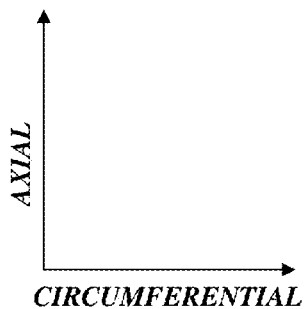
AXIAL
CIRCUMFERENTIAL

FIG. 27A
FIG. 27B
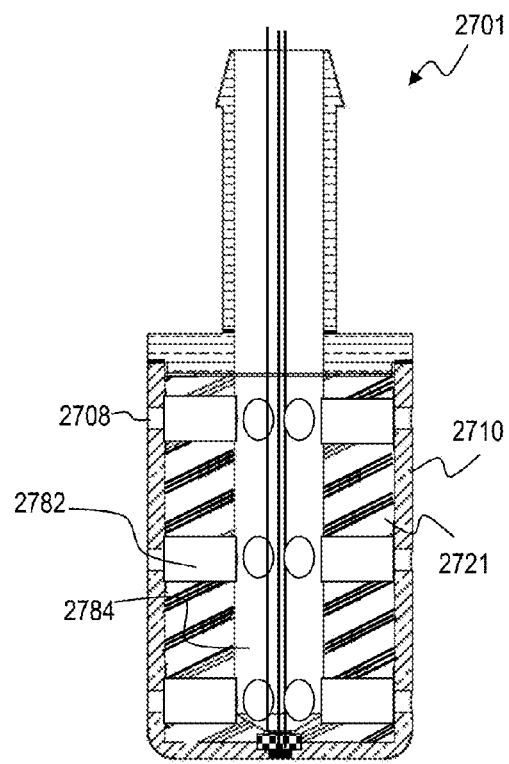
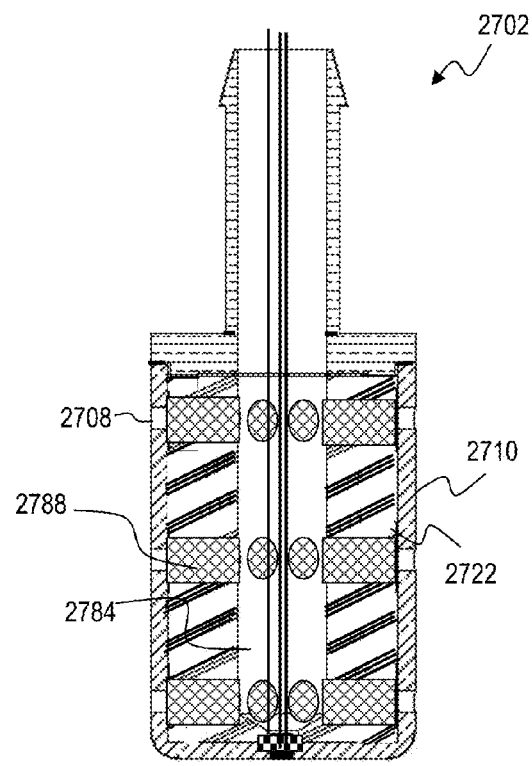

TEMPERATURE-RESPONSIVE IRRIGATED ABLATION ELECTRODE WITH REDUCED COOLANT FLOW AND RELATED METHODS FOR MAKING AND USING

RELATED APPLICATION

This invention claims priority benefit under 35 U.S.C. § 119(e) of U.S. Provisional Patent Application No. 61/973,839 filed Apr. 1, 2014 by Gregory G. Brucker et al., titled "Temperature Responsive Irrigated Ablation Electrode with Reduced Coolant Flow and related methods for making and using," which is incorporated herein by reference in its entirety.

FIELD OF THE INVENTION

This invention relates to the field of cardiac-procedure devices and methods, and more specifically to a method and apparatus for more efficiently controlling temperature of an ablation tip of a cardiac-procedure catheter, and, in particular, a temperature-responsive irrigated ablation electrode with reduced coolant flow and improved particle accommodation.

BACKGROUND OF THE INVENTION

There are numerous patents and journal articles that relate to the field of cardiac-procedure devices and methods, and more specifically to irrigated cardiac-procedure catheters that use radio-frequency (RF) energy delivered through a tip electrode.

U.S. Pat. No. 5,334,193 issued to Nardella on Aug. 2, 1994 with the title "Fluid cooled ablation catheter" and is incorporated herein in its entirety by reference. This patent describes a thin, elongate and flexible ablation catheter, suitable for delivery to an internal organ, which includes a fluid delivery lumen centrally located within the catheter, and first and second electrodes disposed on an outer surface of the catheter. The electrodes preferably are helically oriented about the catheter. At least one of the electrodes is in communication with a source of electrosurgical energy so as to deliver ablative electrosurgical energy to tissue. The lumen communicates with a fluid supply source such that fluid is conveyed through the lumen and is discharged to adjacent tissue during the delivery of ablative energy. The fluid delivered through the lumen assists in optimizing the electrode temperature. A method and apparatus is also provided to regulate the fluid flow rate based on monitored electrode temperature and/or tissue impedance.

U.S. Pat. No. 5,348,554 issued to Imran et al. on Sep. 20, 1994, and U.S. Pat. No. 5,423,811 issued to Imran et al. on Jun. 13, 1995 both with the title "Method for RF ablation using cooled electrode" and both are incorporated herein in its entirety by reference. Imran et al. describe a catheter for radio frequency ablation with a cooled electrode for use in tissue having a surface that includes an elongate member having proximal and distal extremities. A metal conducting electrode secured to the distal extremity of the elongate member and having a chamber therein. A conductor extends through the elongate member from the proximal to the distal extremity for supplying radio frequency energy to the electrode. The elongate member has a lumen in the distal extremity which is in communication with the chamber. A coolant is disposed in the chamber and in contact with the electrode for dissipating heat created in the electrode by the application of radio frequency energy thereto.

U.S. Pat. No. 5,688,267 issued to Panescu et al. on Nov. 18, 1997 with the title "Systems and methods for sensing multiple temperature conditions during tissue ablation" and is incorporated herein by reference in its entirety. This patent describes systems and methods for ablating body tissue use an electrode for contacting tissue to form a tissue-electrode interface. The electrode is adapted to be connected to a source of ablation energy to conduct ablation energy for transmission by the electrode into tissue at the tissue-electrode interface. The electrode is preferably cooled. The systems and methods include multiple temperature sensing elements. One element senses tissue temperature. A second element senses electrode temperature. A third element senses the rate at which the electrode is cooled. The systems and methods control the supply of ablation energy to the electrode based, at least in part, upon the multiple temperatures sensed by the different temperature sensing elements.

U.S. Pat. No. 5,735,846 issued to Panescu et al. on Apr. 7, 1998 with the title "Systems and methods for ablating body tissue using predicted maximum tissue temperature" and is incorporated herein by reference in its entirety. This patent describes systems and methods to ablate body tissue using an electrode for contacting tissue at a tissue-electrode interface to transmit ablation energy at a determinable power level. The systems and methods include an element to remove heat from the electrode at a determinable rate. The systems and methods employ a processing element to derive a prediction of the maximum tissue temperature condition occurring beneath the tissue-electrode interface. The processing element controls the power level of ablation energy transmitted by the electrode, or the rate at which the electrode is cooled, or both, based, at least in part, upon the maximum tissue temperature prediction.

U.S. Pat. No. 5,800,428 issued to Nelson et al. on Sep. 1, 1998 with the title "Linear catheter ablation system" and is incorporated herein by reference in its entirety. This patent describes a radio frequency (RF) ablation catheter system utilizes a flexible, tubular electrode that is selectively extendable from a distal end of a catheter body. The flexible, tubular electrode creates a continuous linear lesion when a longitudinal side of the electrode is arcuately positioned against an interior wall of the human body and the electrode is energized while a cooling fluid passes through the electrode. The catheter system also includes mechanisms for remotely manipulating and extending the electrode. Preferably, in some embodiments, the catheter body includes a catheter shaft and a flexible tip section such that the distal end of the catheter is steerable. The invention also includes a method of operating the RF catheter ablation system so as to create arcuate linear lesions.

U.S. Pat. No. 5,913,854 issued to Maguire et al. Jun. 22, 1999 with the title "Fluid cooled ablation catheter and method for making" and is incorporated herein by reference in its entirety. This patent describes a catheter assembly that includes a catheter shaft having a tip portion with a hollow interior and a linear ablation electrode spaced apart from the distal end of the tip portion. The electrode has an inner surface which is effectively fluidly exposed to the hollow interior so that a cooling fluid passing through the interior contacts the inner surface so to effectively cool the electrode. The electrode can include a series of band electrodes or one or more spiral electrodes. One method for making the tip portion involves mounting the electrode to a mandrel, filling the spaces between the edges of the electrode with a polymer and then removing the resulting tubular structure from the mandrel. The cooling fluid can pass through a hollow spiral electrode for enhanced cooling effectiveness.

U.S. Pat. No. 5,919,188 issued to Shearon et al. on Jul. 6, 1999 with the title "Linear ablation catheter" and is incorporated herein by reference. This patent describes a linear ablation catheter assembly includes a handle from which a hollow outer shaft extends. A hollow inner catheter is slidably housed within the outer shaft. The handle has a manipulator which moves the inner catheter along the interior of the outer shaft. The inner catheter has an opening alignable with and movable along a longitudinally-extending opening formed in the hollow outer shaft. A typically perforated, electrode is mounted to the inner catheter or the outer shaft is spaced-apart from the outer surface of the outer shaft. The handle is coupled to a source of energy-conducting liquid which flows through the inner catheter, out the inner catheter opening, past the perforated electrode, between fluid seals secured to the inner shaft and through the longitudinally-extending opening to ablate tissue. Moving the inner catheter opening along the longitudinally-extending opening causes a longitudinally-extending lesion to be created.

U.S. Pat. No. 6,015,407 issued to Rieb et al. on Jan. 18, 2000 with the title "Combination linear ablation and cooled tip RF catheters" and is incorporated herein by reference in its entirety. This patent describes an apparatus for ablating body tissue is provided that is particularly adapted for creating both linear and point lesions in the endocardium. The apparatus includes an elongate tubular member having a tip electrode and an ablation section mounted thereon. The ablation section includes one or more spaced electrodes, a fluid permeable foam material, and a fluid impermeable covering having a plurality of holes formed in it. The flow of conductive fluid to the ablation section during use allows contact to be maintained between the electrodes and the tissue to be ablated so as to minimize the formation of lesion breaks. The conductive fluid also serves to cool the tip electrode during its use by delivering the fluid to the tip electrode before routing it to the ablation section. In preferred embodiments, use of a shape wire and/or one or more pullwires allows the inventive apparatus to be more easily manipulated during the ablation procedure.

U.S. Pat. No. 6,017,338 issued to Brucker et al. on Jan. 25, 2000 with the title "Fluid cooled and perfused tip for a catheter" and is incorporated herein by reference in its entirety. This patent describes an ablation catheter which controls the temperature and reduces the coagulation of biological fluids on a tip of a catheter, prevents the impedance rise of tissue in contact with the catheter tip, and maximizes the potential energy transfer to the tissue, thereby allowing an increase in the lesion size produced by the ablation. The ablation catheter includes a catheter body. The ablation catheter also includes a tip for monitoring electrical potentials, and applying electrical energy to a biological tissue. A fluid source is positioned at one end of the catheter for supplying a fluid flow through the catheter to the tip means. Passages are positioned within the tip in a variety of manners for directing the fluid flow through the tip means to the exterior surface of the tip to control the temperature and form a protective fluid layer around the tip. Monitoring structure is also positioned within the tip structure for measurement of the electrical potentials in a biological tissue. Ablation structure is also positioned within the tip for application of ablative energy to the biological tissue.

U.S. Pat. No. 6,032,077 issued to Pomeranz on Feb. 29, 2000 with the title "Ablation catheter with electrical coupling via foam drenched with a conductive" and is incorporated herein by reference in its entirety. This patent describes an ablation catheter for ablating tissue, such as endocardial tissue. The ablation catheter includes a foam tip with an electrode embedded therein. Conductive fluid, such as saline solution, is pumped through the foam tip out to the tissue adjacent to the foam tip. The conductive fluid electrically couples the electrode embedded in the foam tip with the tissue to be ablated in order to effect ablation. The flow of the conductive fluid and the foam tip both help prevent any combustible products of the ablation from reaching the high current surfaces of the electrode itself.

U.S. Pat. No. 6,063,081 issued to Mulier et al. on May 16, 2000 with the title "Fluid-assisted electrocautery device" and is incorporated herein by reference. This patent describes an electrocautery instrument is provided with a hollow electrode having a source of conductive fluid coupled to a proximal end thereof. Conductive fluid is communicated through said electrode and expelled out of the distal end thereof during electrocautery, forming a "virtual electrode." The infused conductive liquid conducts the RF electrocautery energy away from the conductive electrode, thereby displacing the region of thermal generation and reducing the extent of burns and perforations caused by conventional electrocautery electrodes. In one embodiment, the electrode is partially disposed within and extends distally out of a retractable suction tube, such that smoke and fluid are aspirated from the electrocautery site. When the suction tube is fully advanced, the electrode is concealed therein, enabling suction without electrocautery to be performed.

U.S. Pat. No. 6,080,151 issued to Swartz et al. on Jun. 27, 2000 with the title "Ablation catheter" and is incorporated herein by reference. This patent describes an ablation catheter is disclosed having proximal and distal ends and an external surface, a lumen contained within the catheter body, a plurality of openings in the surface of the catheter, wherein the openings are in communication with the lumen, one or more electrodes secured within the catheter within the lumen and a source for conductive media to be introduced into the lumen to contact the electrode. The ablation catheter also may contain a conductive media flow control system which controls the flow of the conductive media through the openings in the surface of the catheter. Also disclosed is a process for ablation of human tissue including introducing an ablation catheter into the human body to a location to be ablated, passing a conductive media through a lumen of the catheter to contact one or more electrodes, passing the conductive media through the openings in the catheter body to contact the tissue to be ablated, and conducting energy from the electrode through the conductive media to the tissue for a sufficient period of time to ablate the tissue.

U.S. Pat. No. 6,315,777 issued to Comben on Nov. 13, 2001 with the title "Method and apparatus for creating a virtual electrode used for the ablation of tissue" and is incorporated herein by reference in its entirety. This patent describes creating a virtual electrode to ablate bodily tissue. The surgical apparatus includes an inner tube and an outer tube. The inner tube defines a proximal portion and a distal portion. The distal portion forms an orifice for distributing a conductive solution from the inner tube and further forms an electrode. The outer tube coaxially receives the inner tube such that the outer tube is slidable relative to the inner tube. With this configuration, the outer tube selectively blocks flow of conductive solution from the orifice. During use, conductive solution distributed from the orifice is subjected to a current from the electrode, thereby creating a virtual electrode.

U.S. Pat. No. 6,488,680 issued to Francischelli et al. on Dec. 3, 2002 with the title "Variable length electrodes for delivery of irrigated ablation" and is incorporated herein by reference. This patent describes a device for ablating tissue. The device includes a conductive element with a channel for irrigating fluid formed therein, which is in contact with a non-conductive microporous interface. All or a portion of the interface may be removable. When the interface is removed, a portion of the conductive element is exposed for use in ablating tissue. Methods of using the device and of removing the interface are also provided.

U.S. Pat. No. 6,522,930 issued to Schaer et al. on Feb. 18, 2003 with the title "Irrigated ablation device assembly" and is incorporated herein by reference. This patent describes a tissue ablation device assembly ablates a region of tissue of a body space wall of a patient. In a tissue ablation device assembly, an ablation member is disposed on the distal end portion of an elongated body. The ablation member includes an ablation element and at least one conductor coupled to the ablation element. A porous membrane covers the ablation element and defines an inner space between the ablation element and an inner surface of the porous membrane. A pressurizable fluid passageway extends between a fluid port on the proximal end portion of the elongated body and the inner space within the porous membrane. Fluid can pass from the fluid port, through the pressurizable fluid passageway, to the inner space. The porous membrane allows a volume of pressurized fluid to pass through the porous membrane to an exterior of the ablation member so as to irrigate the ablation element.

U.S. Pat. No. 7,104,989 issued to Skarda on Sep. 12, 2006 with the title "RF ablation catheter including a virtual electrode assembly" and is incorporated herein by reference in its entirety. This patent describes a virtual ablation electrode assembly includes a non-conductive outer cap fitted over an inner electrode to form a fluid chamber between a cap inner surface and an exterior surface of the electrode. The inner electrode includes an interior fluid trunk and one or more fluid distribution branches extending from the fluid trunk to the exterior surface. A plurality of pores extends between the cap inner surface and a cap outer surface. When the electrode is energized and when fluid is delivered through the one or more fluid distribution branches from the trunk, the conductive fluid fills the fluid chamber and flows out from the chamber through the plurality of pores of the cap establishing ionic transport of ablation energy from the inner electrode to a target site in close proximity to the cap.

U.S. Pat. No. 7,156,843 issued to Skarda on Jan. 2, 2007 with the title "Irrigated focal ablation tip" and is incorporated herein by reference. This patent describes a helical ablation electrode extends from a distal end of the shaft and includes a first portion extending from a first end winding about a first diameter, a second portion extending from the first portion and winding about a second diameter smaller than the first diameter, and a second end terminating the second portion. The electrode further includes a fluid lumen extending from a location in proximity to the first end of the electrode to a location in proximity to the second end of the electrode and in fluid communication with a fluid delivery lumen of the catheter shaft. An irrigation fluid delivered through the fluid delivery lumen of the catheter shaft, from a fluid port, passes through the fluid lumen of the ablation electrode to cool the electrode.

U.S. Pat. No. 7,163,537 issued to Lee et al. on Jan. 16, 2007 with the title "Enhanced ablation and mapping catheter and method for treating atrial fibrillation" and is incorporated herein by reference. This patent describes a catheter for measuring electrical activity and ablating tissue. The catheter includes an elongated generally-tubular catheter body. A non-retractable electrode assembly is mounted at the distal end of the catheter body. The electrode assembly includes a generally tubular ablation electrode formed of a material having shape-memory having a generally straight exposed region and at least one irrigation port in the exposed region through which fluid can pass from the inside to the outside of the ablation electrode. The exposed region is generally transverse to the catheter body. The electrode assembly further includes a tip at the distal end of the electrode assembly including a generally ball-shaped exposed region. First and second distal mapping electrodes are mounted distal to the exposed region of the ablation electrode. At least the first distal mapping electrode, and optionally the second distal mapping electrode, is incorporated into the generally ball-shaped exposed region of the tip. The catheter further includes an infusion tube extending through the catheter body and having a distal end in fluid communication with the proximal end of the ablation electrode.

U.S. Pat. No. 7,235,070 issued to Vanney on Jun. 26, 2007 with the title "Ablation fluid manifold for ablation catheter" and is incorporated herein by reference. This patent describes an ablation catheter employing one or more manifold arrangements to convey a conductive fluid medium to a target tissue. The manifold includes at least one inlet port in fluid communication with a fluid supply lumen running along at least a portion of the catheter. The inlet port or ports are in fluid communication with a larger outlet port. The outlet ports provide an outlet for the fluid to flow out of the catheter and against the target tissue. As such, the combination of at least the inlet port with the outlet port provides a flow path for fluid within the fluid lumen to flow through the manifold and to outside of the catheter. An electrode is arranged in the flow path of fluid within or adjacent the manifolds. As such, fluid may be energized and conduct ablation energy to the target tissue to ablate the tissue.

U.S. Pat. No. 7,435,250 issued to Francischelli et al. on Oct. 14, 2008 with the title "Method and apparatus for tissue ablation" and is incorporated herein by reference. This patent describes a device for ablating tissue. The device includes a conductive element with a channel for irrigating fluid formed therein, which is in contact with a non-conductive microporous interface. All or a portion of the interface may be removable. When the interface is removed, a portion of the conductive element is exposed for use in ablating tissue. Methods of using the device and of removing the interface are also provided.

U.S. Pat. No. 7,776,034 issued to Kampa on Aug. 17, 2010 with the title "Ablation catheter with adjustable virtual electrode" and is incorporated herein by reference. This patent describes an ablation catheter having a virtual electrode tip including a fluid manifold structure for operably varying the active area of the virtual electrode. An array of apertures in the distal end of the catheter forms the virtual electrode structure. A movable plug slides within the fluid manifold and seals against the interior walls of the fluid manifold. Conductive fluid cannot flow past the plug to fill the fluid manifold on the side of the plug opposite a fluid inlet channel into the fluid manifold. An electrode is positioned within the fluid manifold between the plug and the end wall of the fluid manifold adjacent the channel. By moving the plug within fluid manifold, only those portholes between the plug and the inlet channel will emit energized fluid. The effective length of an active ablation section of the virtual electrode is changed by repositioning the plug within the fluid manifold.

U.S. Pat. No. 7,819,866 issued to Bednarek on Oct. 26, 2010 with the title "Ablation catheter and electrode" and is incorporated herein by reference. This patent describes an ablation catheter including a shaft supporting one or more partially or completely exposed braided electrodes that may be positioned against a target tissue to ablate the tissue. The shaft may be pre-curved in a loop-like shape or any other shape to assist in positioning the electrode against a target tissue. The shaft may include a fluid lumen to direct a fluid material, which may be conductive, through one or more apertures or ports. The ports are adapted to direct the fluid past portions of the braided electrode to cool the electrode, flush blood away from the electrode, and to transfer ablation energy to the target tissue. Ablation energy may be delivered directly by the electrode and by way of a conductive fluid contacting the electrode. The shaft may further include a second lumen to provide a housing for a control wire that may be used to control the shape of the shaft.

U.S. Pat. No. 7,819,868 issued to Cao et al. on Oct. 26, 2010 with the title "Ablation catheter with fluid distribution structures" and is incorporated herein by reference. This patent describes an ablation catheter having improved fluid distribution structures. An ablation section at a distal end of the catheter is designed to provide a more uniform fluid flow emanating from the catheter. By creating a uniform fluid flow, a more uniform tissue lesion results and the possibility of charring the tissue is reduced. A combination of mesh material layers, porous materials, and dispersion channels or openings are used to achieve the uniform flow. The amount of fluid used as a virtual electrode to ablate the tissue is greatly reduced with the present invention. Further, the catheter may be used to create a single, uniform linear lesion by successive application of energy to adjacent portions of the ablation section, thus reducing the power required to create the desired lesion.

U.S. Pat. No. 7,815,635 issued to Wittkampf et al. on Oct. 19, 2010 with the title "Catheter and method, in particular for ablation and like technique" (also published as PCT Publication WO 2005048858 A1), and is incorporated herein by reference in its entirety. This patent describes a catheter, provided with an elongated body with an electrically conductive first end, wherein through said body at least one live wire extends which is connected to said first end and a channel for feeding a cooling fluid through said body, which channel is provided, in or near said first end, with at least one outlet opening and wherein, in said first end, a temperature sensor has been arranged, while said channel is thermally insulated from said first end.

U.S. Pat. No. 7,879,030 issued to Paul et al. on Feb. 1, 2011 with the title "Multipolar, virtual-electrode catheter with at least one surface electrode and method for ablation" and is incorporated herein by reference. This patent describes virtual-electrode catheters and methods for using such virtual-electrode catheters. For example, bipolar and multipolar, virtual-electrode catheters having at least one internal electrode and at least one surface electrode, and methods of using these catheters for treatment of cardiac arrhythmias via, for example, radiofrequency (RF) ablation are disclosed. The catheters may include a catheter body with an internal lumen extending within it and adapted to flowingly receive a conductive fluid. An exit feature defining a flow path from the internal lumen to the catheter's outer surface may exist through a sidewall of the catheter body. A conductor is mounted within the internal lumen adjacent to the exit feature and is adapted to deliver treatment energy to the tissue via the conductive fluid in the internal lumen. At least one surface electrode is mounted on the outer surface of the catheter body adjacent to the exit feature.

U.S. Pat. No. 8,394,093 issued to Wang et al. on Mar. 12, 2013 with the title "Irrigated ablation electrode assembly and method for control of temperature" and is incorporated herein by reference in its entirety. This patent describes an irrigated catheter having irrigation fluid directed at target areas where coagulation is more likely to occur so as to minimize blood coagulation and the associated problems. In one embodiment, an irrigated ablation electrode assembly for use with an irrigated catheter device includes a proximal member having at least one passageway for a fluid with an outlet disposed at an external surface of the proximal member; and a distal member connected with the proximal member and having an external surface. The distal member includes an electrode. The external surface of the proximal member and the external surface of the distal member meet at an intersection. The at least one passageway of the proximal member is configured to direct a fluid flow through the outlet toward a region adjacent the intersection.

United States Patent Application Publication 2011/0144639 by Govari published Jun. 16, 2011 with the title "Catheter with Helical Electrode" (now U.S. Pat. No. 8,920,415) and is incorporated herein by reference. This patent describes an invasive probe includes an insertion tube containing a lumen for providing an irrigation fluid and including a distal portion having a plurality of perforations therethrough providing fluid communication between the lumen and an outer surface of the insertion tube. At least one helical electrode is fitted over the distal portion of the insertion tube.

United States Patent Application Publication 2011/0270244 by Clark et al. published on Nov. 3, 2011 with the title "Irrigated ablation catheter with improved fluid flow" and is incorporated herein by reference. This application describes an irrigated ablation catheter includes a tip electrode with a thin shell and a plug to provide a plenum chamber. The tip electrode has an inlet of a predetermined size and noncircular shape, and outlets in the form of fluid ports formed in the thin shell wall. The plurality of the fluid ports is predetermined, as is their diameter. The tip electrode thus considers a diffusion ratio of total fluid output area to fluid input area, and a fluid port ratio. The tip electrode also considers a fluid inlet aspect ratio where the fluid inlet has a noncircular (for example, oval or elliptical) radial cross-section. The plenum chamber has a narrow proximal portion opening to a wider distal portion so that fluid pressure decreases while fluid velocity increases with the desired effect of increased turbulence which decreases momentum for a more uniform distribution of fluid in the tip electrode. Extending distally from the plug is a baffle member shaped to diffuse fluid entering the tip electrode and to house an electromagnetic position sensor.

United States Patent Application Publication 2013/0172873 by Govari et al. published on Jul. 4, 2013 with the title "Electrode Irrigation Using Micro-Jets" and is incorporated herein by reference. This application describes a medical device that includes an insertion tube, which has a distal end for insertion into a body of a subject, and a distal tip, which is fixed to the distal end of the insertion tube and is coupled to apply energy to tissue inside the body. The distal tip has an outer surface with a plurality of circumferentially distributed perforations formed therethrough. The perforations have diameters between 10 µm and 25 µm. A lumen passes through the insertion tube and delivers a cooling fluid to the tissue via the perforations.

Other Literature

BioSense Webster publication (BioSense Webster is a division of Johnson & Johnson Family of Companies) from 2010 by Nakagawa, H. with the title "Comparison of 12 and 56 Hole Electrodes for Open Irrigated Radiofrequency Ablation in a Canine Thigh Muscle Preparation: Improvement in Thrombus Reduction with 56 Small Irrigation Holes" was retrieved from www.biosensewebster.com/docs/Nakagawa.pdf on Mar. 25, 2014, and is incorporated herein by reference in its entirety.

BioSense Webster publication from 2011 by Shah D with the title "ThermoCool® SF Catheter provides "uniform cooling" with a reduced volume load. Case Report: anti-arrhythmic drug resistant atrial fibrillation ablation in a chronic end-stage renal failure patient" was retrieved from www.biosensewebster.com/docs/Shah.pdf on Mar. 25, 2014, and is incorporated herein by reference in its entirety.

SUMMARY OF THE INVENTION

In some embodiments, the present invention provides an apparatus that includes: an irrigated ablation electrode shell having a plurality of apertures each having an aspect ratio greater than 2.5. In some embodiments, the present invention provides an apparatus that includes: an irrigated electrode shell having a plurality of apertures, wherein at least one of the plurality of apertures has a hydraulic pressure drop of at least 0.10 psi (0.10 pounds per square inch=689.5 pascals) at a fluid flow rate of no more than 5 ml/min of water at 20 degrees C.

In some embodiments, the present invention provides an apparatus that includes: an ablation electrode that includes: a plurality of fluid passageways and slit-shaped apertures to give a high pressure drop through the electrode to provide for more uniform flow over exterior of shell and reduce propensity for aperture blockage; and an insert and shell having reduced electrode mass to provide a more thermally responsive tip to temperature anomalies in tissue during an ablation; wherein the electrode is configured to have a thin layer of water in contact with the interior of the electrode's shell through which fluid flows to enhance shell cooling and provide a thermal capacitor for thermal hot spots in a shell.

In some embodiments, the present invention provides an apparatus that includes: an ablation electrode that includes: a plurality of fluid passageways and slit-shaped apertures to give a high pressure drop through the electrode to provide for more uniform flow over exterior of shell and reduce propensity for aperture blockage; and an insert and shell having reduced electrode mass to provide a more thermally responsive tip to temperature anomalies in tissue during an ablation; wherein the electrode is configured to have a thin layer of water in contact with the interior of the shell to enhance cooling and provide a thermal capacitor for thermal hot spots in a shell.

In some embodiments, the present invention provides an apparatus that includes: an ablation electrode that includes: a plurality of fluid passageways and slit-shaped apertures to give a high pressure drop through the electrode to provide for more uniform flow over the exterior of a shell and reduce propensity for aperture blockage; and an insert and shell having reduced electrode mass to provide a more thermally responsive tip to temperature anomalies in tissue during an ablation.

In some embodiments, the present invention provides an apparatus that includes: an ablation electrode that includes a plurality of fluid passageways and slit-shaped apertures to provide for more uniform distribution of fluid over an exterior surface of the electrode and reduce propensity for aperture blockage.

In some embodiments, the present invention provides an apparatus that includes: an ablation electrode that includes a plurality of fluid passageways and slit-shaped apertures to provide for more uniform distribution of fluid over an exterior surface of the electrode and reduce propensity for aperture blockage.

In some embodiments, the present invention provides an apparatus that includes: an ablation electrode that includes a plurality of fluid passageways to provide for more uniform distribution of fluid over an exterior surface of the electrode.

In some embodiments, each one of the plurality of fluid channels has a high L/d value.

BRIEF DESCRIPTION OF DRAWINGS

FIG. 4A is a radial cross-sectional view of an arc segment of an insert 401 having a first alternate channel geometry.

FIG. 4B is a radial cross-sectional view of an arc segment of an insert 401 having a second alternate channel geometry.

FIG. 4C is a radial cross-sectional view of an arc segment of an insert 403 having a third alternate channel geometry.

FIG. 4D is a radial cross-sectional view of an arc segment of an insert 404 having a fourth alternate channel geometry.

FIG. 4E is a radial cross-sectional view of an arc segment of an insert 405 having a fifth alternate channel geometry.

FIG. 4F is a radial cross-sectional view of an arc segment of an insert 406 having a sixth alternate channel geometry.

FIGS. 5A, 5B, 5C, 5D, and 5E are plan flattened views of the outer circumference surface of each one of a plurality of inserts illustrating various embodiments having alternate channel geometric patterns on the exterior surface of each one of a plurality of inserts.

FIG. 11A is a longitudinal cross-sectional view an ablation electrode 1101 having an insert 1120 with a first configuration of internal fluid passages, according to some embodiments of the present invention.

FIG. 11B is a longitudinal cross-sectional view an ablation electrode 1102 having an insert 1121 with a second configuration of internal fluid passages, according to some embodiments of the present invention.

FIG. 27A is a longitudinal cross section view of an ablation device 2701 having an insert 2721, wherein the diameter of the fluid passageways 2782 is greater than the aperture diameter.

FIG. 27B is a longitudinal cross section of an ablation device 2702 having an insert 2722, in which the enlarged internal passageways contain a porous medium 2788 according to some embodiments of the present invention.

DETAILED DESCRIPTION OF FIGURES

Figure 1:
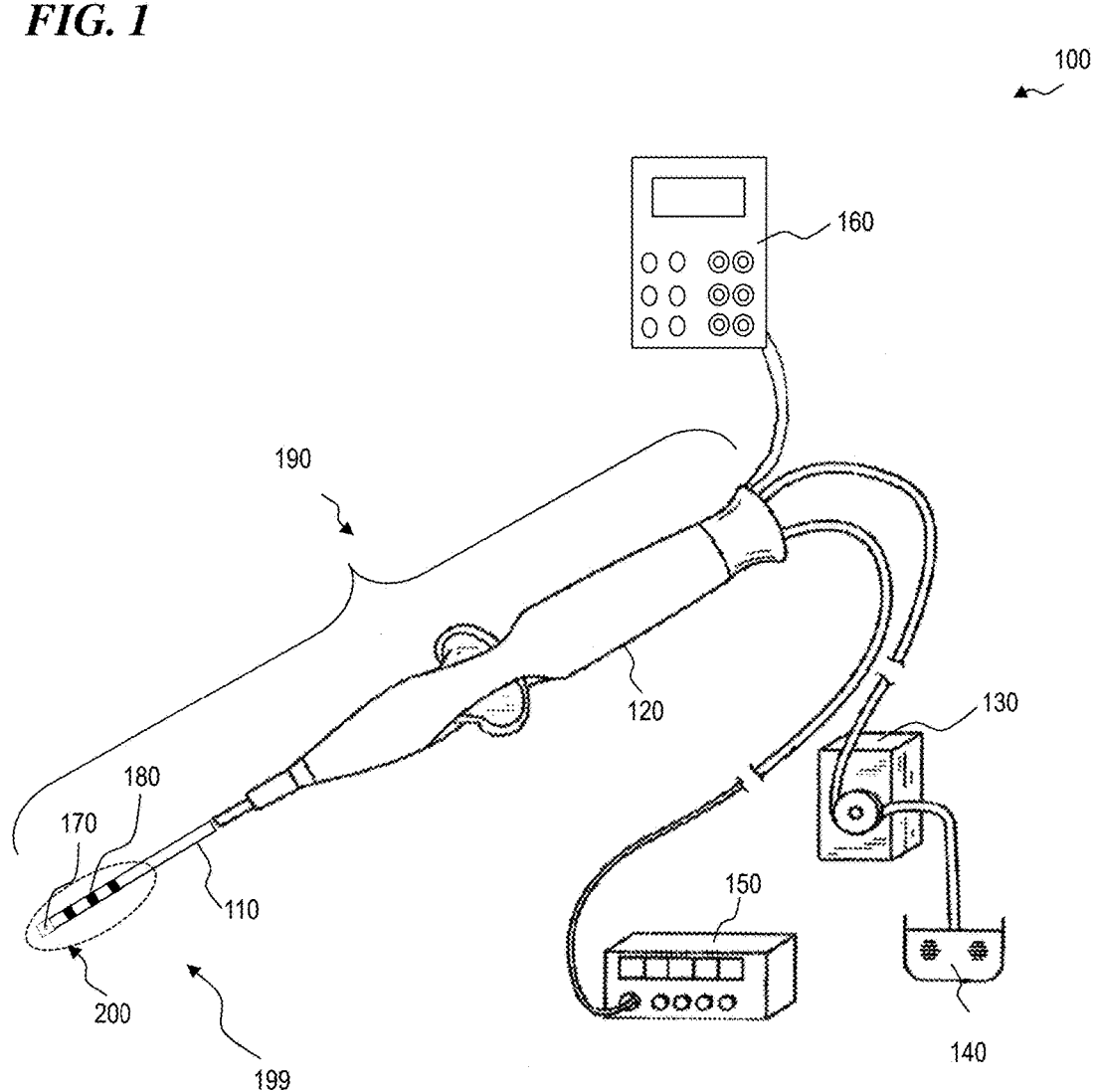
FIG. 1 is an isometric view of a cardiac-procedure system 100, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In some embodiments, the present invention provides an irrigated electrode mounted at the distal end of a catheter for use in cardiac procedures for both monitoring electrophysiological signals and ablating tissue. Some embodiments include a composite structure for an irrigated ablation electrode that includes an electrode shell in contact with biological tissue on its outer surfaces and an insert located within the electrode shell that includes one or more materials which incorporate the following features: channels for distributing fluid in order to contact interior surfaces of an electrode shell, fluid pathways for directing and uniformly distributing fluid to the exterior surface of an electrode shell through apertures in the shell wall, and use of low-density materials to reduce overall mass of an electrode. In use, an irrigated ablation electrode of some embodiments of the present invention will exhibit lower fluid flow rates for equivalent cooling of the ablation tip, provide a broader range of electrode temperature operating conditions, provide a more uniform electrode shell temperature and respond more rapidly to thermal anomalies while simultaneously minimizing blood coagulation and collateral tissue damage during a procedure.

In some embodiments, the present invention provides methods for manufacturing an insert with fluid channels exhibiting a high length to diameter ratio, L/d. In some embodiments of this method, multiple thin plates are laminated together to form an insert of the desired dimensions and hydraulic characteristics. Some embodiments include surface grooves that form fluid channels and/or through-holes are fabricated into a surface of a thin plate which, when combined with an adjacent plate, becomes an operably connected fluid channel. Fluid channels with non-circular or circular geometries over an extended length can be easily fabricated. Such channels have larger L/d's with a correspondingly higher hydraulic pressure which are desirable for obtaining a uniform distribution of fluid over the exterior surface of an electrode and reducing the potential for restricted flow through apertures during a procedure. In the following paragraphs, various numbered versions show some exemplary embodiments of the present invention.

Version 1

In this version 1 used in some embodiments of the present invention, an electrode shell consists of a thin metal cup with a generally cylindrical or hemispherical geometry with a multiplicity of apertures therethrough spaced in a geometric pattern over its exterior surface. An insert is formed from tubular materials with multiple channels fabricated into its exterior surface such that each channel in conjunction with the electrode shell forms a fluid passageway. In some embodiments, each fluid passageway is connected to one or more apertures in the electrode shell and to a fluid plenum within the ablation electrode, which is operably connected to an irrigation pump. A central lumen within the insert is used for instrumentation such as temperature, force or positional sensors or electrical wiring connected to external instrumentation. Remaining space within the insert is filled with one or more materials, preferably of low density, such as an adhesive, sealant, foam, air or liquid. A thin plate is joined to the proximal end of the ablation electrode to form a sealed interior space within the ablation electrode. A small extension tube is joined to the plate to provide a mechanical means for securing the electrode to a catheter shaft and to provide access to the interior space of the electrode. In some embodiments, the connecting means is constructed of an outside tube and an inside tube which together form an annular fluid passageway. The central lumen of the delivery tube contains connecting wires from the ablation electrode and is filled with an adhesive to form a fluid seal.

With respect to the insert, in some embodiments, the cross-sectional geometry of the channels is one of various shapes including rectangular, triangular, semi-circular or notched. In some embodiments, the channels are fabricated by machining flats into the exterior circular surface of an insert. In some embodiments, channels are fabricated from a thin foil formed into a corrugated geometry. In some embodiments, the pattern of the channels along the exterior surface includes a multiplicity of indentations generally aligned with the longitudinal axis of the electrode. In some embodiments, the channels are aligned circumferentially around the insert. In other embodiments, the channels have both axial and circumferential aspects generally forming a spiral pattern of specific pitch. In some embodiments, channels have different surface layouts from a multiplicity of equal-length segments in parallel to a single segment of extended length or a combination of the two layouts. In some embodiments, channels have a uniform depth over the entire surface of the insert or have variable depths and widths in order to obtain similar hydraulic resistance to fluid flow. In some embodiments, additional features are added to the channel defined by the grooves, such as orifices or nozzles, to obtain the desired overall hydraulic characteristics.

In operation, fluid passes into a fluid plenum at the proximal end of the electrode assembly and flows within the fluid passageways defined by channels in the exterior surface of the insert and the interior surface of the shell such that flowing fluid is in contact with the interior surface of the electrode shell. Fluid then exits the interior of the electrode through apertures in the shell, distributing fluid over the outside surfaces of the electrode shell. In some embodiments of the present invention, cooling of an electrode shell occurs on both its interior and exterior surfaces, providing the most efficient utilization of fluid.

Version 2

In this version 2 used in some embodiments of the present invention, the electrode shell is identical to that described in Version 1. In some embodiments, an insert is constructed from a tubular material having an interior space defined by its inner diameter and an exterior surface defined by its outer diameter. In some embodiments, multiple raised features, protuberances, are distributed over the exterior surfaces of the insert, consisting of small rectangular volumes affixed to the exterior surface of the insert. In some embodiments, the surface area occupied by the protuberances is a small percentage of the exterior surface area of the insert. In some embodiments, protuberances function as spacers which, in conjunction with the interior surface of the shell, form a reservoir to store fluid in contact with the interior surface of an electrode shell. In some embodiments, the interior space of the insert houses electrical wires operably coupling the ablation electrode to external instrumentation. In some embodiments, the interior space also functions as a fluid plenum operably coupled to the irrigation pump. In some embodiments, separate fluid passageways are fabricated within each protuberance, connecting its exterior surface to the central lumen. In some embodiments, each passageway within the insert is operably connected to an aperture in the electrode shell to distribute fluid over the exterior surface of the electrode shell.

In some embodiments of the insert, the material considerations are identical to those of Version 1. The pattern of protuberances over the outside surface of the insert formed by connecting the center point of each protuberance can be of various configurations, such as, for example, triangular, rectangular, linear or curvilinear. In some embodiments, fluid passageways are preferably circular in cross-section with passageways oriented perpendicular to the electrode longitudinal axis. In some embodiments, the diameter of the aperture and passageway are determined by the desired hydraulic characteristics of the electrode assembly. In other embodiments, other cross-sectional geometries and orientations are used and within the scope of the present invention, especially if increased hydraulic resistance though the electrode assembly is needed. In some embodiments the diameter of the fluid passageways is the same diameter as the apertures. In other embodiments, the diameter of the fluid passageways is smaller than the area of the opening of the apertures. In other embodiments, the diameter of the fluid passageways is larger than the area of the opening of the apertures. In some embodiments the diameter of the fluid passageways is constant along its entire length. In some embodiments, the diameter of the fluid passageways decreases toward the distal end of the passageways.

In some embodiments, the insert includes a single material throughout its body or a combination of materials that differ in either the longitudinal, radial or circumferential direction. Material composition is chosen to reduce the mass of the insert in order to provide a more rapid thermal response.

In another embodiment of Version 2, an insert is made of a porous material with an open-cell construction, meaning all pores within the material are in communication with other pores within the material. In some embodiments, fluid pathways are formed naturally by interconnection of individual pores within the material. In some embodiments, the porous material has an overall tubular shape with an exterior surface along its outer diameter and interior surface along its inner diameter. In some embodiments, the exterior surface of the porous material is located in contact with the interior surface of the electrode shell, allowing one or more pores to form a passageway in fluid communication with an aperture in the electrode shell. In some embodiments, the diameter of the pores is selected to provide the desired hydraulic pressure drop through the insert. Alternatively, in other embodiments, passageways as described above are fabricated into a porous material that allows fluid flow through the material to connect each aperture in the electrode shell to a fluid plenum within the insert. In some embodiments, an open-celled or other porous material forms a fluid passageway through the insert.

In operation, fluid passes into a fluid plenum at the center of the insert through fluid passageways therein to apertures in the shell distributing fluid over the outside surfaces of the electrode shell. In addition, fluid flows along fluid passageways in the proximal surface of the insert or from a plenum in the proximal region of the electrode shell into the gaps between the insert and interior surface of the electrode shell, forming an essentially quiescent fluid layer in contact with the interior of the electrode shell. In some embodiments, cooling of an electrode shell occurs primarily on its exterior surfaces and secondarily on its internal surfaces. In some embodiments, the internal fluid layer provides an enhanced thermal buffer to redistribute temperature anomalies or 'hot spots' using both conductive and convective mechanisms, and provides enhanced capability to absorb thermal energy using the heat capacity of water.

Version 3

In this version 3 used in some embodiments of the present invention, the electrode shell is identical to that described in Version 1. In some embodiments, an insert is constructed from a tubular material having an interior volume defined by its inner diameter from inner wall surface to opposite inner wall surface and an exterior surface defined by its outer diameter. In some embodiments, the exterior surface of the insert is in substantial contact with the interior surfaces of the electrode shell whose exterior surfaces are exposed to body tissue or fluids. In some embodiments, the interior space of the insert houses electrical wires operably coupling the ablation electrode to external instrumentation. In some embodiments, the interior space also functions as a fluid plenum operably coupled to an irrigation pump. In some embodiments, separate fluid passageways are fabricated within the body of the insert, connecting its exterior surface to the central lumen. In some embodiments, each passageway within the insert is operably connected to an aperture in the electrode shell to distribute fluid over the exterior surface of the electrode shell.

With respect to the insert, in some embodiments, the material considerations are identical to those of Version 1. In some embodiments, fluid passageways are preferably circular in cross-section with passageways oriented perpendicular to the electrode longitudinal axis. In some embodiments, the diameter of the aperture and passageway are determined by the desired hydraulic characteristics of the electrode assembly. In other embodiments, other cross-sectional geometries and orientations are used within the scope of the present invention, especially if increased hydraulic resistance though the electrode assembly is necessary. In some embodiments the diameter of the fluid passageways is the same diameter as the apertures. In some embodiments, the diameter of the fluid passageways is different from the diameter of the apertures. In some embodiments the diameter of the fluid passageways is constant along its entire length. In some embodiments, the diameter of the fluid passageway changes along its length.

In another embodiment of Version 3, an insert is made of a porous material with an open-cell construction, meaning substantially all pores within the material are in communication with other pores within the material. In some embodiments, fluid pathways are formed naturally by interconnection of individual pores within the material. In some embodiments, the porous material has an overall tubular shape with an exterior surface along its outer diameter and interior surface along its inner diameter. In some embodiments, the exterior surface of the porous material is located in contact with the interior surface of the electrode shell, allowing one or more pores to form a passageway in fluid communication with an aperture in the electrode shell. In some embodiments, the diameter of the pores is selected to provide the desired hydraulic pressure drop through the insert. Alternatively, in other embodiments, passageways as described above are fabricated into a porous material to connect each aperture in the electrode shell to a fluid plenum within the insert. In some embodiments, a porous material forms a fluid passageway through the insert.

In operation, fluid passes into a fluid plenum at the center of the insert through passageways therein to apertures in the shell distributing fluid over the outside surfaces of the electrode shell. In this alternative embodiment of Version 3, cooling of an electrode shell occurs primarily on its exterior surfaces and secondarily by heat conduction to the insert.

Version 4

In this version 4 used in some embodiments of the present invention, an insert with the desired mechanical and hydraulic features is constructed of plates of a planar material stacked and permanently joined together to function as a single entity. In some embodiments, channels are fabricated into a planar surface of one or more plates in a purposeful pattern. When positioned against the flat surface of an adjacent plate, the indentation forms a fluid passageway. In some embodiments, channels are aligned perpendicular to the longitudinal axis of an electrode and, in other embodiments channels are aligned parallel to the longitudinal axis. In some embodiments, features are fabricated into a single plate. In other embodiments, features are fabricated into multiple plates which form a single fluid channel when joined together. This approach is also used, in some embodiments, to make an insert with composite physical or thermo-physical properties in any axial, radial or circumferential direction over any volumetric region within an insert. Using this approach, fluid channels with smaller hydraulic diameters, defined as four times the cross-sectional area for fluid flow divided by wetted perimeter of fluid contained within the cross section, and longer channel lengths, L, are possible. In practice, it is possible using the invention to make channels with L/d's 10 to 100 times larger than current conventional irrigated ablation electrode designs.

Using a multiplicity of plates to form an insert allows consideration of surface fabrication methods for making fluid passageways. In current irrigated ablation electrodes, fluid channel diameters range from 0.004 to 0.010 inches (0.102 to 0.254 mm). To obtain an L/d ratio of five (5), passage lengths must range from 0.020 to 0.050 inches (0.508 to 1.270 mm). Drilling small diameters holes accurately over these depths is challenging, making larger L/d's difficult if not impossible to fabricate. However, larger L/d's are highly desirable in irrigated ablation electrodes to obtain more uniform flow and reduce the propensity for external aperture plugging. Expanding manufacturing capability to surface fabrication methods allows additional fabrication techniques to be considered. For example computer-numerical-control (CNC) milling, electro discharge machining (EDM), lasers, chemical etching, injection molding, precision die casting and various forms of 3D printing. With continued improvements in 3D printing, it will be possible to fabricate the entire insert of some embodiments in one step using inherent layering principle of 3D printing methods.

Version 5

In this version 5 used in some embodiments of the present invention, the apertures in the outer shell are slit-like elongated openings that have a length-to-width ratio of at least 2.5:1. Rectangular apertures give a higher pressure drop than circular apertures for the same flow area, while providing a longer length dimension, which reduces the likelihood of a particle completely or substantially blocking the aperture. In some embodiments, the slit-like apertures have a length-to-width ratio of at least 4:1. In some embodiments, the slit-like apertures have a length-to-width ratio of at least 5:1. In some embodiments, the slit-like apertures have a length-to-width ratio of at least 6:1. In some embodiments, the slit-like apertures have a length-to-width ratio of at least 7:1. In some embodiments, the slit-like apertures have a length-to-width ratio of at least 10:1. In some embodiments, the slit-like apertures have a length-to-width ratio of at least 15:1. In some embodiments, the slit-like apertures have a length-to-width ratio of at least 20:1. In some embodiments, the slit-like apertures are formed using laser ablation of the shell. In some embodiments, the slit-like apertures are formed using photolithography techniques as are known in the semiconductor industry, such as deep reactive ion etching (DRIE), to form steep-sided trenches that penetrate the shell.

Version 6

In this version 6 used in some embodiments of the present invention, the channels in the "insert" are filled with a sacrificial filler material such as glass or silicon oxide that can be later etched away, the shell is formed by electroplating, sputtering, or other suitable techniques to deposit one or more suitable metals over this etchable material and the rest of the "insert" to form the hard shell. The slit-like apertures are formed using the photolithography techniques discussed above for Version 5, to form steep-sided trenches that penetrate the plated-on shell, and a selective etchant is then applied through the slit-like apertures to remove the sacrificial filler material that was previously placed in the "insert." The term "insert" is used in the description of this version, since the structure ends up within the shell, but the shell is deposited in place onto this structure.

Version 7

In this version 7 used in some embodiments of the present invention, the pressure of the fluid pumped into the cooled tip of the ablation catheter is periodically pulsed to a pressure of at least 25% higher than otherwise maintained and then returned to a lower "normal" pressure value that is adequate to cool the tip. Increasing fluid pressures increases both the hydraulic pressure and flow at each aperture in the electrode shell to help dislodge particles from the aperture and provide an increased velocity to temporarily enhance surface cooling of body tissue adjacent to and in contact with the ablation tip. In some other embodiments, the periodically pulsed pressure is at least 50% higher than otherwise maintained. In some other embodiments, the periodically pulsed pressure is at least 75% higher than otherwise maintained. In some other embodiments, the periodically pulsed pressure is at least 100% higher than otherwise maintained. In some other embodiments, the periodically pulsed pressure is at least 150% higher than otherwise maintained. Using a lower flow rate for part of a cardiac procedure reduces the amount of fluid added to the patient's bloodstream, while periodically pulsing the flow provides the cooling benefits of a higher flow rate. Employing this strategy can reduce the risk of fluid overload in patients undergoing a cardiac procedure especially for longer procedures which can last four hours or more.

In some embodiments, the pressure is also temporarily raised to further cool the tip when needed to maintain a safe operational temperature of the tip, and this increase in fluid pressure and flow is triggered when the device senses a tip temperature that is increasing toward or exceeding a defined limit temperature. In some embodiments, the increase in fluid pressure and flow is triggered by a simulation model that takes into account the amount of RF energy being applied to the tip and the anticipated heat flow away from the tip that is provided by both the fluid flow through the catheter and the blood flow around the catheter.

Figure 3A:
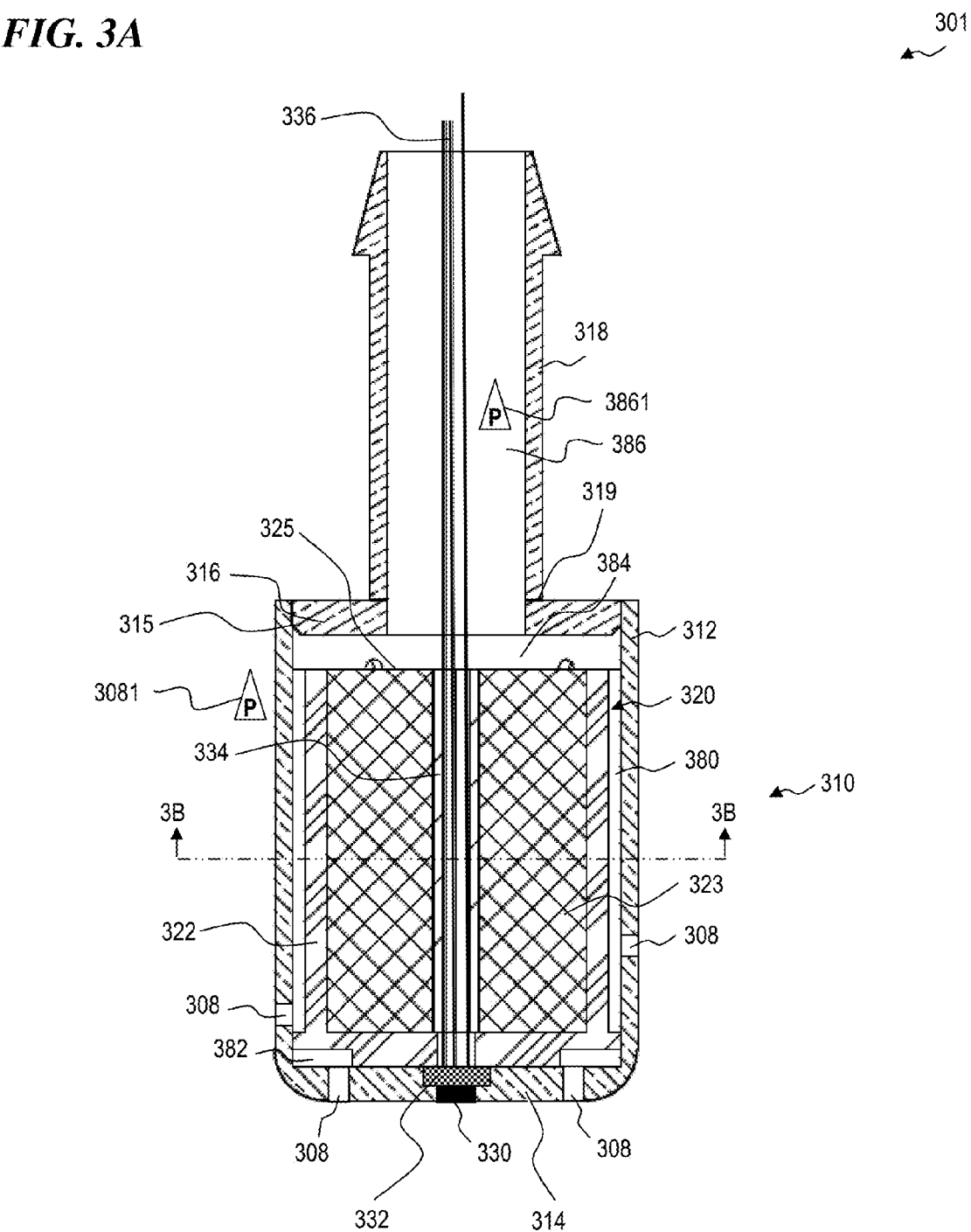
FIG. 3A is a longitudinal cross-sectional view of the ablation electrode assembly 301 according to some embodiments of the present invention.
Figure 3B:
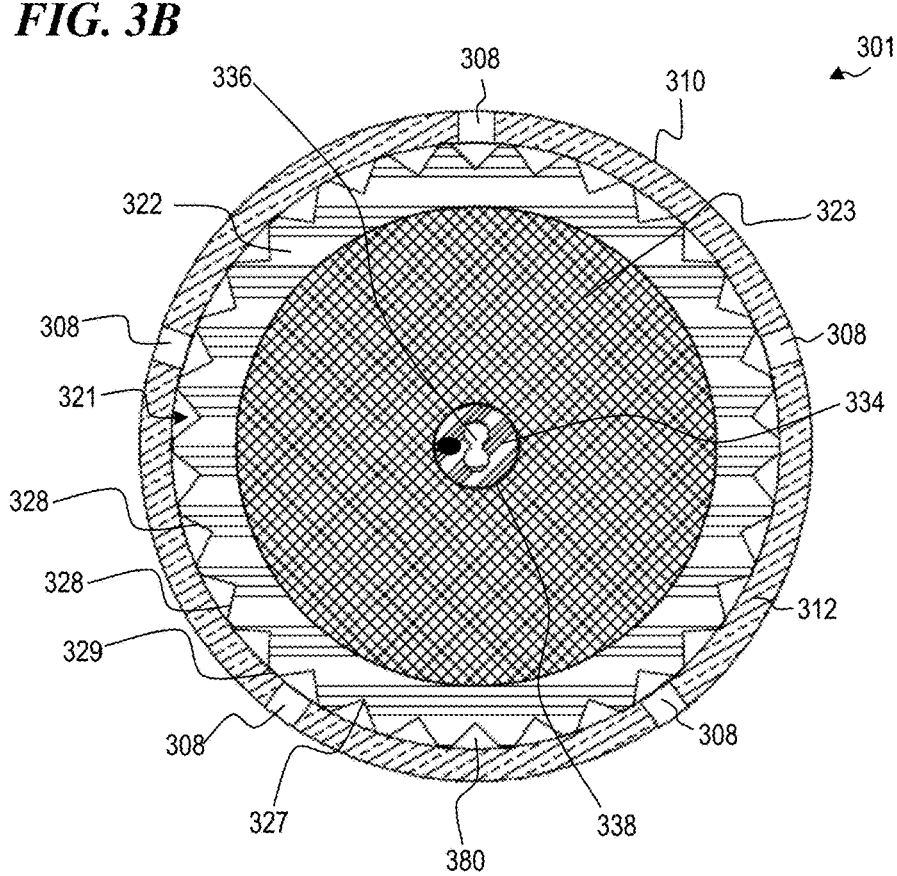
FIG. 3B is a radial cross-sectional of the ablation electrode assembly according to some embodiments of the present invention.
Figure 3C:
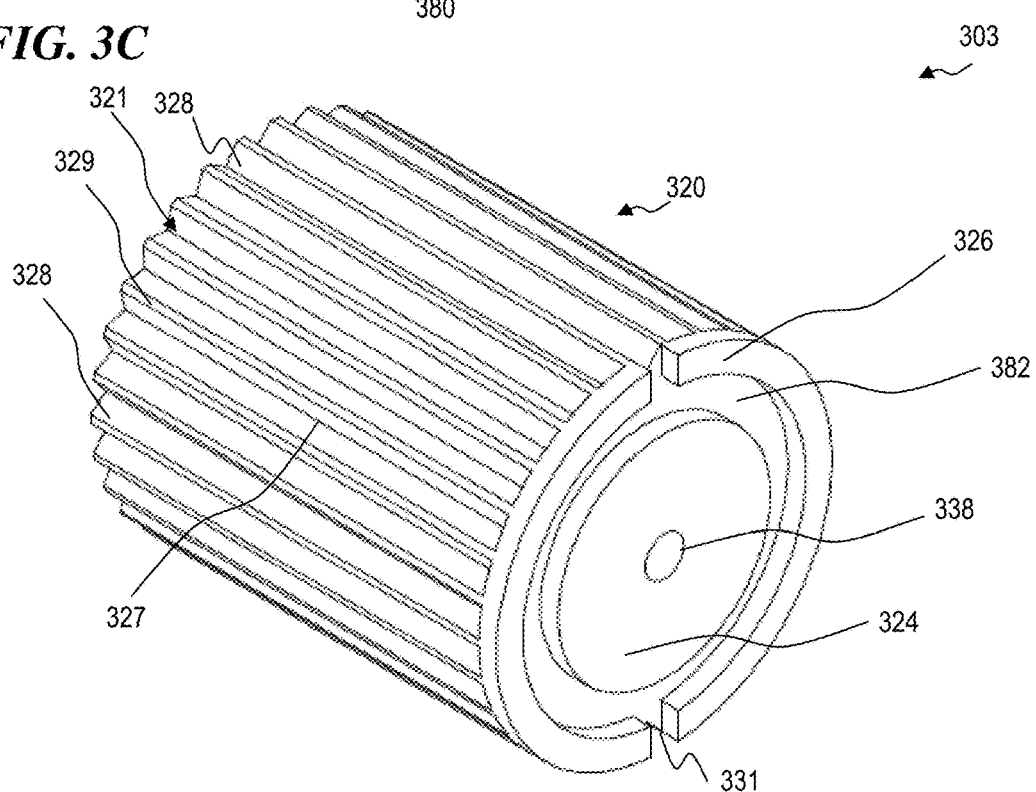
FIG. 3C is an isometric view of the insert 320 of the ablation electrode assembly 301 according to some embodiments of the invention.

Version 8—Electrode Shell with Active Fluid Layer (See FIGS. 3A, 3B & 3C)

This version 8 used in some embodiments of the present invention includes an electrode shell with apertures in which the interior of the shell has an insert made of low mass and has fluid channels on its exterior surfaces to form a space between shell and insert which has fluid flow during operation. The inventive features are three fold: first is use of high L/d channels and/or use of slits instead of circles for the apertures to give a high pressure drop through the electrode to provide for more uniform flow over exterior of shell and reduce propensity for aperture blockage; second is reduced electrode mass to provide a more thermally responsive tip to temperature anomalies in tissue during an ablation; and third is a thin layer of water in contact with the interior of the shell through which fluid flows to actively enhance shell cooling and provide a thermal capacitor to absorb thermal hot spots in a shell. The following Table 1 lists features of come embodiments and advantages that the features provide:

TABLE 1

| Feature | Benefit |
|---|---|
| Thin, active fluid layer in contact with interior surface of electrode shell | Lowest fluid flow More accurate electrode temperature representation of shell overall temperature |
| Electrode with low mass | Faster response to temperature anomalies in tissue heating |
| Fluid channels with L/d greater than 5 and single passageway per aperture OR Apertures consisting of slits with aspect ratio greater than 2.5 | Uniform flow over exterior surface |
| Fluid passageways within electrode with pressure drop greater than 0.1 psi (689.5 pascals) at 5 ml/min | Reduced propensity for aperture blockage |

Figure 8A:
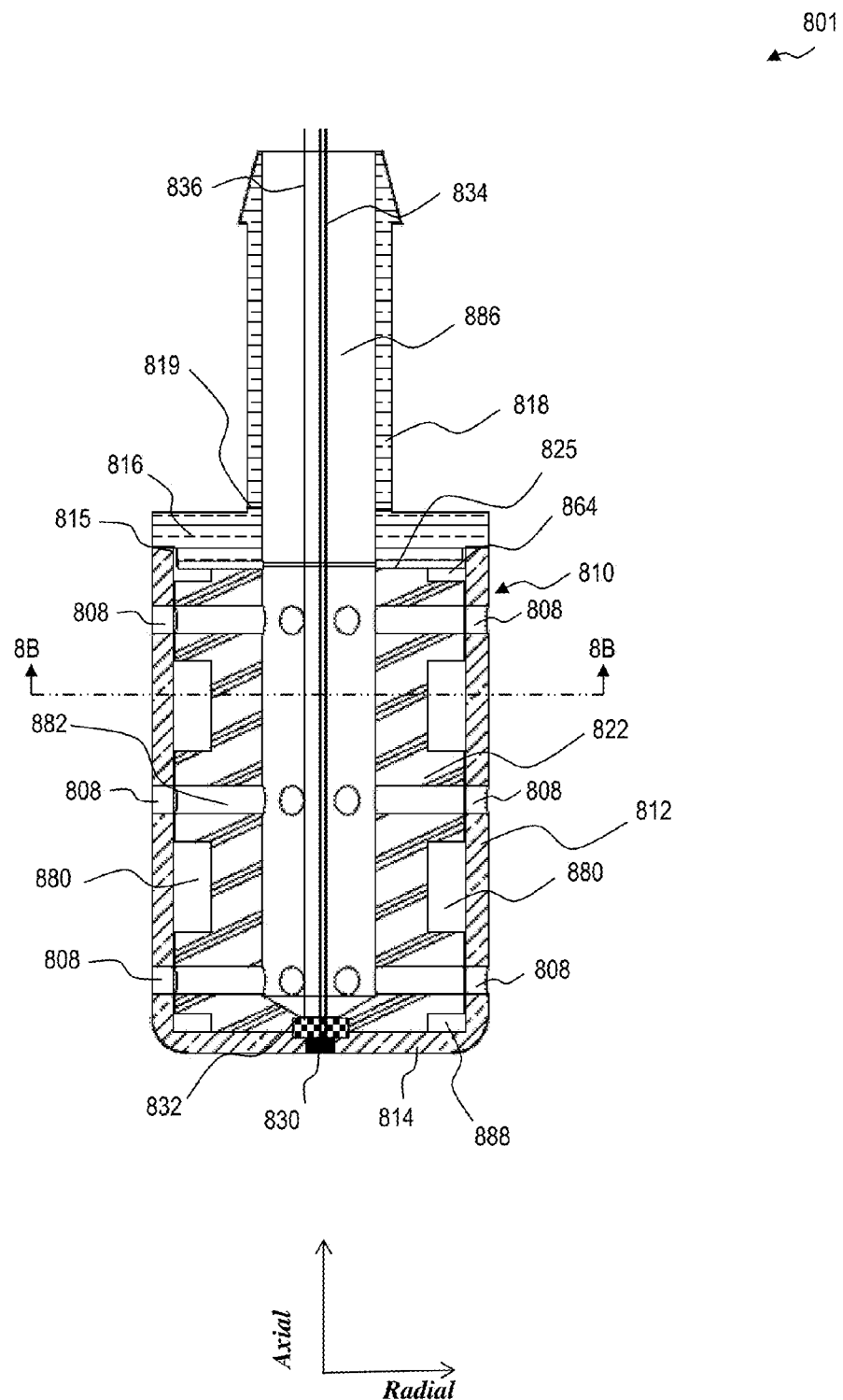
FIG. 8A is a longitudinal cross-sectional view of an ablation electrode assembly 801 with protuberances on the exterior surface of the insert 820 for forming a fluid layer in contact with the shell 810 and with separate fluid passageways for each shell aperture.
Figure 8B:
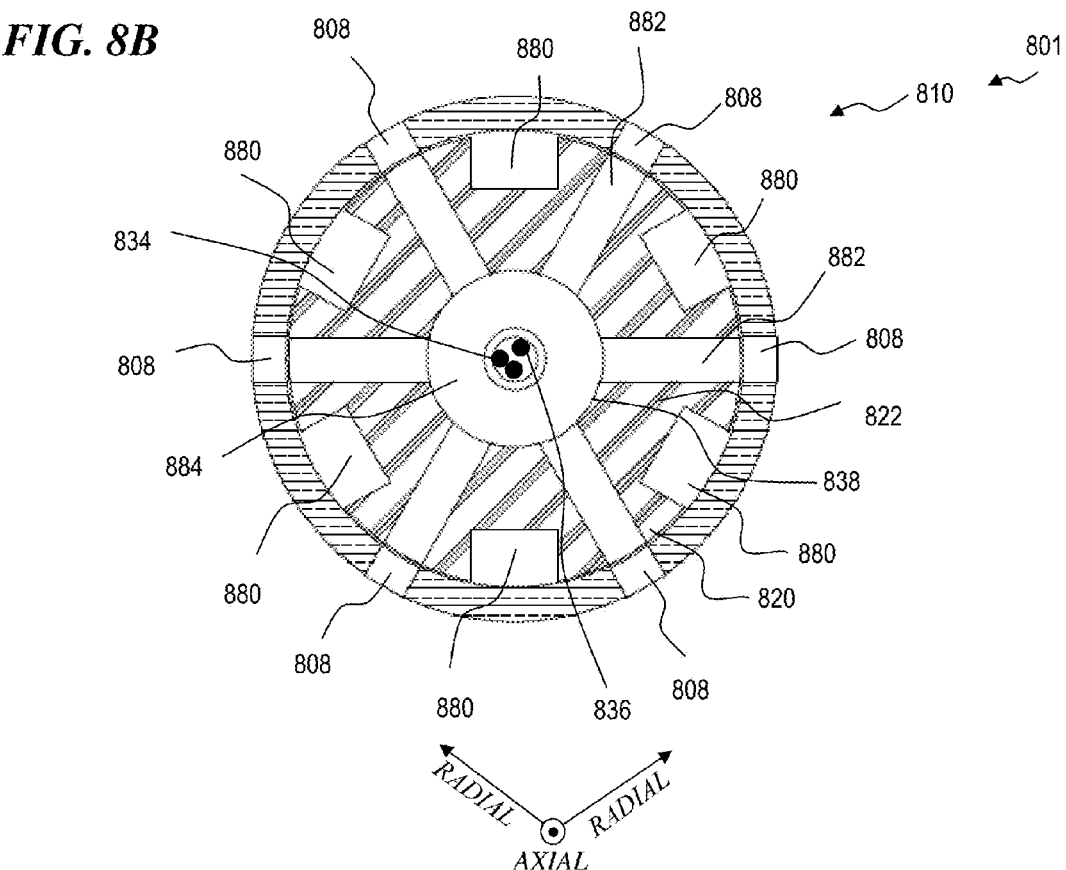
FIG. 8B is a radial cross-sectional view of ablation electrode assembly 801 along a plane perpendicular to the longitudinal axis with protuberances on the exterior surface of the insert 820.
Figure 8C:
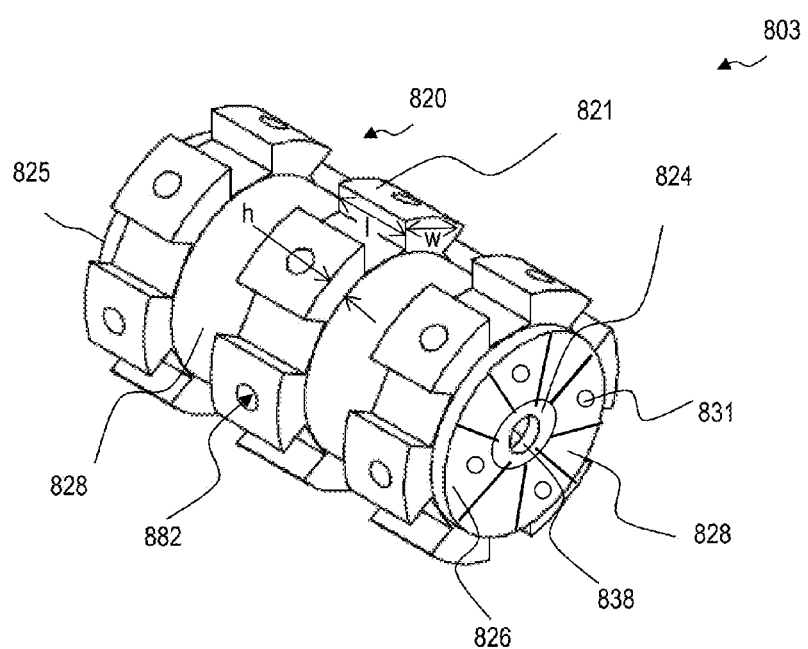
FIG. 8C is an isometric view of insert 820 with protuberances on the exterior surface of the insert 820.

Version 9—Electrode Shell with Quiescent Fluid Layer (See FIGS. 8A, 8B & 8C)

This version 9 used in some embodiments of the present invention includes an electrode shell with apertures in which the interior of the shell has an insert made of low mass and fluid channels therein with a space between shell and insert which is filled with a quiescent fluid during operation. The inventive features are three fold: first is use of high L/d channels and/or use of slits instead of circles for the apertures to give a high pressure drop through the electrode to provide for more uniform flow over exterior of shell and reduce propensity for aperture blockage; second is reduced electrode mass to provide a more thermally responsive tip to temperature anomalies in tissue during an ablation; and third is a thin layer of quiescent (substantially non-moving) water in contact with the interior of the shell to provide a thermal capacitor for thermal hot spots in the shell. The following Table 2 lists features of some embodiments and advantages that the features provide:

TABLE 2

| Feature | Benefit |
| --- | --- |
| Thin, quiescent fluid layer in contact with interior surface of electrode shell | Lower overall fluid flow Better electrode temperature representation of shell overall temperature |
| Electrode with low mass | Faster response to temperature anomalies in tissue heating |
| Fluid channels with L/d greater than 5 and single passageway per aperture AND/OR Apertures consisting of slits with aspect ratio greater than 2.5 | More Uniform flow over exterior surface compared to current conventional designs |
| Fluid passageways within electrode with pressure drop greater than 0.1 psi (689.5 pascals) at 5 ml/min | Reduced propensity for aperture blockage |

Figure 10A:
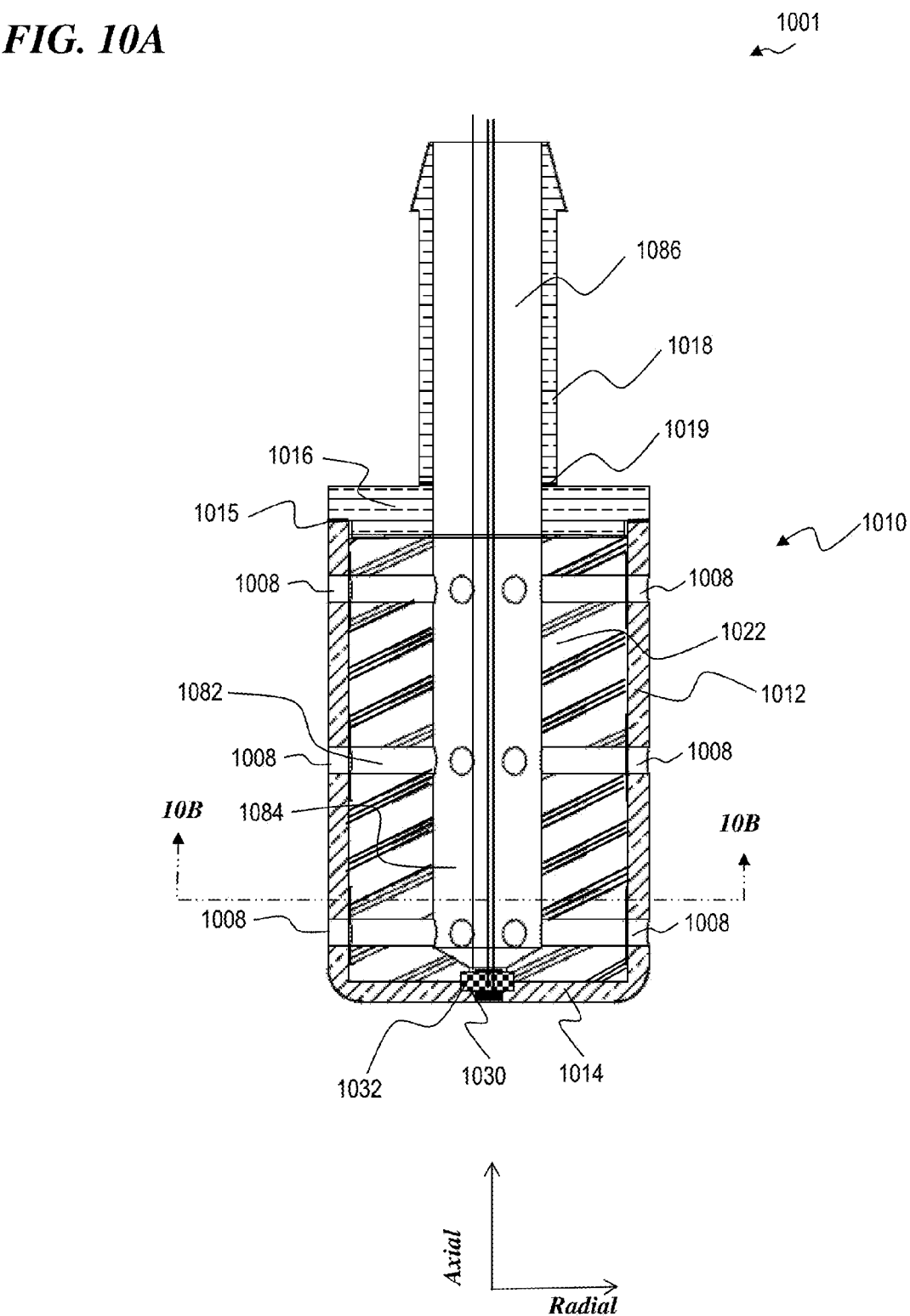
FIG. 10A is a longitudinal cross-sectional view of an ablation electrode assembly 1001 that uses an insert 1020 with internal fluid passageways and with the exterior surface of the insert 1020 in substantial contact with the electrode shell 1010.
Figure 10B:
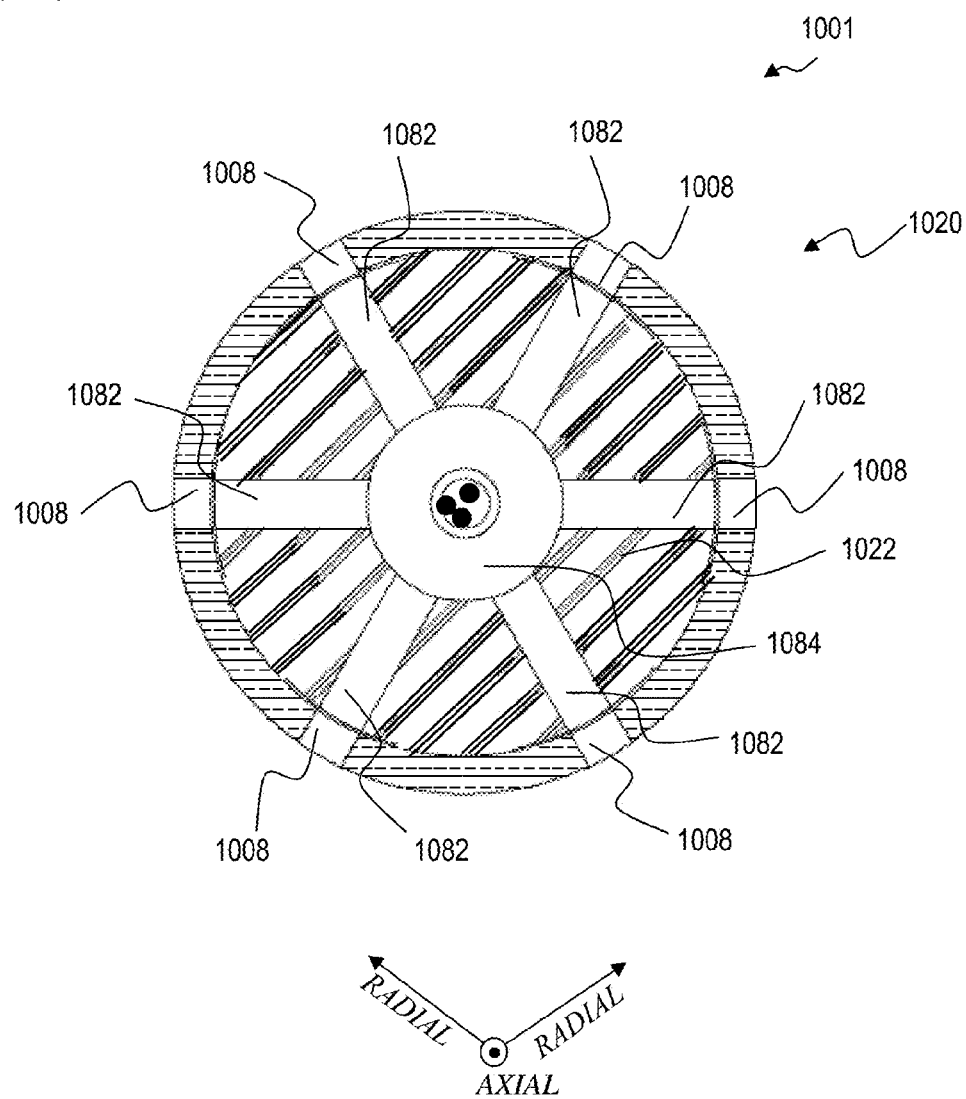
FIG. 10B is a radial cross-sectional view of ablation electrode assembly 1001 that uses insert 1020 with internal fluid passages and with the exterior surface of the insert in substantial contact with electrode shell 1010.

Version 10—Electrode Shell with Low Mass Insert (See FIGS. 10A & 10B)

This version 10 used in some embodiments of the present invention includes an electrode shell with apertures in which the interior of the shell has an insert made of low mass and fluid channels therein. The inventive features are twofold: first is use of high L/d channels and/or use of slits instead of circles for the apertures to give a high pressure drop through the electrode to provide for more uniform flow over exterior of shell and reduce propensity for aperture blockage; and second is reduced electrode mass to provide a more thermally responsive tip to temperature anomalies in tissue during an ablation. The following Table 3 lists features of some embodiments and advantages that the features provide:

TABLE 3

| Feature | Benefit |
| --- | --- |
| Electrode with low mass | Faster response to temperature anomalies in tissue heating |
| Fluid channels with L/d greater than 5 and single passageway per aperture OR Apertures consisting of slits with aspect ratio greater than 2.5 | More uniform flow over exterior surface compared to current conventional designs |
| Fluid passageways within electrode with pressure drop greater than 0.1 psi (689.5 pascals) at 5 ml/min | Reduced propensity for aperture blockage |

Figure 20A:
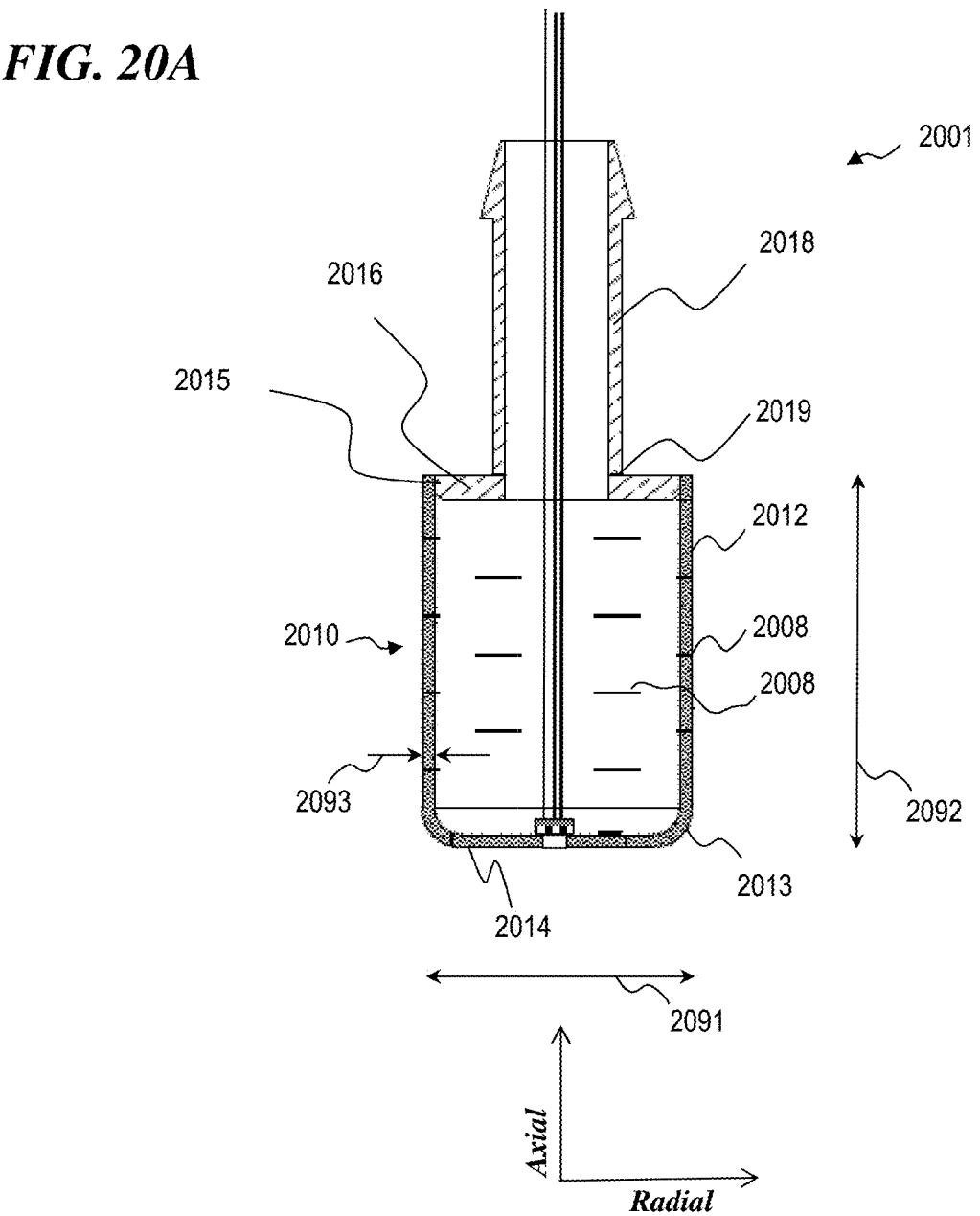
FIG. 20A is a longitudinal cross-sectional view of an irrigated ablation electrode 2001 with rectangular (slit-shaped) apertures for passage of fluid to the exterior surface.
Figure 20B:
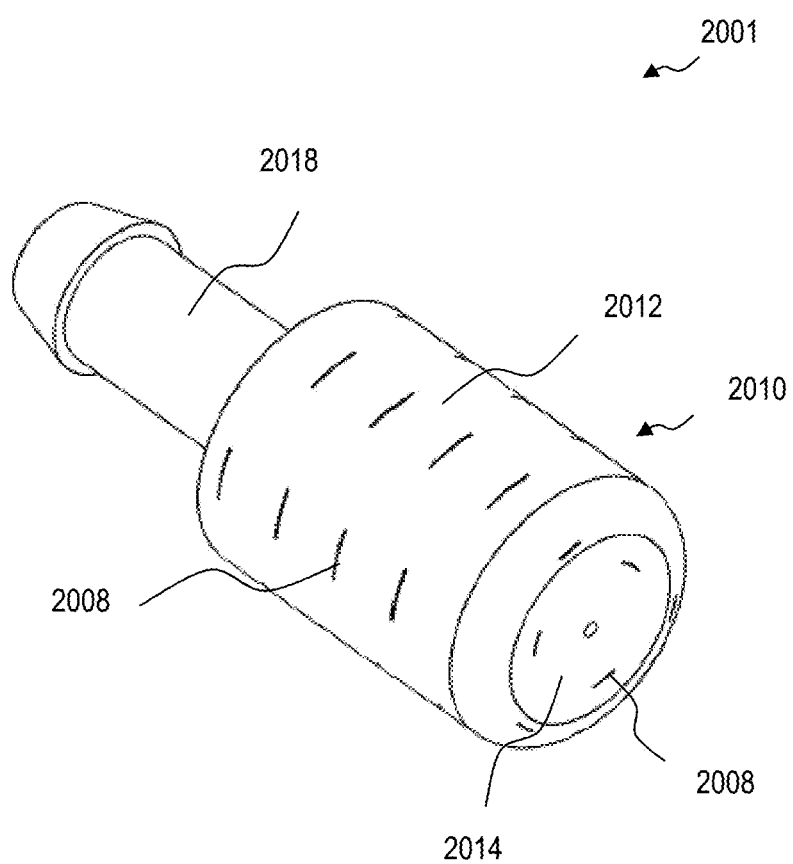
FIG. 20B is an isometric view of irrigated ablation electrode 2001 with rectangular apertures for passage of fluid to the exterior surface.

Version 11—Hollow Electrode Shell (See FIGS. 20A & 20B)

This version 11 used in some embodiments of the present invention includes an electrode shell with apertures in which the interior of the shell is filled with fluid. This is the most popular design and one that has the highest temperature depression and least responsiveness to thermal anomalies. The inventive feature is use of slits instead of circles for the apertures to provide for more uniform distribution of fluid over the exterior surface of the electrode and reduce propensity for aperture blockage. The following Table 4 lists features of some embodiments and advantages that the features provide:

TABLE 4

| Feature | Benefit |
| --- | --- |
| Apertures consisting of slits with aspect ratio greater than 2.5 | More uniform flow over exterior surface compared to current conventional designs |

TABLE 4-continued

| Feature | Benefit |
| --- | --- |
| Electrode with pressure drop greater than 0.1 psi (689.5 pascals) at 5 ml/min | Reduced propensity for aperture blockage |

Combination Versions

In these versions of the present invention, two or more of the versions 1-11 are combined and used in a single device of the present invention.

Summary of Advantages

In some embodiments of the present invention, fluid flows through an insert through individual passageways to apertures in an electrode shell to distribute water over its external surface. Fluid also moves along internal fluid channels in thermal contact with the interior surfaces of an electrode shell. Because both surfaces are cooled simultaneously, fluid is used efficiently to cool the electrode shell, resulting in substantially reduced overall fluid flow rates.

In some embodiments of the present invention, fluid forms a relatively quiescent liquid reservoir in contact with the interior surfaces of an electrode shell to provide a means for absorbing and redistributing concentrations of thermal energy within the wall of an electrode shell using the thermal conductivity, specific heat and latent heat for vaporization of a fluid.

In some embodiments of the present invention, the mass of an electrode is reduced to increase the thermal responsiveness of an ablation electrode to temperature anomalies encountered during tissue ablations.

In some embodiments of the present invention, the hydraulic characteristics of the fluid channels are balanced to uniformly distribute fluid over the exterior surfaces of an ablation electrode.

In some embodiments of the present invention, hydraulic pressure within a fluid plenum of an ablation electrode is maintained at level to provide a means whereby fluid is uniformly distributed to each aperture of an ablation electrode.

In some embodiments, apertures are designed with a non-circular profile to increase pressure drop across the aperture thereby increasing the uniformity of fluid distribution to each aperture.

In some embodiments of the present invention, hydraulic pressure within a fluid plenum of an ablation electrode is maintained at level to provide a means whereby temporary restrictions or blockages may be dislodged from an aperture.

In some embodiments of the present invention, a porous material is used to provide a structure which simultaneously maintains a reservoir of fluid in contact with the interior surfaces of an electrode shell by virtue of pores in contact with the shell and provides passageways for flow to the exterior surface of the electrode shell for pores in contact with apertures in the electrode shell.

In some embodiments of the present invention, an insert is designed using plates stacked together and joined to form a single body in order to obtain desired physical, hydraulic and thermal characteristics.

Some embodiments of the present invention include a method for designing fluid passageways within an ablation electrode to provide a uniform fluid flow to the exterior surface of an ablation electrode over a range of fluid flow rates.

Some embodiments of the present invention include a method for cooling both the interior surface and exterior surfaces of an ablation electrode to reduce fluid volume used during a procedure.

Some embodiments of the present invention include a method for reducing the temperature of a fluid connector used to join an ablation electrode to a catheter shaft.

Some embodiments of the present invention include a method for designing fluid passageways within an ablation electrode to provide a means whereby temporary restrictions are dislodged from the fluid path by action of hydraulic forces.

Some embodiments of the present invention include a method for fabricating a composite insert using layers of material with differing characteristics and joining the layers together to form a single body.

Some embodiments of the present invention include a method for performing cardiac ablations by selecting a delivered power and electrode operating temperature and then adjusting fluid flow rate to achieve the selected electrode operating temperature without increased coagulum formation or collateral tissue damage.

Some embodiments of the present invention include a method for performing cardiac ablations using an electrode with low thermal capacitance to more rapidly sense temperature aberrations or anomalies in tissue heating and consequently alter ablation conditions to minimize collateral damage to tissue such as perforations or lacerations caused by steam formation within tissue or to reduce coagulum formation.

Some embodiments of the present invention include irrigated electrode assemblies and methods for manufacturing and using such irrigated ablation electrode assemblies.

FIG. 1 is an isometric view of a cardiac-procedure system 100, according to some embodiments of the present invention. In some embodiments, cardiac-procedure system 100 includes an ablation electrode assembly 199 in conjunction with catheter assembly 190 operably connected to an RF (radio-frequency) generator assembly 150 and a fluid pump assembly 130. In some embodiments, as seen in FIG. 1, ablation electrode assembly 199 is part of an irrigated ablation catheter 190 that includes handle 120, shaft 110 and ring electrodes 180 and irrigated ablation electrode assembly 170. In some embodiments, catheter 190 is operably coupled to fluid pump assembly 130, RF generator 150 and EP (electrophysiology) monitoring unit 160 to form a system 100 for performing cardiac ablations. In some embodiments, ablation electrode assembly 170 is attached to catheter shaft 110 at its distal end and is operably coupled to fluid, electrical and mechanical means to deliver electrical energy and fluid and monitor a number of selected operational parameters such as electrode temperature, delivered RF power and tissue impedance. In some embodiments, fluid pump 130 is operably coupled to fluid reservoir 140 to supply fluid to ablation electrode 170 for purposes of cooling the electrode and surrounding tissue and enhancing transfer of RF energy to tissue.

FIG. 1 provides a general perspective of an irrigated ablation catheter system 100 having a catheter assembly 190, a radio frequency (RF) generator assembly 150, a fluid pump assembly 130 with connecting fluid reservoir 140 and an electrophysiology (EP) monitoring system 160. In some embodiments, irrigated catheter assembly 190 includes handle 120, catheter shaft 110, and an ablation tip unit 199 that includes ring electrodes 180 and irrigated electrode assembly 170 attached thereto at its distal end. In some embodiments, catheter handle 120 contains features to operably connect RF generator 150, fluid pump 140 and EP monitoring means 160. The structural and functional features of catheter assembly 190, RF generator 150 and pump assembly 140 and EP monitoring means 160 are well known to those skilled in the art. For example, in some embodiments, the RF generator is a Maestro 3000 Cardiac Ablation System from Boston Scientific Corporation, a Stockert RF 70 from BioSense Webster a division of Johnson & Johnson, a Cardioblate 6800 Surgical RF Generator from Medtronic, Inc, or an IBI-1500T Cardiac Ablation Generator from Irvine Biomedical, a division of St. Jude Medical, Inc. In some embodiments, for example, the fluid pump assembly is any suitable assembly including fixed volume roller pumps, variable volume syringe pumps, and assemblies specifically manufactured for cardiac ablation such as the CoolFlow™ irrigation pump from BiosSense Webster. In some embodiments, for example, the EP monitoring station is a CARTO® 3 System by BioSense Webster or ENSITE™ Velocity™ Cardiac Mapping System by St. Jude Medical, Inc.

Figure 2A:
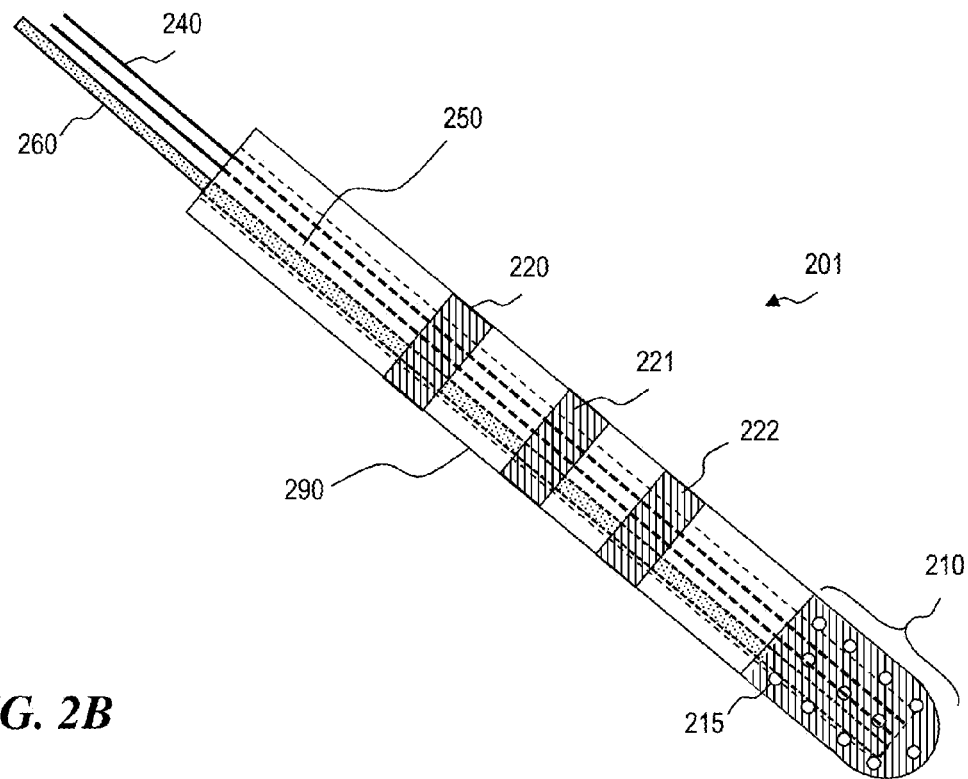
FIG. 2A is an enlarged longitudinal isometric side view of the distal region of an ablation tip unit 201, wherein ablation tip unit 201 has circular apertures 215, according to some embodiments of the present invention.

FIG. 2A is an isometric view of an ablation tip unit 201, according to some embodiments of the present invention. In some embodiments, ablation tip unit 201 is used for ablation tip unit 199 of FIG. 1. In some embodiments, ablation tip unit 201 includes irrigated ablation electrode assembly 210 connected to catheter shaft 290 having a central lumen 250 for containing fluid tube 260 and electrical wiring 240. In some embodiments, catheter shaft 290 includes a series of one or more ring electrodes 220, 221 and 222 spaced at discrete intervals along the outer surface of catheter shaft 290. The number of ring electrodes may vary but in some embodiments, is four (4) for ablation catheters. In some embodiments, ring electrodes are used for monitoring electrical impulses in cardiac tissue during electrophysiology procedures to determine the precise location for a cardiac ablation. In certain applications, one or more ring electrodes are used as return electrodes during cardiac ablation. In some embodiments, ablation electrode assembly 210 is attached to catheter shaft 290 and generally oriented at the distal end of the catheter shaft, while in other embodiments, other orientations are used and are within the scope of the present invention. In some embodiments, ablation electrode assembly 210 is mechanically coupled to catheter lumen 250 and coupled to fluid tube 260 in communication with a fluid pump 130. In other embodiments, central lumen 250 is used to couple ablation electrode 210 to fluid pump 130. In some embodiments, ablation electrode assembly 210 includes an outer shell 310 (see FIG. 3A) of an electrically, and preferably thermally, conductive material (e.g., in some embodiments, a metal) known to those skilled in the art for delivery of electrical ablative energy to target tissue. In some embodiments, ablation electrode assembly further includes at least one temperature-sensing mechanism 330 (see FIG. 3A) disposed therein and operably connected to RF generator assembly 150. In some embodiments, ablation electrode assembly 210 has at least one fluid passageway 380 (see FIG. 3B) and at least one fluid outlet 215 for delivery of fluid to the external surface of the ablation electrode assembly and to tissue in contact with the exterior surface of the ablation electrode assembly. There are a number of ablation electrode designs envisioned within the scope of the present invention including tip electrodes, ring electrodes, split electrodes, pin electrodes or combinations thereof.

Figure 2B:
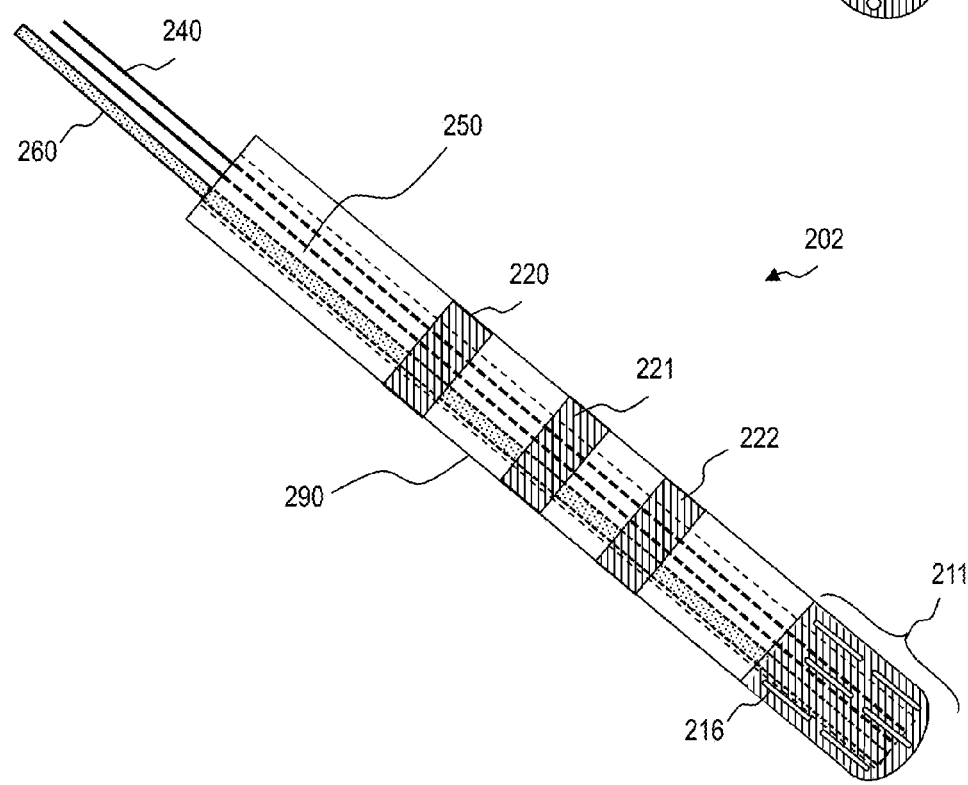
FIG. 2B is an enlarged longitudinal isometric view of the distal region of an ablation tip unit 202, wherein ablation tip unit 202 has rectangular slit apertures 216, according to some embodiments of the present invention.

FIG. 2B is an enlarged longitudinal cross-section view of the distal region of an ablation tip unit 202, which includes irrigated ablation electrode 211 having slit openings 216, according to some embodiments of the present invention. In some embodiments, ablation tip unit 202 includes the same features as ablation tip unit 201 of FIG. 2A, except for using slit openings 216 for emitting fluid rather than the circular openings 215 used for unit 201.

FIG. 3A and FIG. 3B are different cross-sectional views of an ablation electrode 301 according to some embodiments of the present invention, and FIG. 3C is an isometric view of insert 320 used in ablation electrode 301. FIG. 3A is a cross-sectional view along a longitudinal axis of irrigated ablation electrode 301. FIG. 3B is a cross-sectional view in a plane perpendicular to longitudinal axis of irrigated ablation electrode 301. FIG. 3C is an isometric view of an insert 320 suitable for location within irrigated ablation electrode 301. Collectively, these figures describe an embodiment of the present invention that meets the size requirements of what is known to those skilled in the art as an "8 French, 5 millimeter" (i.e., 2.66-mm diameter, 5-mm length) irrigated ablation electrode assembly, used in some embodiments of the present invention. In other embodiments, other diameters and lengths for the irrigated electrode assembly are used and are within the scope of the present invention while still preserving the inventive features of reduced fluid flow, broader electrode temperature operating range, more uniform electrode shell temperature and increased electrode temperature responsiveness to thermal transients during cardiac ablations.

As shown in FIG. 3A, the exterior structure of ablation electrode assembly 301 includes shell 310, tube 312, bottom plate 314, top plate 316 and delivery tube 318. In some embodiments, shell 310 is constructed of a uniform, thin layer of a material which is electrically and thermally conductive. In various embodiments, shell 310 includes gold, platinum, silver, iridium, copper, steel, aluminum, brass and/or palladium as well as composites, alloys, layers, mixtures, coatings and the like, of these materials. In some embodiments, shell diameters are in a range from about 0.015 to about 0.5 inches (about 0.381 to about 12.7 mm), inclusive, and in some embodiments, preferably in a range of 0.040 to 0.131 inches (1.016 to 3.327 mm), inclusive. In some embodiments, shell lengths are in a range of about 0.020 to about 1.0 inches (about 0.508 mm to 25.40 mm), inclusive, and in some embodiments, preferably from 0.080 to 0.5 inches (about 2.032 mm to 12.7 mm), inclusive. In some embodiments, material wall thickness is in a range of about 0.0001 to 0.0125 inches (about 2.54 microns to about 317.5 microns), inclusive, preferably from 0.001 to 0.010 inches (25.4 microns to 254 microns), inclusive. The shell is generally manufactured from a cup having cylindrical side wall 312 and distal plate 314 to which is affixed a proximal plate 316 with joint 315. In some embodiments, top plate 316 is joined to fluid delivery tube 318 with joint 319.

In some embodiments, shell 310 has small through apertures 308 that connect the interior and exterior surfaces of shell 310 to allow fluid to pass therethrough to the shell's exterior surfaces from internal passageways. Aperture geometry is any suitable shape; in some embodiments, each of a plurality of apertures has an aspect ratio of at least three (where three is to be understood as a 3:1 ratio of length to width) to provide a higher fluid-pressure drop across the aperture than occurs with lower aspect-ratio apertures, but in some other embodiments, each aperture is circular for ease of manufacturing. Rectangular, triangular, crescent and semicircular shapes are also used in other embodiments, and are within the scope of some embodiments of the present invention, some of which are shown in FIG. 21. In some embodiments, circular-aperture diameters are in the range of about 0.0001 inches to 0.050 inches (about 0.00254 to 1.27 mm), preferably from 0.001 to 0.015 inches (0.0254 to 0.381 mm). In some embodiments, apertures are fabricated by drilling, laser machining, punching, chemical etching or any other suitable manufacturing method. The shape and cross-sectional area of the apertures should be consistent with obtaining desirable hydraulic characteristics through the ablation electrode assembly to provide uniform fluid coverage over the entire exterior surface of the ablation electrode assembly. In some other embodiments, slit apertures are used for apertures 308, wherein the slit has a length (across the maximum distance within the slit) that is at least two-and-a-half (2.5) times its width (the inside dimension distance perpendicular to the length). In some embodiments, this length/width aspect ratio of the slit is about three (3), while in other embodiments, the length/width aspect ratio of the slit is about four (4), about five (5), about six (6), about seven (7), about eight (8), about nine (9), about ten (10) or at least ten. In some embodiments, the large aspect ratio of the slits reduces the amount of fluid flowing through the tip at a given fluid pressure as compared to using openings having the same cross-sectional flow area but having a length/width ratio of two or less (e.g., circular, square, triangular, crescent or short oval openings).

As used herein, the aspect ratio of a convex aperture is defined as the maximum linear dimension of an aperture, L, divided by the maximum linear dimension, W, in a plane perpendicular to L of the aperture at the exterior surface of the shell. As used herein, a convex aperture is an aperture for which any straight line drawn through the aperture (and not tangent to an edge or corner) meets the boundary of the aperture exactly twice; equivalently, any line segment with endpoints on the boundary passes through only interior points between its endpoints. See FIG. 21 discussed below, where for example, slit-shaped apertures 2101, 2102, 2103, 2104, 2105, and 2107 are considered convex apertures, while slit-shaped apertures 2106 and 2108 are considered non-convex apertures as that term is used herein. For non-convex apertures such as 2106 and 2108, the aspect ratio, as used herein, is defined as the length of a longest centerline divided by a maximum width of the aperture measured as the shortest straight line connecting opposite walls from any point along to the centerline.

In contrast to aperture aspect ratio that is defined by width and length, a "port aspect ratio" is defined by thickness of the shell 310 divided by aperture diameter, and an "inlet aspect ratio" is defined by dimensions of the radial cross-sectional area of inlet delivery tube 318.

In some embodiments, the aspect ratio of at least 3:1 for the apertures is selected to provide an ablation-tip fluid-pressure drop (defined as between the pressure at a location 3861 in interior fluid passageway 386 of delivery tube 312 and the pressure at a location 3081 immediately outside of shell 310) of at least 0.1 psi (689 pascals) at a fluid flow rate of no more than five (5) ml/min. In other embodiments, at fluid flow rates of no more than five (5) ml/min in each embodiment, the present invention provides an ablation-tip fluid-pressure drop of at least 0.2 psi (1379 pascals), of at least 0.5 psi (3447 pascals), of at least 1 psi (6895 pascals), of at least 2 psi (13789 pascals), of at least 5 psi (34474 pascals), of at least 10 psi (68947 pascals), or even at least 25 psi (172368 pascals).

In some embodiments, shell distal member 314 has a temperature sensor 330 disposed therein for measurement of temperature, which allows control of temperature. In some embodiments, additional temperature-sensing mechanisms are mounted to the shell and/or insert, and are within the scope of some embodiments of the present invention. For purposes of the present invention, temperature sensor is any mechanism known to one skilled in the art, including, for example, thermocouples, thermistors or resistance-temperature detectors (RTD). In some embodiments, temperature sensor 330 is joined to shell plate 314 using a suitable thermally conductive substance 332 known to one skilled in the art; in some embodiments, for example, solder, silver solder, conductive epoxies, resins and/or adhesive compounds such as STYCAST 2651-40 by Henkel, are used.

In some embodiments, insert 320 is a tubular element with inner diameter, outer diameter and length. The outer diameter defines an exterior surface and the inner diameter defines an interior surface. As shown in FIG. 3C, in some embodiments, insert 320 has grooves 321 (which form channels 380 when insert 320 is placed in shell 310) fabricated into its exterior cylindrical surface that traverse the axial length and terminate at feature 326. In some embodiments, the grooves 321 are concave. In some embodiments, each groove 321 has a triangular shape with two sides/walls 328 that meet at a line (in the cross-sectional view, shown as a point) 327 at the bottom of the groove. In some embodiments, grooves 321 are spaced uniformly around the outer circumference of the insert 320 and positioned such that the top/outer ridge at the intersection of the sides/walls of adjacent grooves of the insert forms a flat or convex surface 329 which is the outer diameter of the insert. The width dimension of flat 329 is dependent on the number and width of the grooves 321 and the circumference of the insert 320. The number of grooves 321 are in the range of two to one-hundred (2 to 100), and in some embodiments, preferably from six to thirty-four (6 to 34) grooves are used. Channel features such as depth, width and geometry are designed to yield desirable hydraulic and thermal characteristics for each fluid passageway through the ablation electrode assembly. In some embodiments, the grooves 321 have a depth (relative to a cylindrical geometrical surface at the outer diameter of insert 329 in a range of about 0.0005 to 0.100 inches (0.0127 to 2.54 mm), preferably from 0.001 to 0.060 inches (0.0254 to 1.52 mm). In some embodiments, the grooves 321 have a width in a range of 0.001 to 0.200 inches (0.0254 to 5.08 mm), in some embodiments, preferably in a range of 0.020 to 0.060 inches (0.0508 to 1.524 mm). Note than when the insert 320 is placed within shell 310, each groove 321 forms a fluid passageway (channel) 380 that carries fluid to one or more of the apertures 308. In some embodiments, the distal portion of insert 320 contains an inner raised feature 324 and outer raised feature 326 that collectively form annular channel 382. In some embodiments, the annular channel is further subdivided by additional raised features to provide one channel for each aperture 308 in shell bottom plate 314. In some embodiments, raised annular-ridge feature 326 has openings/channels 331 which connect the distal-end fluid passageway in conjunction with channel 382 with sidewall fluid passageway 380 of FIG. 3B. In some embodiments, the proximal surface of insert 320 is smooth without surface features although, in other embodiments, further features are added, and are within the scope of the present invention. For example, in some embodiments, it is desirable to add channels similar to those on the distal surface to enhance overall hydraulic characteristics of the fluid passageways through the ablation electrode assembly.

In some embodiments, the insert 320 is constructed preferably of low-density materials to minimize the thermal mass of an ablation electrode. In some embodiments, insert 320 is constructed of a plurality of materials (e.g., in some embodiments, outer material 322 and inner material 323 of FIG. 3B). In some embodiments, for example, insert 320 includes polymer plastics or closed-cell foam materials including, but not limited to, high density polyethylene (HDPE), polyimides, polyesters, polyethylenes, polypropylenes, polyethylene terephthalate, polyetheretherketones (PEEK), plastics under trade names such as Teflon®, Delrin®, Styrofoam®, and PEEK, as well as blends and mixtures thereof. It is important that the outer section 322 of the insert 320 have good machine-ability or fabrication characteristics to precisely and easily form critical features into its surfaces. In some embodiments, higher-density materials, such as metals or polyetheretherketones, may be preferable, but in some such embodiments, its volume should be minimized to maintain as a low thermal mass as possible. In some embodiments, a second material 323 of FIG. 3B is added, which fills a majority of the volume of the insert with a lower-density material, reducing the overall thermal mass of insert 320. For example, in some embodiments, insulating materials with a density ranging from 0.005 to 3.0 g/cm$^3$ are used, preferably from 0.05 to 1.0 g/cm$^3$. Insert 320 has an internal passageway (e.g., central through-hole) 338 through which wiring 336 and other optional materials pass therethrough to catheter shaft 110. In some embodiments, hole 338 is filled with flexible material 334, such as an adhesive or silicone sealant, to seal the hole from fluid communication with passageway 386.

In some embodiments, insert 320, is positioned within shell 310 such that distal features 326 and 324 are in contact with the interior surface of distal shell plate 314. Channel apices 329 and feature 326 are in contact with interior surfaces of shell cylinder 312. Groove 321 of inset 310 in conjunction with the interior surface of shell 310 form fluid channel 380. Surface 325 in conjunction with top plate 316 and cylindrical side 312 form fluid plenum 384 in fluid communication with interior fluid passageway (also sometimes called delivery tube fluid channel) 386 of delivery tube 312 and fluid channels 380. Surface 326 in conjunction with shell plate 314 and shell cylinder 312 form fluid channels 382. In some embodiments, insert 320 is rotationally aligned with reference to apertures 308 so each aperture 308 is centered within a designated fluid channel 380. In some embodiments, each fluid channel 380 is aligned with one aperture 308, although multiple apertures 308 per fluid channel 380 are used in some embodiments of the present invention. In other embodiments, a plurality of fluid channels are used to supply fluid to a single aperture 308 (such as a slit oriented circumferentially or helically).

In operation, coolant flows from fluid reservoir 140 (See FIG. 1) through fluid pump 130 through catheter 190 to fluid passageway 386. In some embodiments, fluid passes into fluid plenum 384 into fluid channels 380 and exits the electrode assembly through apertures 308. Active cooling on both the interior and exterior surfaces of shell 310 provides efficient use of fluid and reduces to the lowest quantity possible the volume of fluid required to maintain the shell operating temperature below the temperature that would result in blood coagulation. In some embodiments, the present invention decreases fluid flow rates from a conventional range of eight to thirty (8-30) ml/min to a range of two to ten (2-10) ml/min without formation of blood coagulum or cauterization of tissue in contact with the exterior surfaces of electrode shell 310. In some embodiments, flow rates of 1 ml/min at clinically relevant ablation parameters are used with the present invention. In addition, the multiplicity of narrow fluid channels 380 combined with long channel length creates a high hydraulic-pressure drop through the ablation electrode assembly, which creates a potentially significant hydraulic force on particles that may be temporarily trapped in one or more of the apertures 308 in the shell during an ablation, such as by particles of endocardial fat, residual tissue, biological fragments, blood components (including clots), denatured proteins or other particulate contamination. As flow is reduced through the apertures 308 by a blockage, fluid hydraulic pressure at the aperture increases toward that in fluid plenum 384, thus increasing the hydraulic force on the trapped particle to expel it from the aperture. It is anticipated that pressures ranging from 0.10 to 10 psig (689 to 68,947 pascals) can be attained at fluid plenum 384 and that higher pressures up to 25 psi (172,368 pascals) or more are possible.

In addition, the use of low-density materials in the insert 320 reduces the quantity of energy required to cause a rise in shell temperature as measured by a temperature sensor attached to the electrode shell. Reductions in thermal capacitance from a range of 0.7 to 1.1 Joule/C for conventional ablation electrodes to a value for the present invention of 0.30 Joules/C are possible with the present invention. In some embodiments, the benefit of reduced thermal capacitance is a more rapid response of a temperature sensor to localized heating in a shell or tissue. Once a temperature sensor records a temperature higher than the RF generator set point, RF power is decreased in order to lower the electrode temperature. Having a temperature sensor that responds more quickly to thermal aberrations reduces the degree of temperature overshoot, which also reduces the likelihood of tissue charring and possibly perforations of vessels, as well as reducing coagulum formation on the electrode shell.

FIGS. 4A through 4F are sectors from a perpendicular cross-sectional view of various embodiments of a shell 310, which illustrate different embodiments of inserts that, together with shell 412, form fluid passageways (i.e., 480, 481, etc.) of the present invention that correspond to fluid channels 380 of FIG. 3A and FIG. 3B described above.

FIG. 4A illustrates a portion of an ablation-tip unit 401 that has a plurality of rectangular fluid passageway 480 formed by shell 412 and insert 422, in which each channel 480 is formed by side surfaces 428 and bottom surface 427.

FIG. 4B illustrates a portion of an ablation-tip unit 402 that has a plurality of outer triangular passageways 481 and a plurality of inner triangular channels 482 formed by shaping a thin corrugated material 432 in a lineal pattern of contiguous alternating triangular shapes. The shaped material 432 is inserted between shell 412 and insert 423 to form fluid passageway 481 between surfaces of corrugated material 432 and shell 412 and fluid passageway 482 between the surfaces of corrugated material 432 and insert 422.

FIG. 4C illustrates fluid passageways using a portion of an ablation-tip unit 403 that has a plurality of fluid passageways formed from circular segments. Flat surfaces 434 are formed on the exterior surface of insert 424, which in conjunction with the interior surface of shell 412 form fluid passageway 483.

FIG. 4D illustrates a portion of an ablation-tip unit 404 that has a plurality of fluid passageway with no channels. Fluid passageway 484 is formed by the interior surface of shell 412 and the exterior surface of cylindrical insert 423, which has a smooth exterior containing no external-surface geometric channel patterns.

FIG. 4E illustrates a portion of an ablation-tip unit 405 that has a plurality of semi-circular fluid passageways. Channels 436 are each an arc of a circle formed into the exterior surface of insert 425 which, when coupled with the inside surface of shell 412 form fluid passageway 485.

FIG. 4F illustrates a portion of an ablation-tip unit 406 that has a plurality of triangular fluid passageways which use a second material to form a fluid passageway. Triangular channels 438 are formed into the exterior surface of insert 426 which, when coupled with the inside surface 414 form fluid passageway 486. In some embodiments, layer 414 is deposited as a coating on the interior surface of shell 412 before inserting insert 426. In some embodiments, layer 414 is a separate material. In some embodiments, layer 414 is omitted.

FIGS. 5A thru 5E illustrate flat plan views of the circumferential surfaces of alternate geometric configurations for fluid channels formed in the exterior surface of an insert. Such patterns may be advantageous to provide a more constant fluid pressure loss along the interior surfaces of a shell in order to obtain a more uniform distribution of flow though the apertures.

FIG. 5A is a plan view of the circumferential surface of an insert 501 having an longitudinal pattern in which each fluid channel has one vertical channel 580, a U-shaped channel 581 and another vertical channel 584 in which fluid enters at the top of the insert 501 and travels longitudinally to the bottom and then makes a U-turn traveling longitudinally back towards the top of the insert until the channel ends near the top.

FIG. 5B is a plan view of the circumferential surface of an insert 502 having a plurality of fluid channels 582 formed into the surface of insert 522 configured in a helical or spiral pattern with a central outer-surface longitudinal feeder channel 583.

FIG. 5C is a plan view of the circumferential surface of an insert 503 having a plurality of fluid channels 590 formed into insert 522 which are supplied from a central horizontal circumferential feeder 587 at the longitudinal center of the insert constructed of a central outer-surface longitudinal (vertical) feeder channel 586 and central circumferential (horizontal) feeder 587.

FIG. 5D is a plan view of the circumferential surface of an insert 504 having a plurality of tapered fluid channels 588, which, in plan view, each have a larger width at the entry (top) of the channel and a smaller width at the end (bottom) of the channel 588.

FIG. 5E is a plan view of the circumferential surface of an insert 505 having a plurality of short fluid channels 591 formed in the surface of insert 522, which are not continuous channels but contain a central plenum 592 which acts as circumferential fluid reservoir from which fluid enters and leaves the fluid channels.

Figure 6A:
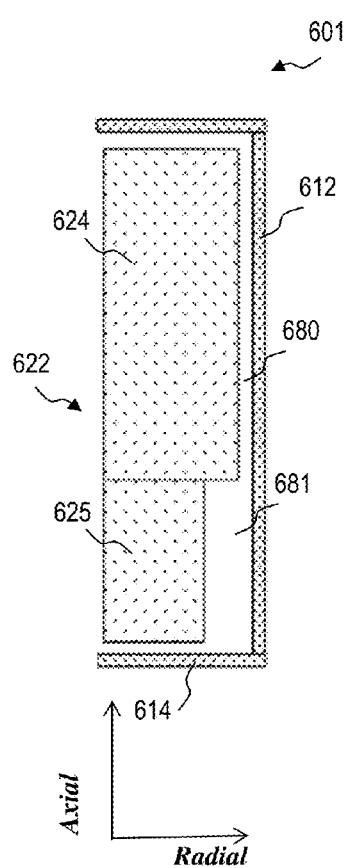
FIG. 6A is an outer segment (i.e., one-half) of a longitudinal cross-sectional view of an ablation tip 601 using an insert 622 having a first alternate outside fluid-channel profile, according to some embodiments of the invention.
Figure 6B:
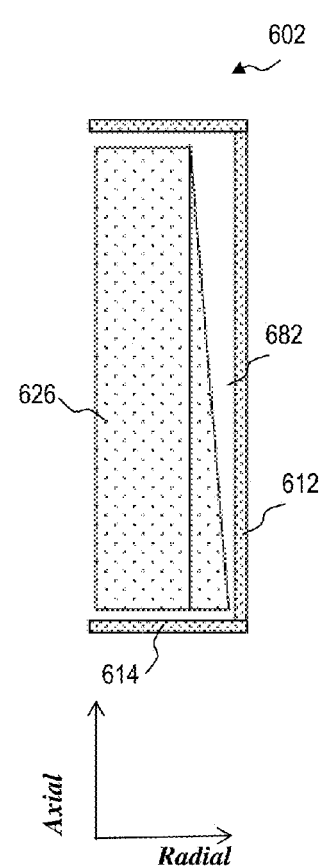
FIG. 6B is an outer segment (i.e., one-half) of a longitudinal cross-sectional view of an ablation tip 602 using an insert 626 having a first alternate outside fluid-channel profile, according to some embodiments of the invention.
Figure 6C:
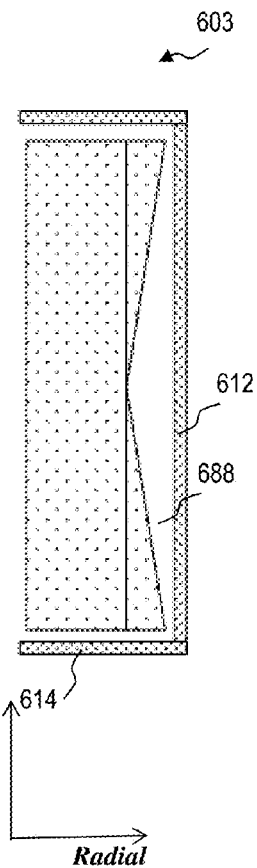
FIG. 6C is an outer segment (i.e., one-half) of a longitudinal cross-sectional view of an ablation tip 603 using an insert 628 having a first alternate outside fluid-channel profile, according to some embodiments of the invention.

FIGS. 6A thru 6C are partial longitudinal-radial cross-sectional views of the tip of embodiments of ablation electrode assembly 170 along the axis of the tip, which illustrate fluid channels having varied channel depth along the length of the insert. Such patterns may be advantageous to provide a more constant hydraulic pressure loss along the interior surfaces of a shell in order to obtain a more uniform distribution of flow though the apertures.

FIG. 6A is the right-hand half of a cross-sectional view of a portion of an ablation-tip unit 601 that has a plurality of fluid channels 680-681 which each have a step change in depth. In some embodiments, insert 622 is formed by proximal portion 624 and distal portion 625, wherein proximal portion 624 has a larger radial dimension. When coupled with interior surface of shell 612, narrower fluid channels 680 are created near the fluid-entry (top) portion of the tip, and larger channels 681 near the bottom portion of the tip.

FIG. 6B is the right-hand half of a cross-sectional view of a portion of an ablation-tip unit 602 that has a plurality of fluid channels 682, wherein the depth of each channel 682 varies continuously in the longitudinal (parallel to the axial) direction. Insert 626 has a smaller radius at the fluid-entry (top) of the tip and a larger radius at the end (bottom). When coupled with the inside surface of shell 612, a fluid channel whose gap varies continuously in depth along its length is created.

FIG. 6C is the right-hand half of a cross-sectional view of a portion of an ablation-tip unit 603 that has a plurality of fluid channels within a tip, wherein each channel 688 varies in depth both toward the proximal (top) end and toward the distal (bottom) end. In some embodiments, the largest depth of each channel 688 occurs nearest the longitudinal (parallel to the axial direction) center of the tip. In some embodiments, this design is combined with fluid channels described in FIG. 5C to create a fluid passageway which varies in both the axial and circumferential directions.

Figure 7A:
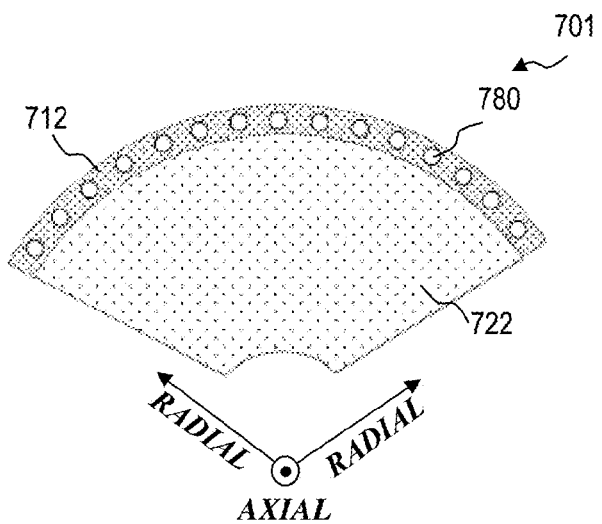
FIG. 7A is a segment of a radial cross-sectional view of cooling means integrated into the electrode shell using small axial tubes.
Figure 7B:
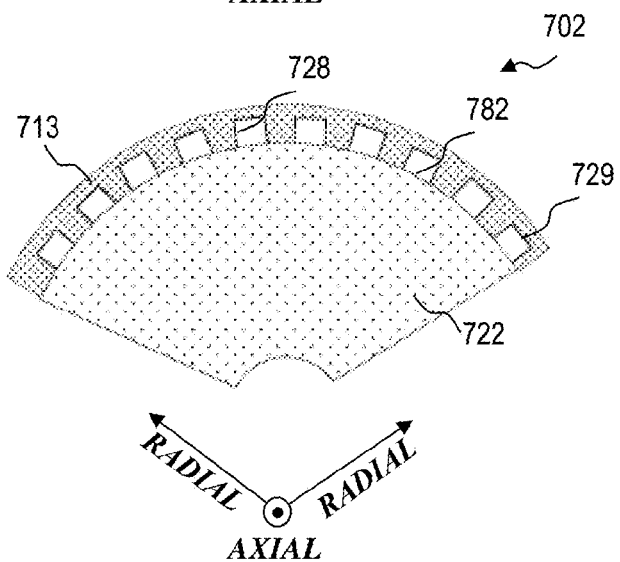
FIG. 7B is a segment of a radial cross-sectional view of cooling means integrated into the electrode shell using integral fins.
Figure 7C:
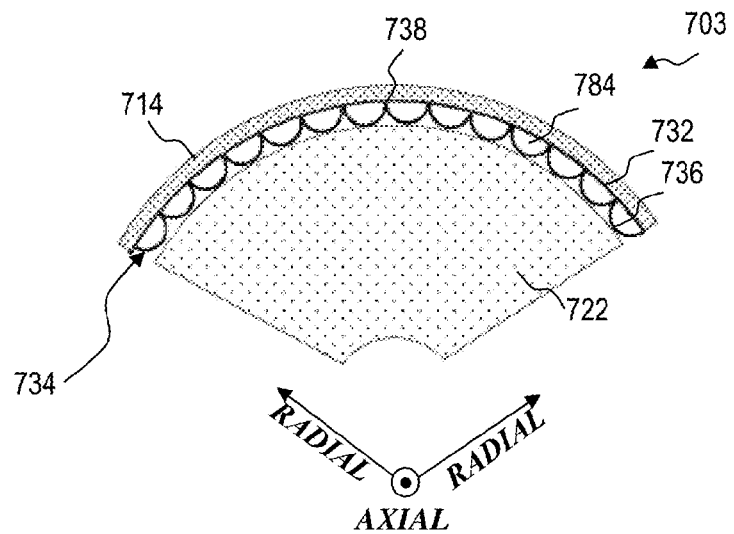
FIG. 7C is a segment of a radial cross-sectional view of cooling means integrated into the electrode shell using heat-exchanger tubular construction.

FIGS. 7A, 7B and 7C are sectors from cross-sectional views of ablation tips that use different embodiments for shell 310, illustrating channels which are contained within, or on the inner face, of cylindrical wall 312 of shell tip 310. These designs have the potential advantage of providing more direct and efficient cooling of a shell tip.

FIG. 7A illustrates a portion of an ablation-tip unit 701 that has a plurality of tubular channels 780 formed within shell 712 and which uses a cylindrical insert 722. In some such embodiments, circular-cross-section tubes 780 are contained within shell 712.

FIG. 7B illustrates a portion of an ablation-tip unit 702 that has a plurality of rectangular channels 782 formed by grooves on the inner surface of shell 713, the grooves having sides 728 and bottoms 729 wherein fluid passageways 782 are bounded at their inner radius by the exterior cylindrical surface of insert 722 and the interior surface of shell 713.

FIG. 7C illustrates a portion of an ablation-tip unit 703 that has a plurality of fluid channels 784 formed by a shell 714 made from a flat plate heat exchanger 734 rolled into a cylinder with a cross-section having a circular profile. In some embodiments, the heat exchanger is made of a thin flat plate 732 and scalloped thin plate 736 in which are formed a plurality of semicircular-groove profiles in a continuous manner. In some embodiments, the two sheets are attached at joints 738 at the ridge tip between adjacent scallops to form individual fluid passageways 784. In some embodiments, the heat exchanger assembly is placed in contact with the interior surface of shell 714 and the exterior cylindrical surface of insert 722. Heat exchanger materials are selected from a similar list of materials suitable for making tip shell 714.

FIG. 8A, FIG. 8B and FIG. 8C are different views of an ablation electrode tip 801 according to another embodiment of the present invention.

FIG. 8A is a cross-sectional view along the longitudinal axis of an irrigated ablation electrode 801.

FIG. 8B is a cross-sectional view perpendicular to longitudinal axis of an irrigated ablation electrode 801.

FIG. 8C is an isometric view of an insert 803 that will be located within an irrigated ablation electrode 801 of FIG. 8A. Collectively, these figures describe an embodiment of the present invention that meets the size requirements of what is known to those skilled in the art as an "8 French, 5 millimeter" (2.66-mm diameter, 5-mm length) irrigated ablation electrode assembly. It is contemplated that any suitable diameter and length for the irrigated electrode assembly is equally feasible and technically possible within the scope of the present invention while still preserving the inventive features of reduced fluid flow, broader electrode temperature operating range, more uniform electrode shell temperature and increased electrode temperature responsiveness to thermal transients during cardiac ablations.

As shown in FIG. 8A, ablation electrode assembly 801 includes shell 810 that has a cylindrical tube 812, bottom plate 814, top plate 816 and delivery tube 818. In some embodiments, the shell 810 is constructed of a uniform, thin layer of a material which is electrically and thermally conductive, wherein various embodiments include, but are not limited to, gold, platinum, silver, iridium, copper, steel, aluminum, brass and palladium as well as composites, mixtures and coatings of these materials. In some embodiments, shell diameters are in the range of 0.015 to 0.50 inches (0.381 to 12.7 mm), inclusive, preferably from 0.040 to 0.131 inches (1.016 to 3.327 mm), inclusive. In some embodiments, shell lengths are within a range from 0.02 to 1.0 inches (0.508 to 25.4 mm), preferably from 0.080 to 0.5 inches (2.032 to 12.7 mm). In some embodiments, material-wall thicknesses are in the range of 0.0001 to 0.0125 inches (2.54 to 317.5 microns), inclusive, preferably from 0.001 to 0.010 inches (25.4 to 254 microns), inclusive. In some embodiments, the shell is generally manufactured from a cup containing cylindrical side wall 812 and distal plate 814, to which is affixed proximal plate 816 with joint 815. In some embodiments, fluid delivery tube 818 is joined to top plate 816 with joint 819.

Shell 810 contains small apertures 808 which connect the interior and exterior surfaces of the shell for purpose of allowing fluid to pass therethrough to the exterior surfaces of shell 810. Aperture geometry can be any shape but, in some embodiments, is circular for ease of manufacturing. Rectangular, triangular, crescent and hemispherical shapes are also used in some embodiments of the present invention, some of which are shown in FIG. 21. Circular aperture diameters are in the range of 0.0001 to 0.050 inches (0.00254 to 1.27 mm), preferably from 0.001 to 0.015 inches (0.0254 to 0.381 mm). Apertures can be fabricated by drilling, laser machining, punching, chemical etching or any other suitable manufacturing method. In some embodiments, the shape and cross-sectional area of the apertures are consistent with obtaining desired hydraulic characteristics through the ablation electrode assembly as explained in detail later and providing uniform coverage of fluid over entire exterior surface of the ablation electrode assembly.

In some other embodiments, slit apertures are used for apertures 808, wherein the slit has a length (across the maximum distance within the slit) that is at least two-and-a-half (2.5) times its width (the inside dimension distance perpendicular to the length). In some embodiments, this length/width aspect ratio of the slit is about 3, while in other embodiments, the length/width aspect ratio of the slit is about 4, about 5, about 6, about 7, about 8, about 9, about 10 or more than ten (see discussion of FIGS. 21A-21H below). In some embodiments, the large aspect ratio of the slits reduces the amount of fluid flowing through the tip at a given fluid pressure as compared to using openings having the same cross-sectional opening area but having a length/width ratio of two or less (e.g., circular, square, triangular, crescent or short oval openings).

Shell distal member 814 has a temperature sensing means 830 disposed therein for measurement of temperature, which allows control of temperature. Additional temperature-sensing mechanisms can be mounted to the shell or insert within the scope of some embodiments of the present invention. For purposes of the present invention, the temperature sensing means can be any mechanism known to one skilled in the art, including, for example, thermocouples, thermistors or RTD's. In some embodiments, the temperature-sensing means 830 is joined to shell plate 814 using thermally conductive material 832 known to one skilled in the art, for example, solder, silver solder, conductive epoxies, resins or adhesive compounds such as STYCAST 2651-40 by Henkel, is used.

In some embodiments, insert 820 is a tubular element with an inner diameter that defines its central fluid channel, and an outer diameter and length. As shown in FIG. 8C, insert 820 has external protuberances 821 affixed or formed at discrete separated locations over the entire cylindrical exterior surface of the insert. In some embodiments, the protuberances have a rectangular geometry in cross-section defined by a width, w, and length, l, and a height, h, defined by the distance the protuberance extends above the innermost exterior surface of the insert. Protuberances 821 are spaced around the outer circumference of the insert and positioned such that the center opening 882 through the protuberance 821 aligns with apertures 808 in the shell 810. In some embodiments, the dimensions of the protuberances are dependent on the number of apertures in the shell. In some embodiments, the number of protuberances are in the range of two (2) to eighty (80), preferably from six (6) to thirty-four (34). In some embodiments, the height of the protuberances are in the range of 0.0005 to 0.250 inches (0.0127 mm to 6.35 mm), preferably from 0.001 to 0.015 inches (0.0254 to 0.381 mm). In some embodiments, protuberance width and length are in the range of 0.010 to 0.100 inches (0.254 to 2.540 mm), preferably from 0.025 to 0.075 inches (0.635 to 1.905 mm). The distal portion of the insert contains an inner raised feature 824 which surrounds through-hole 838. In some embodiments, outer raised features 826 are located at the distal end of insert 820 which contains hole 831. The proximal surface of insert 820 is smooth without surface features, although in some embodiments, features can be added within the scope of the present invention. For example, it may be desirable to add features to facilitate the movement of fluid to the outside surface of the insert. Insert 820 contains a central hole 838, through which wiring 834 and 836 and optionally other structures or materials pass to catheter shaft 110. Central hole 838 forms fluid passageway 884 which is in fluid communication with space 880 via fluid passageway 882 to connect the exterior surface of the protuberance with the interior passageway of the insert. Preferably each fluid passageway is aligned with a single aperture. Preferably the diameter and/or shape of the aperture are selected to provide the desired hydraulic characteristics to the fluid passageway through the electrode assembly. In some embodiments, the passageways and apertures have a circular geometry to for ease of manufacture. In some embodiments, passageway and aperture diameters are in the range of 0.0001 to 0.050 inches (0.0025 to 1.270 mm), preferably from 0.0005 to 0.015 inches (0.0127 to 0.381 mm). In some embodiments, the thickness of an insert, defined as the outer diameter of a protuberance 821 minus the inner diameter of hole 838, then divided by two, for an 8 French diameter electrode, ranges from 0.010 to 0.045 inches (0.254 to 1.143 mm), preferably from 0.015 to 0.030 inches (0.381 to 0.762 mm). In some embodiments, the dimensions of the fluid passageways are designed to give a fluid passageway length to hydraulic diameter ratio, L/d, ranging 1 to 500 preferably 3 to 100 inclusive, and pressure drop across individual fluid passageways ranging from 0.05 to 20 psi (about 345 to 137,895 pascals).

In some embodiments, the insert 820 is constructed of one or more low-density materials to minimize its thermal capacitance, for example solid polymers or closed-cell polymer-foam materials including, for example, the materials listed above for insert 320 of FIGS. 3A, 3B, and 3C, and/or fabrication characteristics to precisely and easily form critical features into its surfaces and to fabricate fluid passageway into its core. Preferably the lowest-density material exhibiting the desired manufacturability is chosen—for example, PEEK. In some embodiments, the density of the insert material ranges from 0.005 to 3.0 $g/cm^3$, preferably from 0.05 to 1.0 $g/cm^3$.

In some embodiments, insert 820 is positioned within shell 810 such that distal features 826 and 824 are in contact with the interior surface of distal shell plate 814 and protuberances 821 are in contact with interior surfaces of shell cylinder 812. The space formed by the interior surface of the shell and external surface 828 of the insert form fluid reservoir 880 and 888 which are in fluid communication with space 884. Insert top surface 825 in conjunction with shell top plate 816 and shell cylindrical side 812 form fluid plenum 864 in fluid communication with interior spaces 880, 884 and 888. In addition, since insert protuberances 821 do not form a liquid seal, each passageway 882 is fluid coupled to fluid reservoirs 880 and 888 via a narrow fluid gap. In some embodiments, the fluid reservoir has a width, defined as the radial distance between the inner surface of the electrode shell and the most distant surface of the insert, ranging from about 0.0005 to 0.030 inches (0.127 to 0.76 mm), preferably from 0.003 to 0.010 inches (0.051 to 0.025 mm).

In operation, coolant flows from fluid reservoir 140 through fluid pump 130 through catheter 190 to fluid passageway 886. Fluid passes into fluid passageway 864 into spaces 880 and 888 providing a fluid reservoir in direct contact with the interior surface of the shell. Fluid passes into fluid passageway 884 and into passageways 882 and exits the electrode assembly through apertures 808 providing active cooling of the exterior surfaces of shell 810. The use of fluid on both the interior and exterior surfaces of the electrode reduces the volume of fluid required to maintain the shell operating temperature below that required for blood coagulation. It is anticipated that this design will decrease fluid flow rates from a range of 8-30 ml/min to a range of 2-8 ml/min without formation of blood coagulum or cauterization of tissue on exterior surfaces of an electrode shell. Flow rates of 5 ml/min at clinically relevant ablation parameters should be possible within the scope of the present invention.

In an embodiment for an electrode having a 2.66-mm outer diameter with a 5 mm axial length, with a shell-wall thickness of 0.005 inches (0.127 mm), with an fluid reservoir gap of 0.010 inches (0.254 mm), and an insert thickness of 0.030 inches (0.76 mm) with circular fluid passageway and aperture diameter of 0.005 inches (0.127 mm), $L/d_h$ of 6 is achieved, which has a theoretical fluid pressure drop of approximately 0.09 psi (620.5 pascals). In another embodiment, the fluid passageway and aperture diameters is 0.002 inches giving an $L/d_h$ of 12 which has a theoretical fluid pressure drop of about 4.2 psi (28,958 pascals) for 28 holes at 5 ml/min.

Figure 9A:
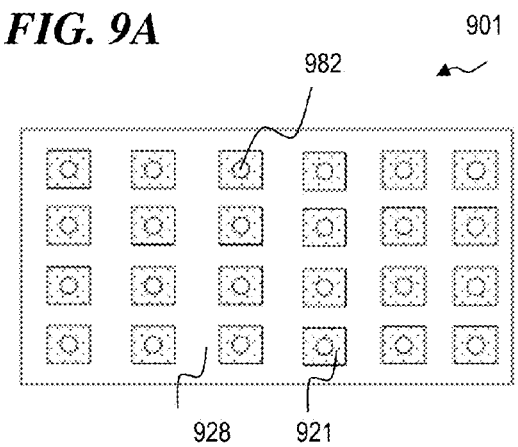
FIG. 9A is a plan flattened view of the exterior surface of an insert 901, according to some embodiments of the present invention.
Figure 9B:
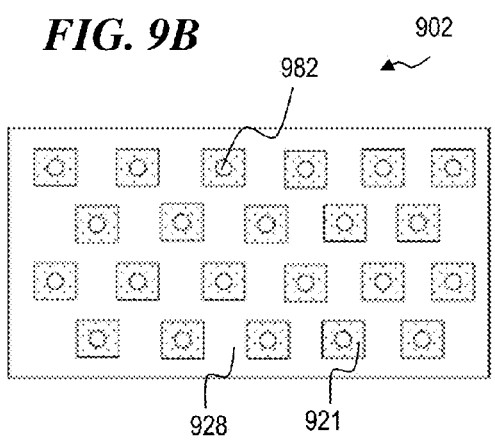
FIG. 9B is a plan flattened view of the exterior surface of an insert 902, according to some embodiments of the present invention.
Figure 9C:
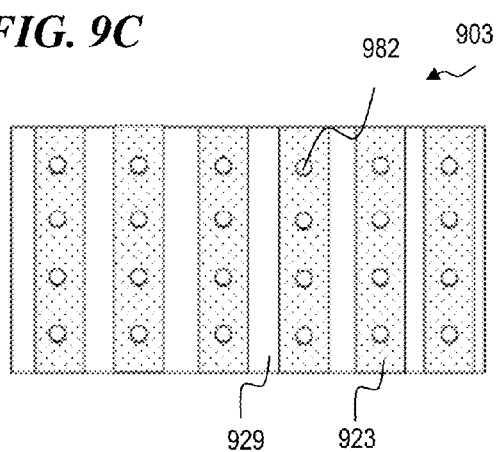
FIG. 9C is a plan flattened view of the exterior surface of an insert 903, according to some embodiments of the present invention.
Figure 9D:
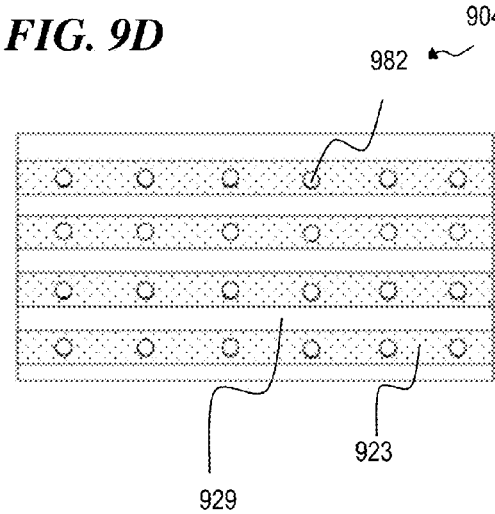
FIG. 9D is a plan flattened view of the exterior surface of an insert 904, according to some embodiments of the present invention.
Figure 9E:
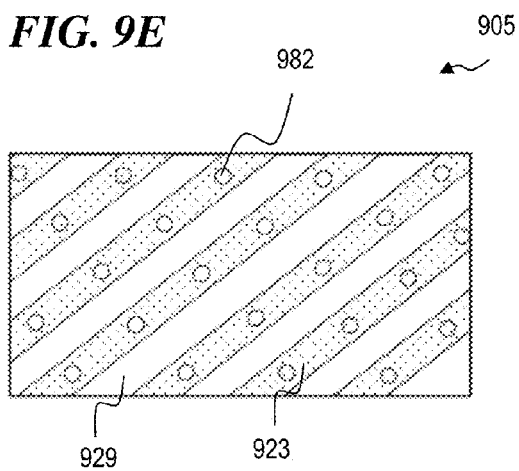
FIG. 9E is a plan flattened view of the exterior surface of an insert 905, according to some embodiments of the present invention.

FIGS. 9A through 9E are plan flattened views of the circumferential outer surface of various embodiments of an insert 820 illustrating different geometric patterns for the arrangement of protuberances on the exterior surface of an insert. Such arrangements are potentially beneficial in providing a more-uniform layer of fluid in contact with the inside surface of tip shell 810 while simultaneously minimizing the volume of water contained within shell tip 810. Such features potentially have a more-uniform shell wall temperature and lower tip thermal capacitance, which can reduce incidence of thrombus formation and more quickly respond to tissue overheating. FIG. 9A shows insert surface 901 and FIG. 9B shows insert surface 902 each with individual protuberances 921 surrounding each fluid passageway 982. The recessed areas below the protuberances form insert surfaces 928 which are in direct fluid contact. FIG. 9A shows the centers of each protuberance arranged in a rectangular pattern while FIG. 9B shows a triangular pattern. FIG. 9C shows insert surface 903, FIG. 9D shows insert surface 904 and FIG. 9E shows insert surface 905, each with protuberances 923 that provide outlets for fluid channels 982 from a raised bar of material that extends above the recessed surfaces 929 and contain several fluid passageways 982. The recessed areas below the protuberances form insert surfaces 929 which are in direct fluid contact. FIG. 9C shows an arrangement of raised bars with fluid passageways aligned axially (parallel to the central longitudinal axis of the insert). FIG. 9E shows an arrangement of raised bars with fluid channels arranged in a spiral, with each groove at 45 degrees to a line parallel to the central longitudinal axis of the ablation electrode tip. Other geometric patterns are possible and fall within the scope of the present invention.

FIGS. 10A and 10B are different views of an ablation electrode according to another embodiment of the present invention. Collectively, these figures describe one embodiment of what is known to those skilled in the art as an "8 French, 5-millimeter" (2.66-mm diameter, 5-mm length) irrigated ablation electrode assembly. It is contemplated that any diameter and length for the irrigated electrode assembly is equally feasible and technically possible within the scope of the present invention while still preserving the inventive features of reduced fluid flow, broader electrode temperature operating range, more uniform electrode shell temperature and increased electrode temperature responsiveness to thermal transients during cardiac ablations.

FIG. 10A is a cross-sectional view along the longitudinal axis of an irrigated ablation electrode 1001. FIG. 10B shows a cross-sectional view perpendicular to the longitudinal axis of irrigated ablation electrode 1001. As shown in FIG. 10A, the exterior structure of ablation electrode assembly 1001 includes shell 1010, which includes cylindrical tube 1012, distal plate 1014, top plate 1016 and delivery tube 1018. The shell 1010 is constructed of a uniformly thin layer of a material which is electrically and thermally conductive. In some embodiments, shell 1010 includes but is not limited to gold, platinum, silver, iridium, copper, steel, aluminum, brass and palladium as well as composites, mixtures and coatings of these materials. The diameter of shell 1010 are in a range of 0.015 to 0.50 inches (0.381 to 12.70 mm), and is preferably in a range of 0.040 to 0.131 inches (1.016 to 3.327 mm) inclusive. The length of shell 1010 can be in a range of 0.020 to 1.000 inches (0.508 to 25.4 mm), and is preferably in a range of 0.080 to 0.400 inches (2.032 to 10.16 mm) inclusive. The wall thickness of shell 1010 can be in a range of 0.0001 to 0.0125 inches (0.0025 to 0.317 mm), and is preferably in a range of 0.001 to 0.010 inches (0.0254 to 0.254 mm) inclusive. The shell is generally manufactured from a cup containing a side wall 1012 and distal plate 1014 to which is affixed proximal plate 1016 with joint 1015. In some embodiments, fluid delivery tube 1018 is joined to top plate 1016 with joint 1019.

Shell 1010 contains small apertures 1008 that allow fluid to pass therethrough to the exterior surfaces of shell 1010. Aperture geometry can be any shape, but, in some embodiments, is circular for ease of manufacturing. Rectangular, triangular, crescent and hemispherical shapes are also anticipated within the scope of the present invention, some of which are shown in FIG. 21. Circular aperture diameters are in the range of 0.0001 inches to 0.050 inches (0.00254 to 1.270 mm), preferably from 0.001 to 0.015 inches (0.0254 to 0.0.381 mm). Apertures can be fabricated by drilling, laser machining, punching, chemical etching, 3D printing or any other suitable manufacturing method. The shape and cross-sectional area of the apertures should be consistent with obtaining the desirable hydraulic characteristics through the ablation electrode assembly to provide uniform coverage of fluid over the entire exterior surface of an ablation electrode assembly.

In some embodiments, shell distal plate 1014 has a temperature sensing means 1030 disposed therein or affixed thereon for measurement and control of temperature. Additional temperature sensing mechanisms can be mounted to the shell or insert within the scope of the present invention. For purposes of the present invention, temperature sensing means can be any mechanism known to one skilled in the art, including, for example, thermocouples, thermistors or resistance temperature detectors (RTD). The temperature sensing means 1030 is joined to shell plate 1014 using thermally conductive material 1032 known to one skilled in the art, for example, solder, silver solder, conductive epoxies, resins or adhesive compounds such as STYCAST 2651-40 by Henkel, can be used.

In some embodiments, insert 1020 is a tubular element with an inner and outer diameter and length. The exterior surface of the insert 1020 defined by its outer diameter has a smooth surface with a geometry matching that of the interior surface of the electrode shell 1010. Central lumen 1084 is in fluid communication with fluid channel 1086 of fluid delivery tube 1018. Fluid passageways 1082 extend radially to operably couple fluid to the exterior from the interior of the insert 1020. Preferably the diameter of each passageway 1082 corresponds to that of the aperture 1008 in the shell 1010 to which it is matched, although different diameters and varying cross-sectional flow areas are within the scope of the present invention. Preferably the design of the aperture 1008 and the passageway 1082 are selected to provide the desirable hydraulic characteristics for the fluid passage through the electrode assembly. In some embodiments, the passageways 1082 and apertures 1008 both have a circular geometry to for ease of manufacture. Other embodiments use slit-shaped apertures 1008. In some embodiments, passageway and aperture diameters are in the range of 0.0001 to 0.050 inches (0.0025 to 1.27 mm), preferably from 0.0005 to 0.015 inches (0.0127 to 0.38 mm). In some embodiments, the thickness of an insert, defined as its outer diameter subtracted from its inner diameter then divided by two, for a 2.4-mm-diameter electrode, are in the range of 0.010 to 0.045 inches (0.254 to 1.02 mm), preferably from 0.015 to 0.030 inches (0.38 to 0.76 mm). In some embodiments, the dimensions of the fluid passageways are designed to give a fluid-passageway length to hydraulic-diameter ratio ranging 1 to 500, preferably in a range of 3 to 100, inclusive and pressure drop across individual fluid passageways ranging from 0.1 to 20 psi (687 to 137,900 pascals), preferably greater than 0.5 psi (3,447 pascals).

The insert 1020 is constructed preferably of one or more low-density materials to minimize its thermal capacitance, including for example, the materials listed above for insert 320 of FIGS. 3A, 3B, and 3C. It is important to have good fabrication characteristics to precisely and easily form critical features into its surfaces and to fabricate fluid passages way into its core. Preferably the lowest-density material exhibiting the desired manufacturability is chosen as for example, PEEK. In some embodiments, the density of the insert material ranges from 0.1 to 3.0 g/cm$^3$, preferably from 0.3 to 1.5 g/cm$^3$.

In some embodiments, insert 1020 is positioned within shell 1010 such that the external surface of the insert is in substantial contact with the interior surface of the electrode shell 1010. The insert is rotationally aligned so that each aperture in the electrode shell is operably coupled to a fluid passageway in the insert. It is within the scope of the present invention to have more than one aperture coupled to a fluid passageway.

In operation, coolant flows from fluid reservoir 140 through fluid pump 130 through catheter 190 to fluid channel 1086. Fluid passes into fluid plenum 1084 and then into passageways 1082 and exits the electrode assembly through apertures 1080 providing active cooling of the exterior surfaces of shell 1010. It is anticipated that this design will decrease fluid flow rates from a range of 8 to 30 ml/min to a range of 2 to 8 ml/min without formation of blood coagulum or cauterization of tissue on the exterior surface of an electrode shell.

FIG. 11A is a cross-sectional view of an ablation electrode 1101 which includes shell 1120 with fluid passageways that have both vertical and horizontal components passing through insert 1122. In some embodiments, longitudinal (vertical in FIG. 11A) passageways 1182 and radial (horizontal in FIG. 11A) passageways 1183 operably couple fluid entering the passageways via of fluid plenum 1184 which is operably coupled to fluid passageways 1186 to the longitudinal axis of an ablation electrode. These fluid passageways have longer channel lengths compared to a fluid passageway which is perpendicular to the longitudinal axis thereby increasing the $L/d_h$ ratio significantly. In some embodiments the $L/d_h$ ratio can be increased by a factor of two (2). In some embodiments, the $L/d_h$ ratio can be increased by a factor of four (4). In some embodiments, the $L/d_h$ ratio can be increased by a factor greater than four (4).

FIG. 11B is a cross-sectional view of an ablation electrode 1102 which contains shell 112 with fluid passageways that are oriented at a diagonal outward angle to the longitudinal axis of an ablation electrode. Passageways 1188 pass through insert 1124 and operably couple fluid from center fluid lumen 1184 which is operably coupled to fluid passageway 1186 and apertures 1106. These fluid passageways 1188 have longer channel lengths compared to a fluid passageway which is perpendicular to the longitudinal axis, thereby increasing the $L/d_h$ ratio significantly. In some embodiments, the $L/d_h$ ratio is increased by a factor of two (2). In some embodiments, the $L/d_h$ ratio is increased by a factor of four (4). In some embodiments, the $L/d_h$ ratio can be increased by a factor greater than four (4).

Figure 12A:
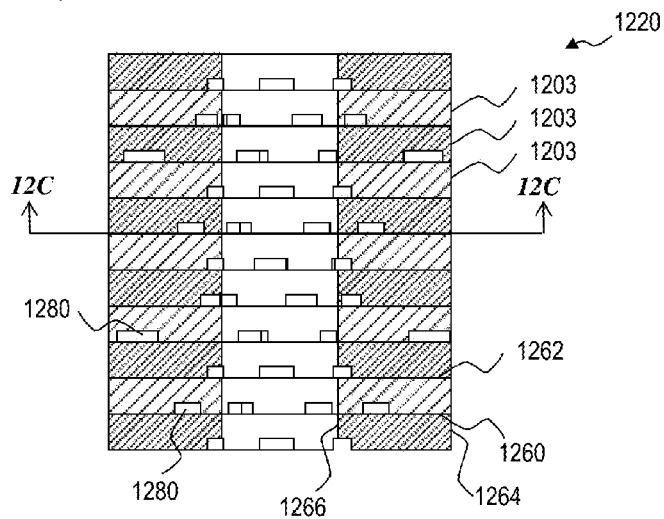
FIG. 12A is a longitudinal cross-sectional view of an insert 1220 manufactured with multiple horizontal layers of plates 1203 with grooves that form fluid channels when joined together to form the insert 1220.
Figure 12B:
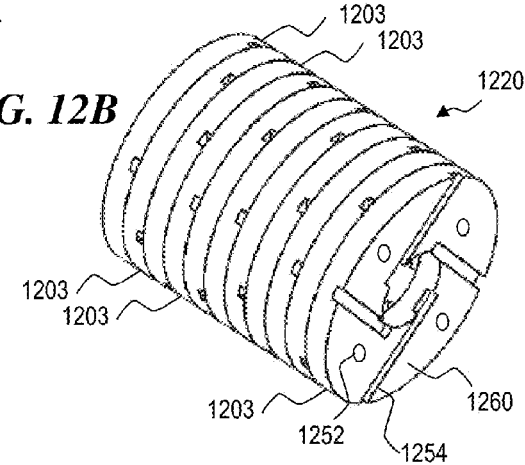
FIG. 12B is an isometric view of insert 1220.
Figure 12C:
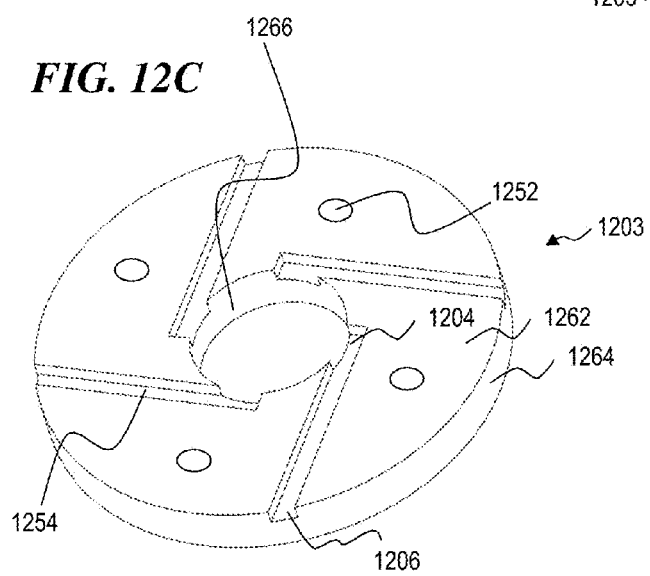
FIG. 12C is an isometric view of a plate 1203 having four grooves that form four fluid channels within the plate when used to form insert 1220.

FIGS. 12A, 12B and 12C are different views of an insert 1220 and a plate portion thereof, formed from a multiplicity of plates according to another embodiment of the present invention.

FIG. 12A is a cross-sectional view of insert 1220 along its longitudinal axis.

FIG. 12B is an isometric view of insert 1220.

FIG. 12C is an isometric view of one plate 1203 that shows the surface of a plate with channels/grooves 1254 (which form the passageways 1280 of FIG. 12A) and alignment features formed into or on one or more surfaces. In FIG. 12A, insert 1220 is constructed of plates 1203 stacked in a longitudinal direction along the axis of an electrode. Each plate 1203 has a uniform thickness with top surface 1262 and bottom surface 1260. In one embodiment, a plate has an outer diameter defining exterior surface 1264 and an inner diameter defining interior surface 1266. Other geometric shapes are possible within the scope of this invention; for example, in some embodiments, the outer geometric shape shown in FIG. 8C is formed. The inner surface could also have a non-circular cross-sectional profile to provide space for instrumentation such as, for example, fluid position sensors, force sensors or additional temperature instrumentation. Grooves 1254 are formed into one or both planar surfaces of the plate. Each groove 1254 forms fluid passageway 1280 when abutting a surface of an adjoining plate thereby connecting the interior surface 1266 to the exterior surface 1264 of a plate with port 1204 on the interior surface 1266 of the central channel of the plate and port 1206 on the external surface 1264 of the plate 1203. In some embodiments, each plate 1203 has one or more fiducial alignment features 1252 which index each plate with respect to adjacent plates. In some embodiments, each alignment feature 1252 includes an indentation on bottom surface 1260 and a matching protuberance on top surface 1262, or, for example, a hole in each plate 1203 through which a rod can be inserted from the top plate 1203 to the bottom plate 1203. In some embodiments, each alignment feature 1252 includes a protuberance, such as, for example, a pin that mates with a corresponding indentation in the neighboring plate. In some embodiments, holes are used in all plates through which rods are placed to index plates for alignment. In some embodiments, each alignment feature 1252 uses non-circular shapes. In some embodiments, alignment features included in each plate are a combination of both indentations and protuberances.

In some embodiments, plates 1203 are made of materials which are easily shaped by subtractive or additive manufacturing methods. Preferably low-density materials are selected to reduce the overall thermal capacitance of an electrode assembly. In some embodiments, for example, polymer plastics are used, including, for example, the materials listed above for insert 320 of FIGS. 3A, 3B, and 3C. In some embodiments plates are made from metals to utilize their superior subtractive-processing characteristics, for example to utilize processing methods such as chemical etching. Suitable metals include but are not limited to copper, brass, aluminum, stainless steel, platinum, gold, silver and titanium. In some embodiments composite are formed of plastics and metals in order to utilize the superior processing characteristics of metals and the low thermal capacitance of plastics. In some embodiments, additive manufacturing methods, for example, 3D printing or injection molding can be used fabricate plates with features embedded in the plate during fabrication of the plate. In practice, the shapes of grooves in each plate are designed to obtain the desired hydraulic characteristics for each aperture in order to provide substantially similar flow rate to each aperture and provide a means for dislodging trapped material within an aperture. The main design variables are width and height and total path length of the groove. By changing these variables it is possible to obtain almost any desired hydraulic characteristics for a fluid passageway.

Figure 13A:
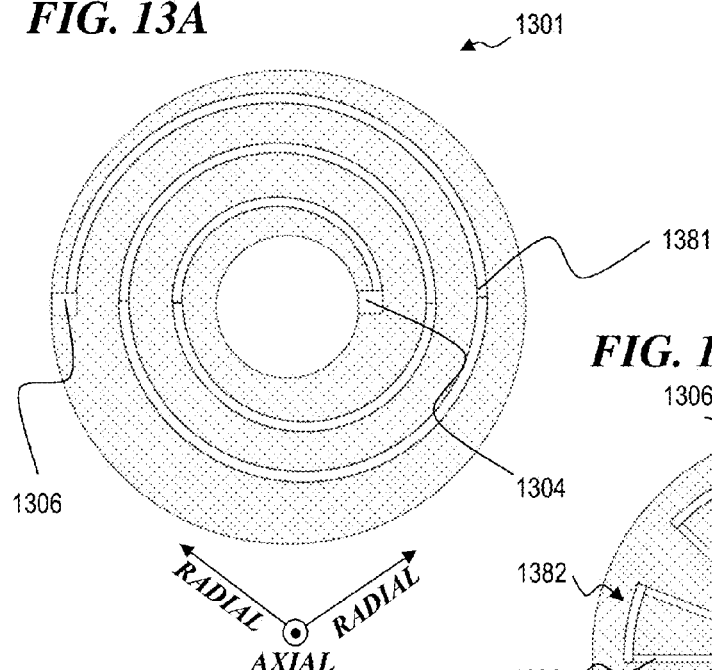
FIG. 13A is a cross-sectional view of a plate 1301 for an insert (such as 1220), wherein each plate 1301 contains only one channel 1381, according to some embodiments of the present invention.
Figure 13B:
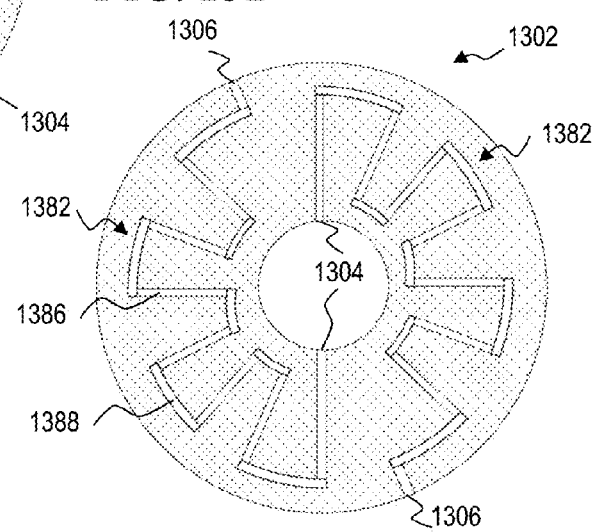
FIG. 13B is a cross-sectional view of a plate 1302 for an insert (such as 1220), wherein each plate 1302 contains two channels 1382, according to some embodiments of the present invention.
Figure 13C:
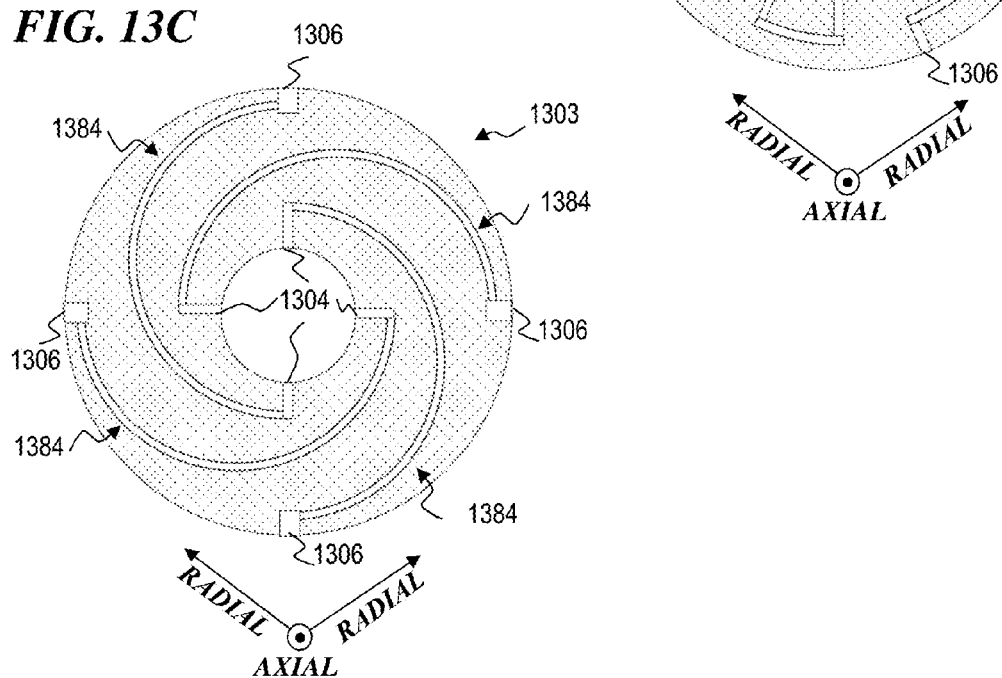
FIG. 13C is a cross-sectional view of a plate 1303 for an insert (such as 1220), wherein each plate 1303 contains four channels 1384, according to some embodiments of the present invention.

FIGS. 13A, 13B and 13C are cross-sectional views, perpendicular to the longitudinal axis of the shell tip, of three alternate embodiments of insert 1201 which show different channel geometric patterns formed into one surface of each plate (such as can be used to form insert 1201 of FIG. 12B), with each plate having different hydraulic characteristics.

FIG. 13A is a cross-sectional view of an insert (such as 1201) wherein each plate 1301 contains only one channel 1381 with a single fluid inlet 1304 and single fluid outlet 1306 connected to one aperture in a shell tip. In some embodiments, the outer electrode shell (for example, such as an aperture 1108 in shell 1120 of FIG. 11A).

FIG. 13B is a cross-sectional view of an insert (such as 1201) wherein each plate 1302 has two channels 1382 each having a plurality of radial channel segments 1386 and circumferential channel segments 1388 with each channel 1382 having an inlet port 1304 and outlet port 1306, with each individual channel connected to its own single aperture in the outer electrode shell (for example, such as an aperture 1108 in shell 1120 of FIG. 11A).

FIG. 13C is a cross-sectional view of an insert (such as 1201) wherein each plate 1302 has four channels 1384, each connected to an inlet port 1304 and outlet port 1306 with each individual channel 1384 connected to its own single aperture in the outer electrode shell (for example, such as an aperture 1108 in shell 1120 of FIG. 11A). In some embodiments the fluid channel (such as 1381, 1382, or 1384) will be formed by channels in one or more adjacent plates. In some embodiments the channels will have a substantially longer path length compared to the distance between the inside and outside radius of the plate. In some embodiments the channel will have a hydraulic diameter much less than a 0.004 inch (0.101 mm) hole. In some embodiments, the channel will have an L/d larger than two (2). In some embodiments, the channel will have an L/d larger than five (5). In some embodiments, the channel will have an L/d larger than twenty (20). In some embodiments, channels may have no entrance or exit creating a closed channel for containing a quiescent fluid or gas. Air-filled channels have a reduced thermal mass, thereby increasing temperature responsiveness of an ablation electrode so configured.

Figure 14A:
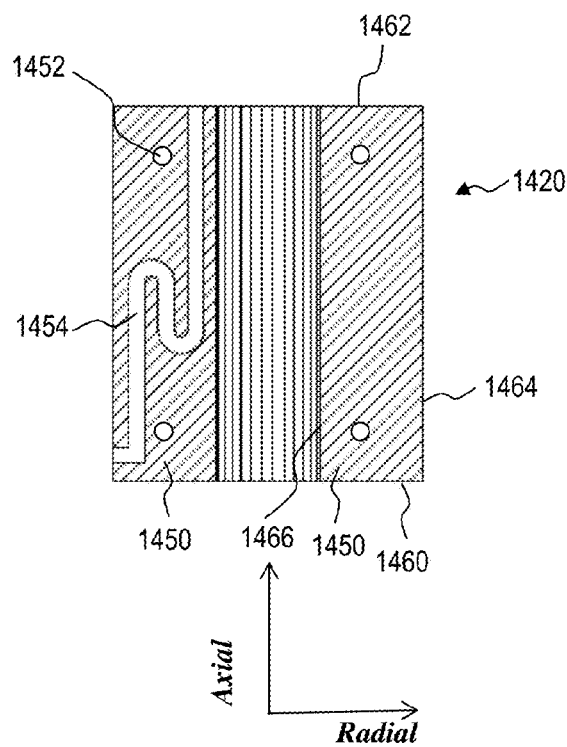
FIG. 14A is a longitudinal cross-sectional view of an insert 1420 manufactured with multiple vertical layers containing plates joined together to form the insert 1420.
Figure 14B:
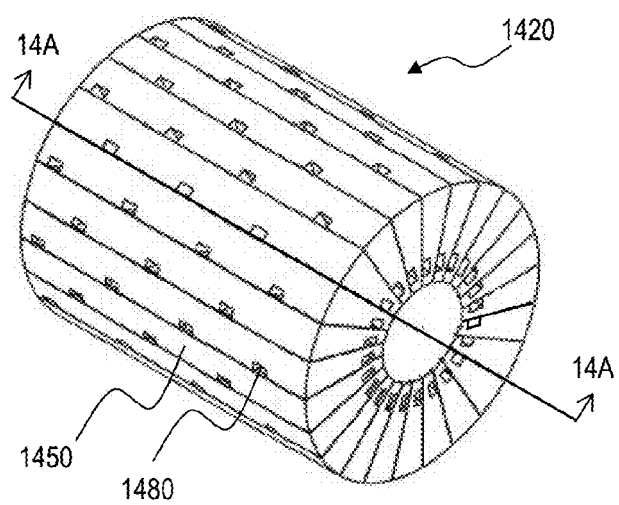
FIG. 14B is an isometric view of insert 1420.

FIGS. 14A and 14B are different views of an insert 1420 formed from a multiplicity of axially arranged plates according to another embodiment of the present invention.

FIG. 14A is a cross-sectional view of insert 1420 along the longitudinal axis.

FIG. 14B shows an isometric view of insert 1420. As shown in FIG. 14A, insert 1420 is constructed of plates 1450 stacked in a circumferential direction around the longitudinal axis of an electrode shell tip. Each plate has a pie-shaped geometry that widens in the outward direction along its radial dimension with top surface 1462 and bottom surface 1460. In one embodiment, a plate has an outer diameter defining exterior surface 1464 and an inner diameter defining an interior surface 1466. Other geometric shapes are possible within the scope of this invention, for example, the outer geometric shape shown in FIG. 8C could be used. The inner surface 1466 could also have a non-circular profile to provide space for instrumentation; for example, position sensors, force sensors or additional temperature instrumentation. Channels 1454 are formed into one or both planar surfaces of each plate. Each channel 1454 forms fluid passageway 1480 when abutting a surface of another plate to pass fluid from the interior to the exterior surfaces of the insert. In some embodiments, each plate has one or more alignment features 1452 which index each plate with respect to adjacent plates. In some embodiments, alignment feature 1452 includes an indentation or hole is used in one surface of one plate and a mating protuberance, such as for example a pin, is used in its adjacent plate. In some embodiments the alignment features 1452 in each plate are a combination of both indentations and protuberances on each surface.

Plates 1450 are made of materials which are easily shaped by subtractive or additive manufacturing methods. Preferably low-density materials are selected to reduce the overall thermal capacitance of an electrode assembly. In some embodiments, for example, polymer plastics are used including, but not limited to, high density polyethylene (HDPE), polyimides, polyesters, polyethylenes, polypropylenes, polyethylene terephthalate, polyetheretherketones (PEEK), polylatic acids (PLA), polycarbonates, acrylonitrile butadiene styrene (ABS), plastics under trade names such as Teflon®, Delrin®, as well as blends and mixtures thereof. In some embodiments plates are made from metals to utilize their superior subtractive processing characteristics or to utilize processing methods such as chemical etching. Suitable metals include but are not limited to copper, brass, aluminum, stainless steel, platinum, gold, silver and titanium. In some embodiments composite are formed of plastics and metals in order to utilize the superior processing characteristics of metals and the low thermal capacitance of plastics. In some embodiments, additive manufacturing methods, for example, 3D printing or injection molding can be used fabricate plates with features embedded in the plate during fabrication of the plate.

In some embodiments, channels in each plate are designed to obtain the desired hydraulic characteristics for each channel and aperture, in order to provide substantially similar flow rates to each aperture and provide a means for dislodging trapped material within an aperture. The main design variables are width and height and total path length of the indentation. By changing these variables it is possible to obtain almost any hydraulic characteristics desired.

FIGS. 15A through 15M show different geometric configurations for channels in a plate for various embodiments, each having different hydraulic characteristics and/or different exit locations on the plate. Other geometric patterns for the grooves, such as illustrated in FIG. 13A, FIG. 13B, and FIG. 13C for horizontal plates, are used for vertical plates such as shown in FIG. 14A and FIGS. 15A-15M. In some embodiments, each plate will contain only one channel connected to one aperture. In some embodiments, each plate will contain two channels, with each individual channel connected to its own single aperture. In some embodiments, each plate will contain four channels with each individual channel connected to its own single aperture. In some embodiments the channels will have a substantially larger path length compared to the difference between the inside and outside radius of the plate. In some embodiments the channel will have a hydraulic diameter, $d_h$, much less than a 0.004 inch (0.1016 mm) hole. In some embodiments, the channel will have an $L/d_h$ larger than two (2). In some embodiments, the channel will have an L/d larger than five (5). In some embodiments, the channel will have an L/d larger than twenty (20).

Figure 15A:
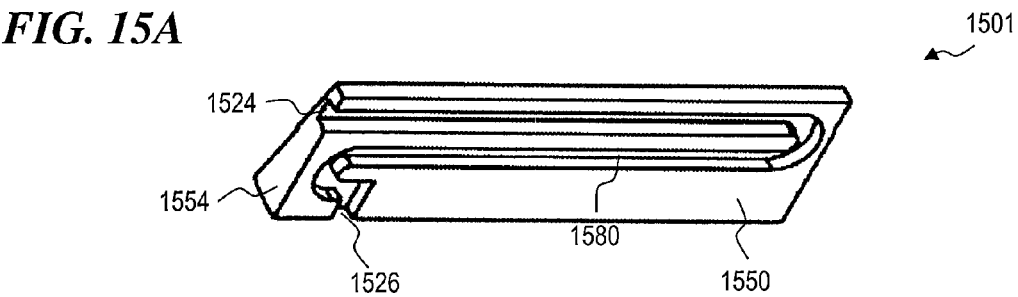
FIG. 15A is an isometric view of a radial section 1501 that can be used in place of radial plate 1450 of insert 1420 of FIG. 14B, according to some embodiments of the invention.
Figure 15B:
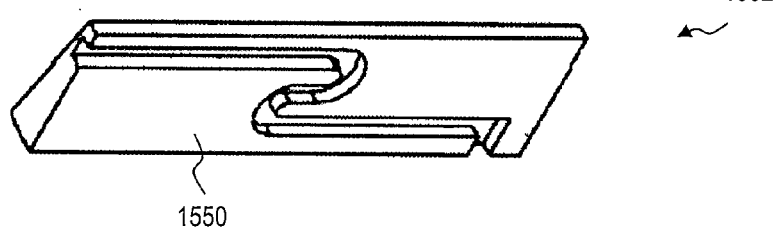
FIG. 15B is an isometric view of a radial section 1502 that can be used in place of radial plate 1450 of insert 1420 of FIG. 14B, according to some embodiments of the invention.
Figure 15C:
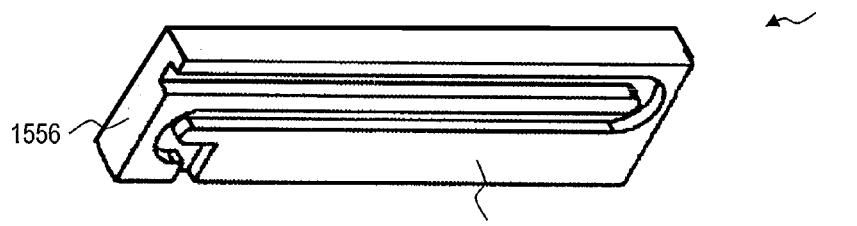
FIG. 15C is an isometric view of a stackable section 1503 that can be used in insert 1505 of FIG. 15E, according to some embodiments of the invention.
Figure 15D:
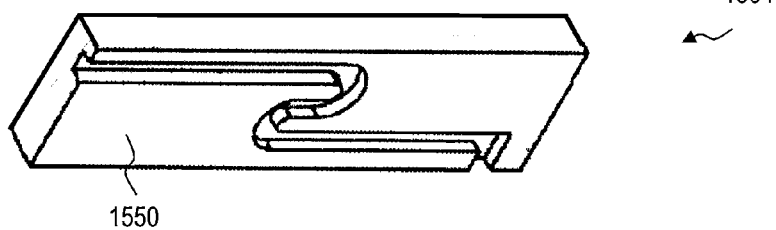
FIG. 15D is an isometric view of a stackable section 1504 that can be used in insert 1505 of FIG. 15E, according to some embodiments of the invention.
Figure 15E:
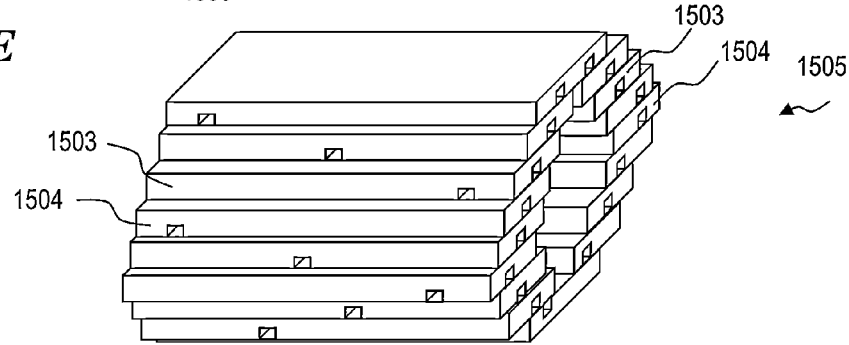
FIG. 15E is an isometric view of an insert 1505, according to some embodiments of the invention.
Figure 15F:
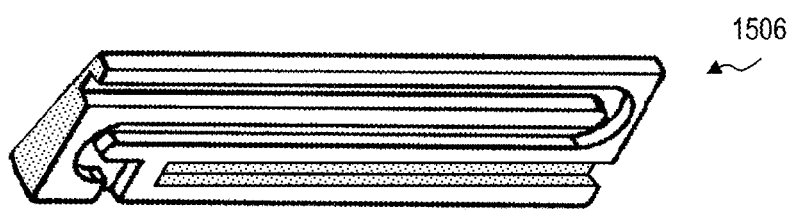
FIG. 15F is an isometric view of a radial section 1506 that can be used in place of radial plate 1450 of insert 1420 of FIG. 14B, according to some embodiments of the invention.
Figure 15G:
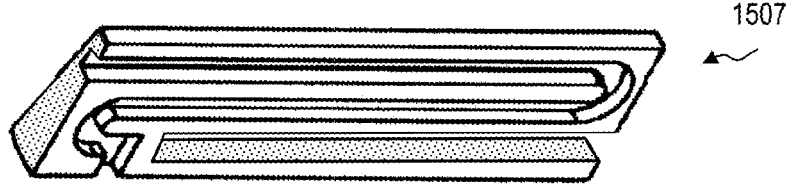
FIG. 15G is an isometric view of a radial section 1507 that can be used in place of radial plate 1450 of insert 1420 of FIG. 14B, according to some embodiments of the invention.
Figure 15H:
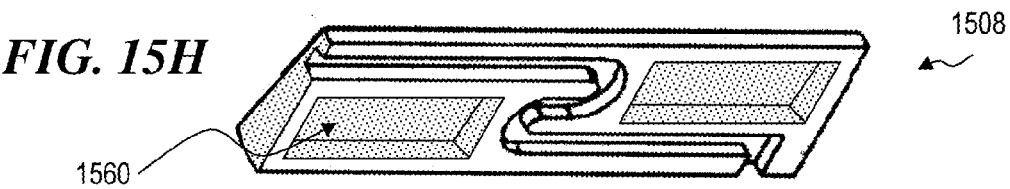
FIG. 15H is an isometric view of a radial section 1508 that can be used in place of radial plate 1450 of insert 1420 of FIG. 14B, according to some embodiments of the invention.
Figure 15I:
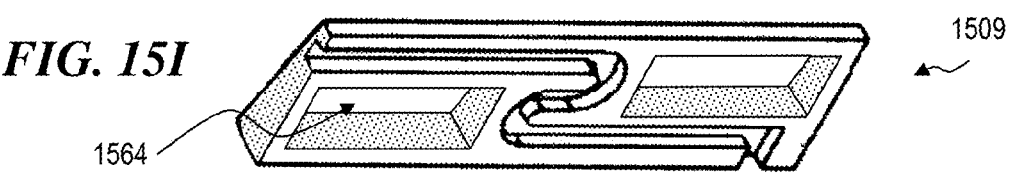
FIG. 15I is an isometric view of a radial section 1509 that can be used in place of radial plate 1450 of insert 1420 of FIG. 14B, according to some embodiments of the invention.
Figure 15J:
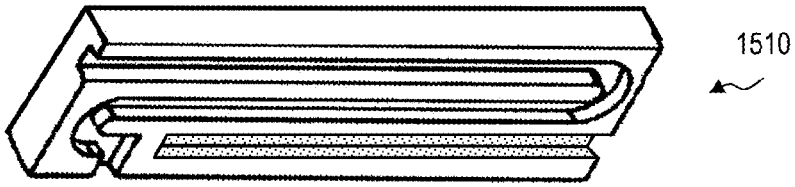
FIG. 15J is an isometric view of a radial section 1510 that can be used in place of radial plate 1450 of insert 1420 of FIG. 14B, according to some embodiments of the invention.
Figure 15K:
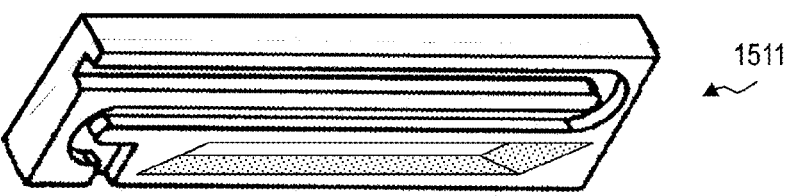
FIG. 15K is an isometric view of a radial section 1511 that can be used in place of radial plate 1450 of insert 1420 of FIG. 14B, according to some embodiments of the invention.
Figure 15L:
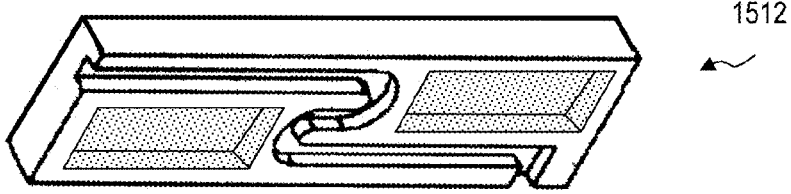
FIG. 15L is an isometric view of a radial section 1512 that can be used in place of radial plate 1450 of insert 1420 of FIG. 14B, according to some embodiments of the invention.
Figure 15M:
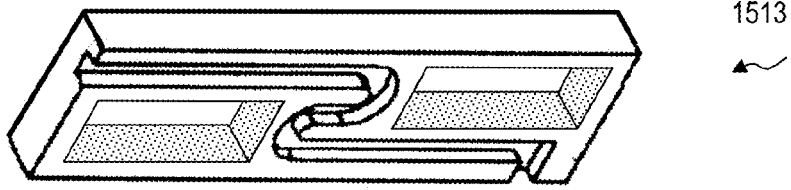
FIG. 15M is an isometric view of a radial section 1513 that can be used in place of radial plate 1450 of insert 1420 of FIG. 14B, according to some embodiments of the invention.

FIGS. 15A through 15D and 15F through 15M are isometric views of insert 1420 of FIG. 14A. Each figure illustrates a plate 1550 with a channel 1580 formed in one its surfaces. Each channel 1580 has an inlet port 1524 and outlet port 1526 operably coupled to channel 1580. FIGS. 15A, 15B, and 15F through 15I illustrate plates which have the shape of a sector of a circle on both ends 1554. These plates are suitable for configuring multiple plates to form circular insert such as insert 1420 of FIG. 14B. FIGS. 15C, 15D, and 15J through 15M illustrate a plate 1558 which has a rectangular shape on both ends 1556. These plates are suitable for configuring multiple plates to form stepped insert 1505 such as shown in FIG. 15E. Inserts can be formed by combining plates with differing channel configurations. FIGS. 15F thru 15L illustrate different embodiments of plates 1550 which have areas in which material has been partially removed to form 1560, or fully removed such as FIG. 15M, to form holes 1564 through a section of plate 1550 to form a hollow cavity within the plate. These features allow for making a composite insert structure to create an insert with a lower thermal capacitance or to provide spaces for instrumentation or sensors, such as temperature probes or positional or orientation sensors. These channel configurations can be used for wedge or rectangular plates.

Figure 16A:
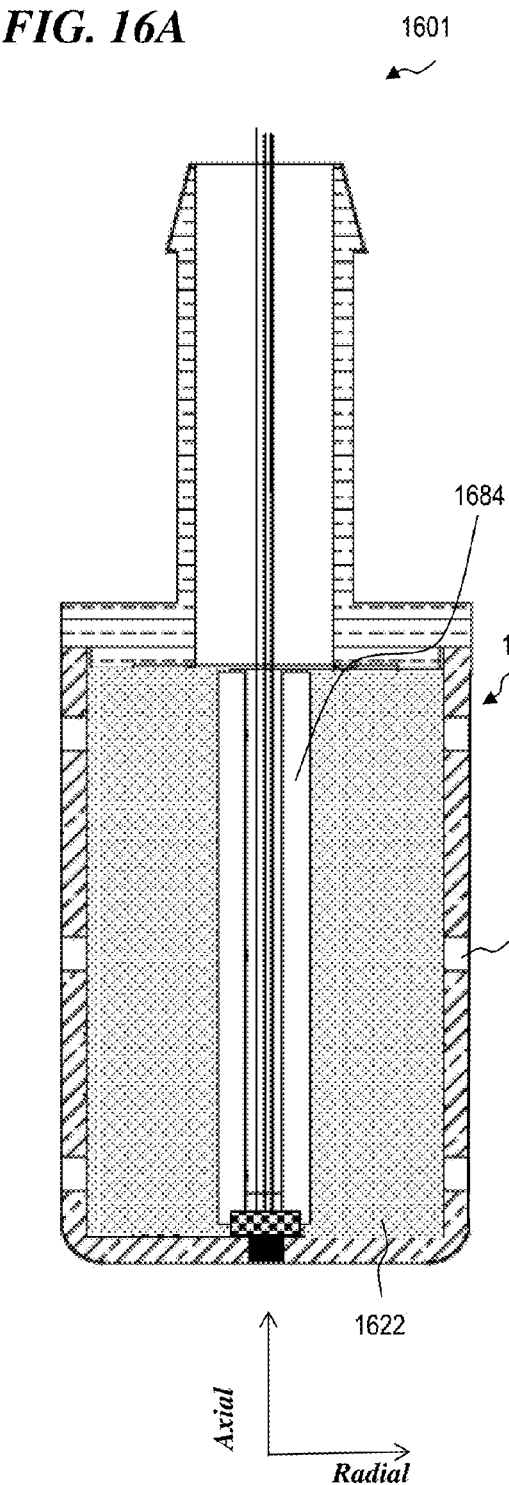
FIG. 16A is a cross-sectional view along the longitudinal axis of an ablation electrode 1601 fabricated using a porous medium 1622 as the insert material.
Figure 16B:
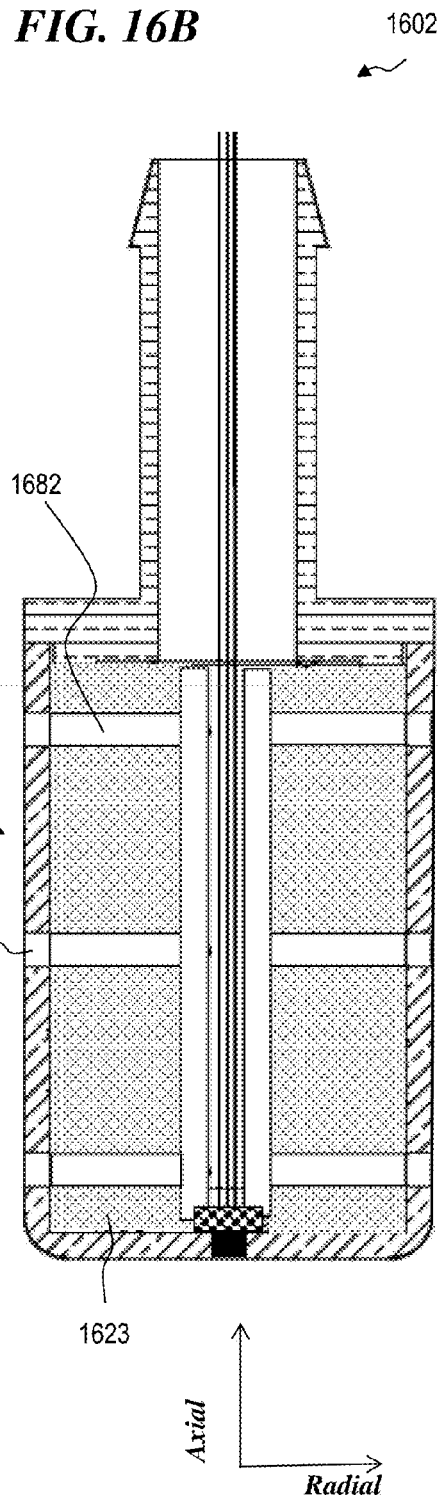
FIG. 16B is a cross-sectional view along a longitudinal axis of an ablation electrode using a porous medium as an insert 1602 with fluid passages through the porous medium 1623.

FIGS. 16A and 16B are cross-sectional views along the longitudinal axis of ablation electrodes fabricated using a porous material for the insert.

FIG. 16A is a cross-sectional view of an ablation tip 1601, wherein insert 1622 is made of an open-cell porous medium in which pores are operably coupled to one another to create a fluid pathway through the medium which effectively operably couples fluid from central passageway 1684 to apertures 1608.

FIG. 16B is a cross-sectional view of an ablation tip 1602 with the addition of discrete fluid passageways 1682 to operably couple fluid from central fluid channel 1684 to apertures 1608. The use of a porous medium for insert 1623 is potentially beneficial to creating a more-uniform flow distribution through the apertures 1608 and also for maintaining a quiescent (non-moving) fluid layer in contact with the interior wall of shell 1610 to reduce temperature variations within the shell and maintain a temperature below the temperature at which for blood coagulates.

Figure 17A:
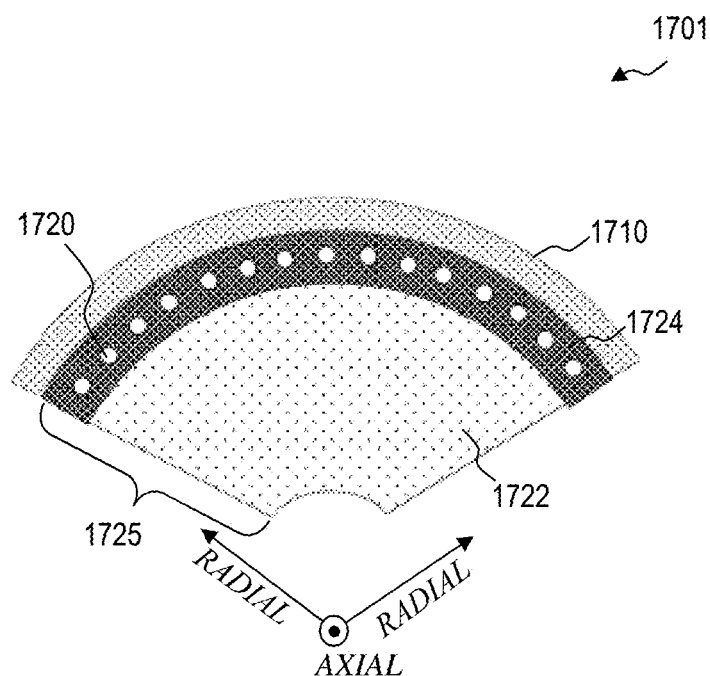
FIG. 17A is a segment of a perpendicular cross-sectional view of an ablation electrode 1701 fabricated using hypodermic tubing 1720, according to some embodiments of the invention.

FIG. 17A is a segment of a perpendicular cross-sectional view of an ablation electrode 1701 fabricated using hypodermic tubing (hollow steel needles) 1720 as fluid channels within an insert, according to some embodiments of the invention. In FIG. 17A, a thin layer of circumferential insert material 1724 has a plurality of pieces of hypodermic tubing 1720 inserted along the axial length of the insert in circumferential insert material 1724 near the outer surface and parallel to the longitudinal axis of insert 1725. The tubes of the plurality of tubes 1720 are spaced around the circumference of the insert in a uniform pattern, although other patterns are within the scope of the present invention. In some embodiments, circumferential material 1724 is in contact with the interior surface of shell 1710 and the exterior surface of insert core 1722.

Figure 17B:
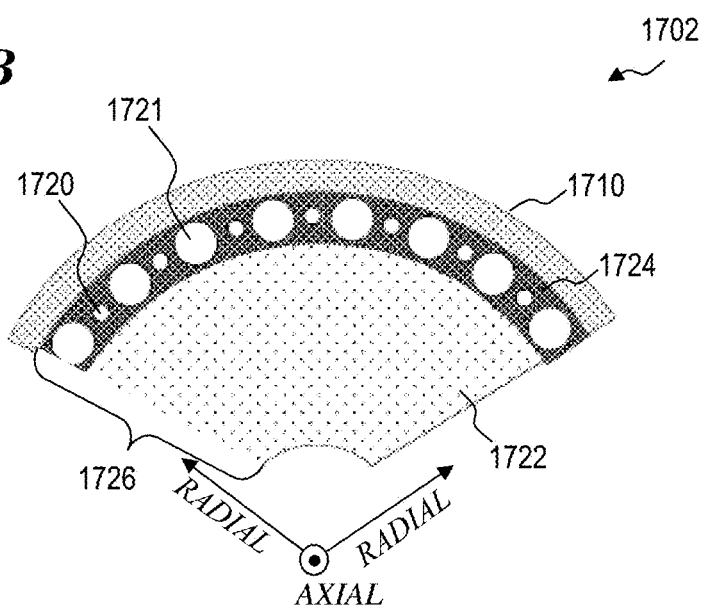
FIG. 17B is a segment of a perpendicular cross-sectional view of an ablation electrode 1702 fabricated using different sizes of hypodermic tubing 1720 and 1721, according to some embodiments of the invention.

FIG. 17B is a segment of a perpendicular cross-sectional view of an ablation electrode 1702 fabricated using hypodermic tubing 1720, according to some embodiments of the invention. FIG. 17B illustrates the use of hypodermic tubing with a plurality of different diameters, for example, larger tubing 1721 and smaller tubing 1720 in circumferential insert material 1724 of insert 1726.

Figure 18:
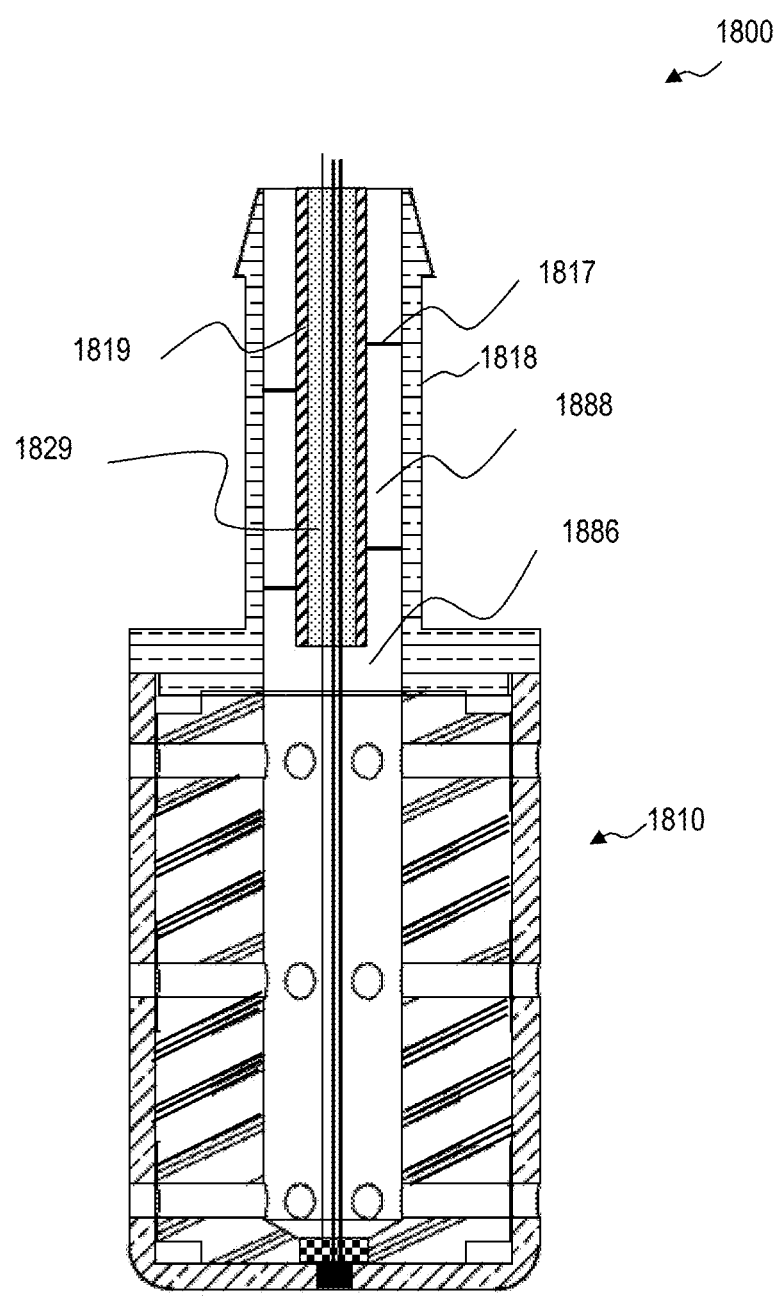
FIG. 18 is a cross-sectional view along a longitudinal axis of a device 1800 illustrating a delivery tube 1818 connected to the ablation electrode of the present invention with a cooling means 1819 within the delivery tube.

FIG. 18 is a cross-sectional view of a device 1800 that includes a fluid delivery tube 1818 connected to an ablation electrode 1810 of the present invention with a cooling means within a fluid delivery tube 1818. In one embodiment of this invention, outer delivery tube 1818 has an inner tube 1819 inserted into its central lumen. Small tabs 1817 maintain the outer surface of the inner tube 1819 at a fixed distance and concentric with the interior surface of the delivery tube 1818. The two surfaces form a fluid passageway 1888 through which fluid flows during an ablation procedure. The lumen of the inner tube 1819 is filled and sealed with an adhesive or sealant 1829 to prevent flow of water therethrough. In some embodiments, the outer diameter of the delivery tube 1818 is 0.065 inches (1.657 mm) with an inner diameter of 0.059 inches (1.500 mm). The outer diameter of the inner tube 1819 is 0.049 inches (1.245 mm) with an inner diameter of 0.042 inches (1.067 mm). During operation, fluid flows through the annular fluid channel 1888 between inner tube 1819 and outer tube 1818 providing a higher-velocity fluid stream to cool external tube 1818 to prevent heating of the delivery tube 1818 and adjacent catheter structures. This cooling effect helps reduce the incidence of coagulum formation on the exterior surface of a catheter shaft near the ablation electrode device 1800.

Figure 19A:
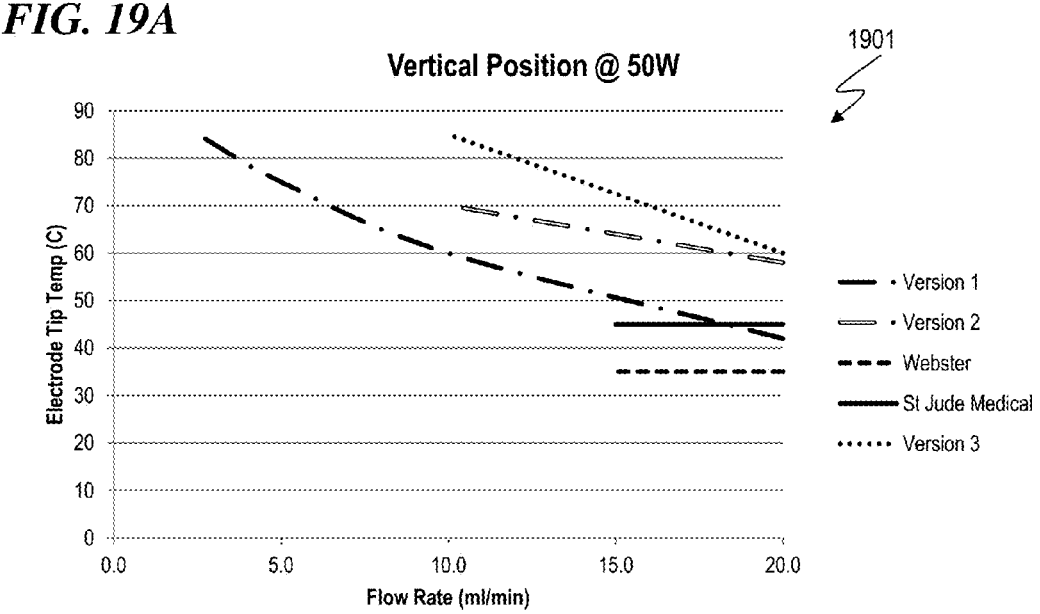
FIG. 19A is a graph 1901 that shows electrode operating temperature for various fluid flow rates at an RF power setting of 50 Watts of the ablation electrode according to some embodiments of the present invention.

FIG. 19A is a graph 1901 showing preliminary performance data for three embodiments of ablation electrode according to the present invention. The electrodes were 2.66-mm-diameter by 5-mm-long. Version 1 was fabricated in accordance with FIG. 3 using triangular channels of FIG. 3B for the insert exterior surface. Version 2 was fabricated in accordance with FIG. 8 using the geometric pattern for the protuberances shown in FIG. 9B. Version 3 was fabricated in accordance with FIGS. 3A, 3B, and 3C using flat channels of FIG. 4C for the insert exterior surface. Each electrode was tested on the bench in a saline bath at 37° C. using chicken breast meat at an RF power setting of 50 W and at various total fluid flow rates ranging from 2.5 to 20 ml/min. The graph also presents data from the Nakagawa paper (cited in the Background section above) in a canine-thigh-preparation model for two conventional irrigated ablation electrodes manufactured by BioSense Webster and by St Jude Medical. As demonstrated in the graphs, current conventional ablation electrodes have a significantly lower operating temperature at 15 ml/min compared to Version 2 and Version 3 of the present invention. All three catheters designed using embodiments of the present invention show an ablation electrode that has an electrode temperature that is more sensitive to changes in fluid-flow rate, as compared to either conventional electrode designs.

Table 5 shows the calculated pressure drop (DELTA P) across apertures for different configurations at total fluid flow rates of 5 ml/min and 15 ml/min. The first two pairs of lines of Table 5 represent aperture configurations having 12 and 56 apertures, respectively, for conventional irrigated electrode ablation presented in the Nakagawa paper (cited in the Background section above). The bottom two pairs of lines represent two embodiments of an ablation electrode according to the present invention using twenty-seven rectangular apertures of different dimensions. As Table 5 illustrates, higher aperture pressure drops are possible using rectangular apertures according to the present invention than are possible in the two conventional configurations specified here.

TABLE 5

| # | TYPE | DIMENSIONS | | 5 ml/min DELTA P | 15 ml/min DELTA P | Units |
|---|------|------------|---|------------------|-------------------|-------|
| 12 | Circle | 0.0150 (DIA) × 0.030 (D) | in | 0.003 | 0.010 | psi |
| | | 0.381 (DIA) × 0.762 (D) | mm | 21 | 69 | Pa |
| 56 | Circle | 0.0035 (DIA) × 0.003 (D) | in | 0.026 | 0.097 | psi |
| | | 0.0889 (DIA) × 0.0762 (D) | mm | 179 | 669 | Pa |

TABLE 5-continued

| # | TYPE | DIMENSIONS | | 5 ml/min DELTA P | 15 ml/min DELTA P | Units |
|---|------|------------|---|------------------|-------------------|-------|
| 27 | Slit | 0.0005 (W) × 0.020 (L) × 0.005 (D) | in | 1.000 | 3.379 | psi |
|    |      | 0.0127 (W) × 0.508 (L) × 0.127 (D) | mm | 6,895 | 23,297 | Pa |
| 27 | Slit | 0.0010 (W) × 0.010 (L) × 0.005 (D) | in | 0.28 | 1.000 | psi |
|    |      | 0.0254 (W) × 0.254 (L) × 0.127 (D) | mm | 1,931 | 6,895 | Pa |

Figure 19B:
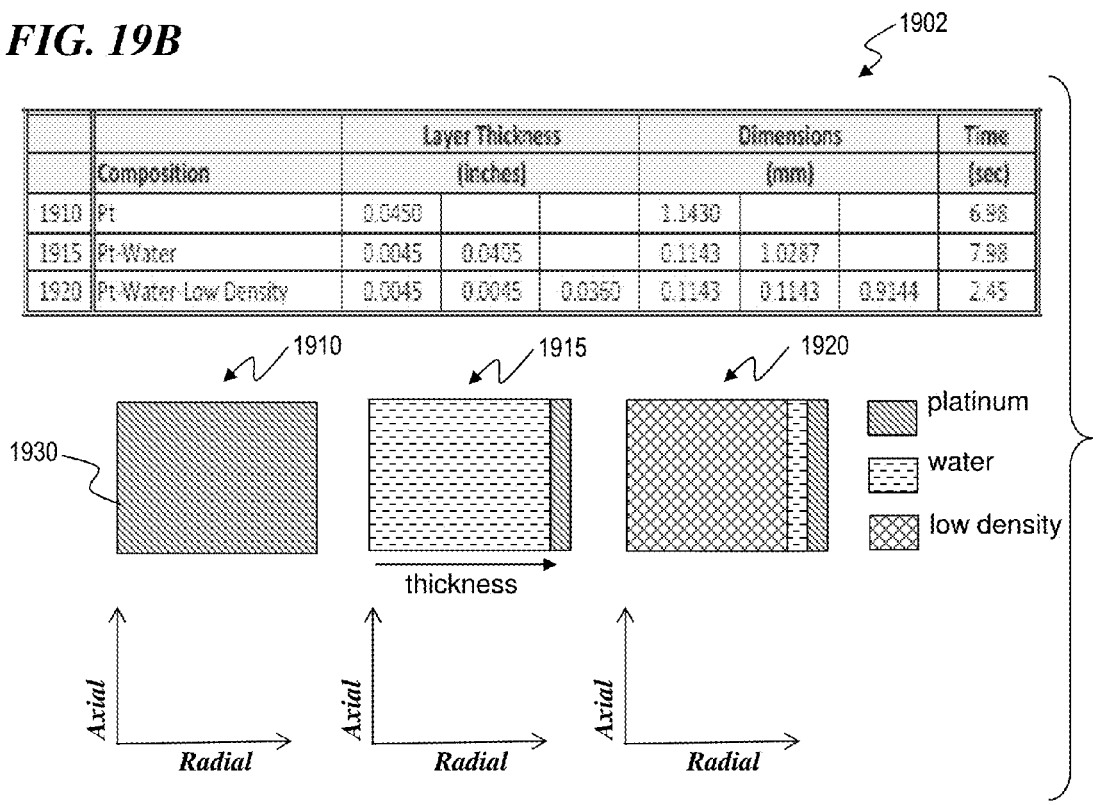
FIG. 19B is a table 1902 that shows the calculated thermal response time of three simulated ablation electrode configurations 1910, 1915, and 1920 subject to a step change in temperature, according to some embodiments of the present invention.

FIG. 19B includes table 1902 which shows the calculated thermal response time of an ablation electrode for an embodiment of an ablation electrode according to the present invention. One method for measuring thermal response is to determine the time required for a body to respond to a step change in its surrounding temperature. The first order time constant is defined as the time for a body to reach a temperature which reduces the initial temperature difference of the step temperature change by 1/e (62.3%). For example for a body at 25° with a step change of 100°, the time at which the body reaches 87.3° would be its first order time constant. For purposes of these calculations, a one-dimensional numerical transient thermal analysis was performed for an electrode thickness of 0.045 inches (1.143 mm) which is representative of an 8 French (2.66 mm) tip electrode. The material composition was varied to represent two different current tip electrode designs and an embodiment of the present invention. Reference 1910 is a cross-sectional view of the right-hand half of a solid platinum electrode, reference 1915 is a cross-sectional view of the right-hand half of a thin platinum shell filled with the remainder of the electrode filled with water and reference 1920 is a cross-sectional view of the right-hand half of a thin platinum outer shell, a thin water layer with the remainder of the electrode filled with a low-density material. The numerical simulation subjected surface 1930 to a step change of 56° C. in a fluid bath. As illustrated in FIG. 1903, the use of a low-density material within an ablation electrode can reduce thermal response times by up to a factor of three.

In some embodiments, the present invention includes an irrigated ablation electrode with non-circular elongated apertures in its shell to uniformly distribute fluid over its exterior surface during an ablation procedure. Traditionally, irrigated ablation electrodes have used circular apertures because this geometry provides the largest flow area through the aperture for the least wetted perimeter distance around the aperture, reducing hydraulic pressure drop through the aperture, and also lends itself to less-expensive fabrication methods. A major disadvantage of this geometry is a propensity for low-aspect-ratio apertures to plug with biological material during a clinical procedure, resulting in poor flow distribution and possibly thrombus formation on the exterior surface of the ablation electrode. Plugging of apertures can be minimized and even eliminated by careful consideration of aperture design.

One desirable design aspect provided by the present invention is that the aperture design increases the pressure drop through an aperture to provide a higher fluid hydraulic force with which to dislodge trapped material. In some embodiments, this is accomplished by using a non-circular elongated aperture geometry which increases the wetted perimeter of the aperture in contact with fluid compared to its cross-sectional flow area. For example the use of an elongated rectangular channel with an aspect ratio defined as length, L, divided by width, W, of forty (40), but with the same cross-sectional flow area as a circular aperture, results in a ten-fold increase in pressure drop through the channel and aperture of the present invention. Another desirable design aspect provided by the present invention is that the aperture design makes it inherently difficult to plug rectangular apertures that have large aspect ratios. This principle can be seen in other unrelated fields, for example in the design of filters for inlets of fluid pumps exposed to liquids with high solids content, for example, turbid waters. One such filter is a pump assembly manufactured by Red Lion for withdrawing water from a lake bed. The outer shell of the inlet filter has a diameter of 2.5 inches (63.5 mm) with multiple slots, each 0.010 inches (0.254 mm) high by 1.96 inches (6.35 mm) wide. In some embodiments, the present invention uses both design considerations to provide a more uniform flow over the exterior surface of the ablation electrode with reduced propensity to plug during clinical procedures.

FIG. 20A is a cross-sectional view along the longitudinal axis of an irrigated ablation electrode 2001 according to one embodiment of the present invention.

Figure 21A:
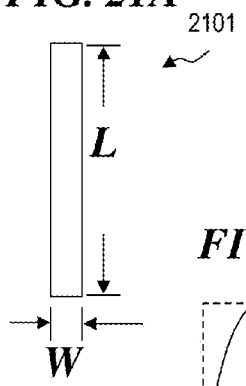
FIGS. 21A, 21B, 21C, 21D, 21E, 21F, 21G and 21H are plan views of various aperture embodiments with different aperture geometries according to some embodiments of the present invention.

FIG. 20B is an isometric view of an irrigated ablation electrode 2001. As shown in FIG. 20A, in some embodiments, ablation electrode assembly 2001 includes a cup-shaped electrode shell 2010 having a cylindrical wall 2012 and a rounded connection 2013 to a flat bottom plate 2014. In some embodiments, shell 2010 has a welded connection 2015 to top plate 2016, and top plate 2016 has a welded connection to delivery tube 2018. In some embodiments, the shell 2010 is constructed of a thin layer of metal of uniform wall thickness that is electrically and thermally conductive. In some embodiments, shell 2010 includes one or more metals selected from the group consisting of gold, platinum, silver, iridium, copper, steel, aluminum, brass and palladium as well as composites, mixtures and coatings of these materials. In some embodiments, the shell diameter 2091 is in a range of 0.015 to 0.50 inch (0.038 to 12.7 mm), inclusive, and in some embodiments, preferably in a range of 0.040 to 0.131 inches (1.016 to 3.327 mm), inclusive. In some embodiments, the shell length 2092 is in the range of 0.020 to 1.000 inches (0.508 to 25.4 mm), inclusive, and in some embodiments, preferably in a range of 0.080 to 0.400 inches (2.032 to 10.16 mm), inclusive. In some embodiments, material wall thickness 2093 is in a range of 0.0001 to 0.0125 inches (0.0025 to 0.317 mm), inclusive, and in some embodiments, preferably in a range of 0.001 to 0.010 inches (0.0254 to 0.254 mm), inclusive. In some embodiments, the shell is generally manufactured as a cup containing cylindrical side wall 2012, transition region 2013, and distal plate 2014 to which is affixed a proximal plate 2016 with joint 2015. In some embodiments, top plate 2016 is joined to fluid delivery tube 2018 with joint 2019. In some embodiments, fluid delivery tube 2018 mechanically couples the irrigated ablation electrode to a catheter assembly 110 (of FIG. 1). In some embodiments, shell 2010 includes a plurality of slit-shaped apertures 2008 that perforate the shell for purpose of fluid passage therethrough to its exterior surface. FIG. 21A is a plan view of a convex slit-shaped aperture 2101 that is a rectangle and has an aspect ratio of eight (8:1).

Figure 21C:
Figure 21B:
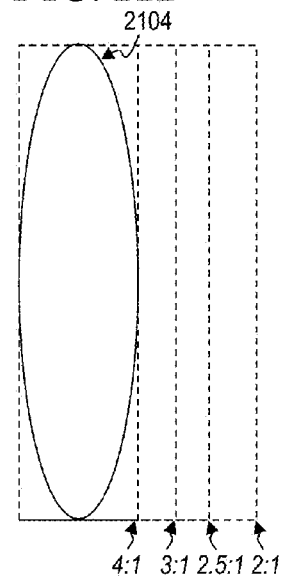

FIG. 21B is a plan view of a convex slit-shaped aperture 2102 that has semicircular ends and straight parallel sides (a rounded-end rectangular shape) and has an aspect ratio of ten (10:1). The dashed-line reference overlay shows aspect ratios of 10:1, 4:1, 3:1, 2.5:1 and 2:1.

FIG. 21C is a plan view of a convex slit-shaped aperture 2103 that is a parallelogram and has an aspect ratio of eleven (11:1).

Figure 21D:
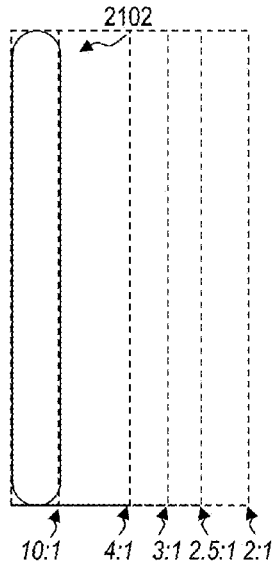

FIG. 21D is a plan view of a convex slit-shaped aperture 2104 that is an oval and has an aspect ratio of four (4:1).

Figure 21F:
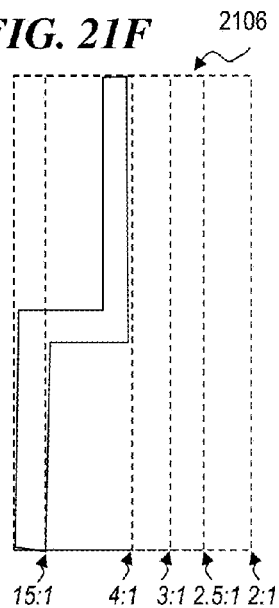
Figure 21G:
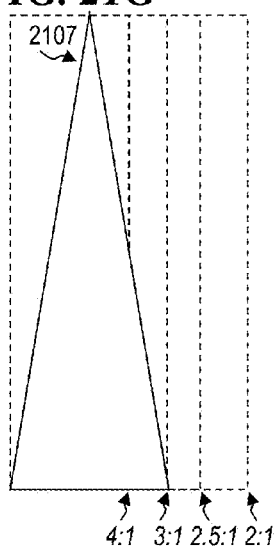
Figure 21E:
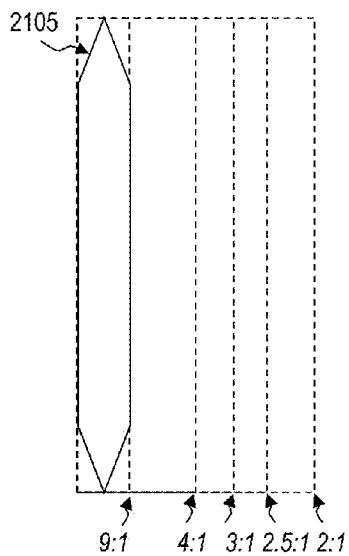

FIG. 21E is a plan view of a convex slit-shaped aperture 2105 that is a six-sided polygon and has an aspect ratio of nine (9:1).

FIG. 21F is a plan view of a non-convex slit-shaped aperture 2106 that has three approximately rectangular segments connected at approximately right angles and has an aspect ratio of greater than fifteen (>15:1). The dashed-line reference overlay shows aspect ratios of 15:1, 4:1, 3:1, 2.5:1 and 2:1. Because aperture 2106 includes the horizontal segment shown, its aspect ratio is somewhat greater than the 15:1 ratio of the leftmost dashed-line rectangle.

FIG. 21G is a plan view of a convex slit-shaped aperture 2107 that is a triangle and has an aspect ratio of three (3:1).

Figure 21H:
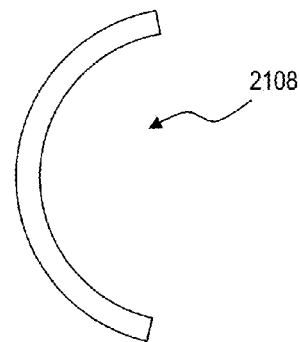

FIG. 21H is a plan view of a non-convex slit-shaped aperture 2108 that has two semicircular walls with a substantially constant width, and has an aspect ratio of about seventeen (17:1).

Examples of aperture shapes used by some embodiments, include, but are not limited to, these shapes: rectangular, ellipsoidal, crescent, hemispherical, and other elongated shapes as illustrated in FIGS. 21A through 21H.

In some embodiments, minimum aperture linear dimensions are in a range from 0.0001 to 0.050 inches (0.00254 to 1.270 mm), inclusive, preferably from 0.001 to 0.010 inches (0.0254 to 0.254 mm), inclusive, while maximum aperture linear dimensions can range from 0.005 to 0.050 inches (0.127 to 1.27 mm), inclusive, preferably from 0.010 to 0.020 inches (0.254 to 0.508 mm), inclusive. In some embodiments, aspect ratios are in a range from 1 to 1,000, inclusive, but in some embodiments, preferably from 5 to 40, inclusive. The shape, cross sectional area and aspect ratio of the apertures should be consistent with obtaining the desirable hydraulic characteristics to provide uniform fluid coverage over the entire exterior surface of an irrigated ablation electrode and reduce the likelihood of obstructions of an aperture during a clinical procedure. Preferably the geometry of the cross-section of an aperture does not change with location along the depth of the slots, i.e., from its interior to exterior surface.

Variations in geometry of an aperture cross section are permissible within the scope of this invention. Such variations may be inherent in manufacturing methods for fabricating an aperture or may be part of a design feature to achieve an intended hydraulic effect.

Figure 22A:
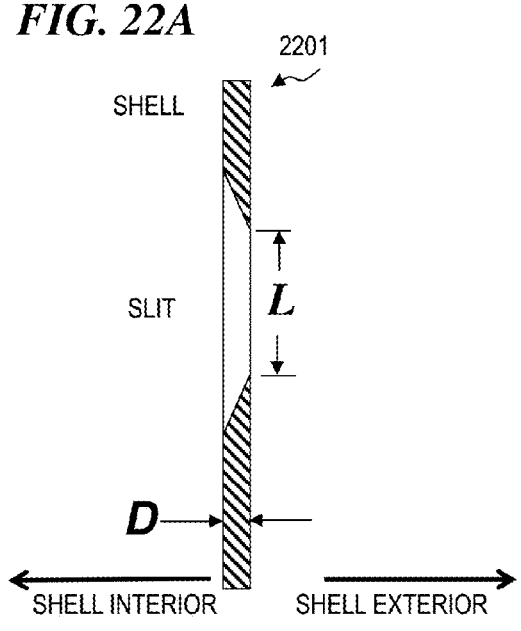
FIGS. 22A, 22B and 22C are radial cross-sectional views of the surface of three different ablation electrodes 2201, 2202, and 2203 through the centerline of an aperture illustrating an electrode wall with three different slot profiles according to some embodiments of the present invention.
Figure 22B:
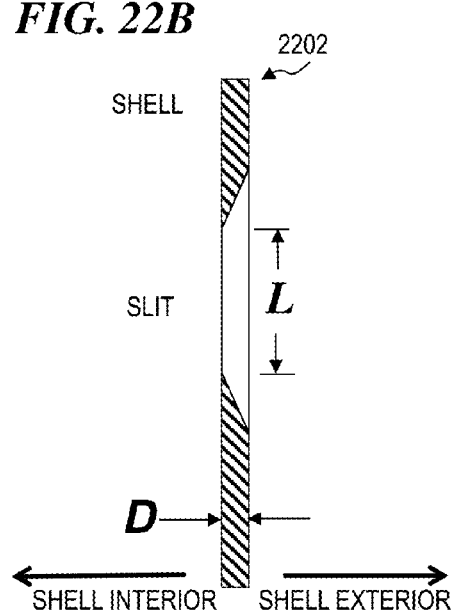
Figure 22C:
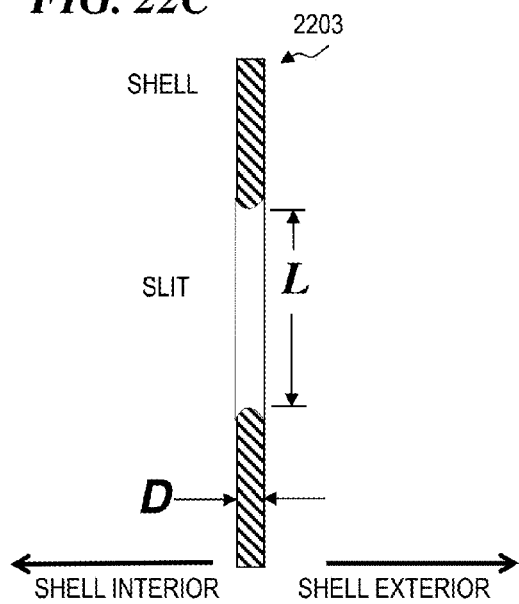

FIG. 22A illustrates a cross-sectional profile of an aperture obtained, in some embodiments, using laser, while FIG. 22B illustrates a profile using a slitting saw, while FIG. 22C illustrates a profile using chemical etching according to some embodiments.

Figure 23A:
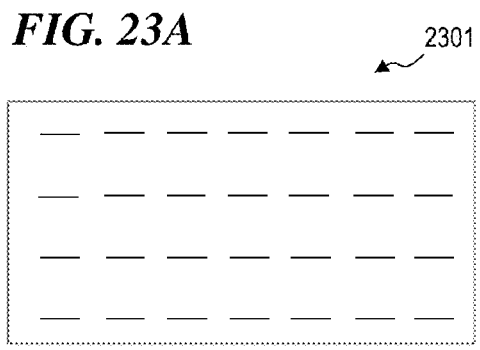
FIG. 23A is a plan flattened view of the circumferential exterior surface of an ablation electrode 2301 having a first geometric slot pattern, according to some embodiments.
Figure 23B:
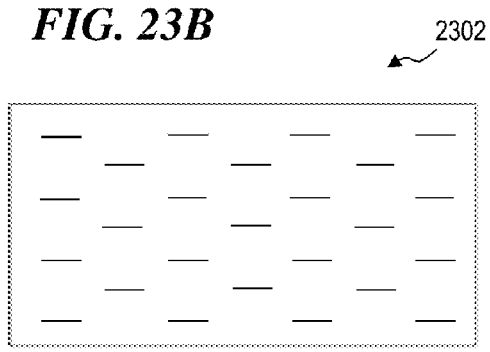
FIG. 23B is a plan flattened view of the circumferential exterior surface of an ablation electrode 2302 having a second geometric slot pattern, according to some embodiments.
Figure 23C:
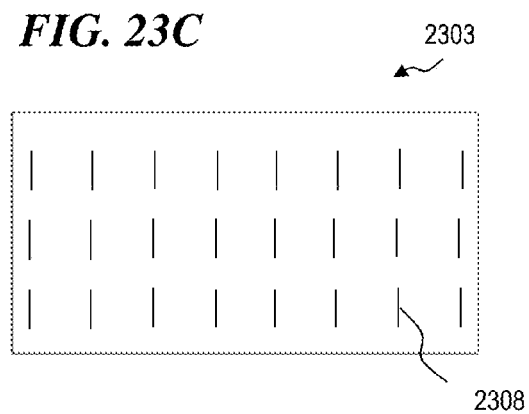
FIG. 23C is a plan flattened view of the circumferential exterior surface of an ablation electrode 2303 having a third geometric slot pattern, according to some embodiments.
Figure 23D:
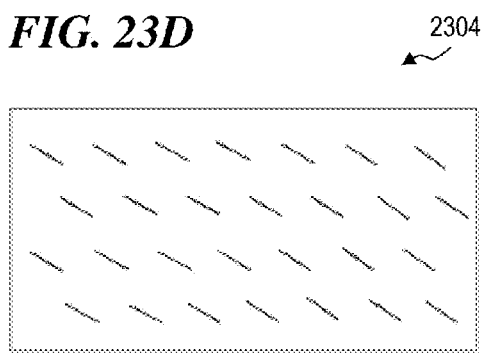
FIG. 23D is a plan flattened view of the circumferential exterior surface of an ablation electrode 2304 having a fourth geometric slot pattern, according to some embodiments.
Figure 23E:
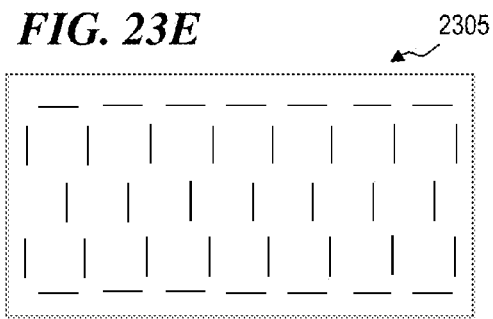
FIG. 23E is a plan flattened view of the circumferential exterior surface of an ablation electrode 2305 having a fifth geometric slot pattern, according to some embodiments.

As illustrated in FIG. 20B, in some embodiments, a plurality of apertures is arranged with the longest dimension (the length) of each slit-shaped aperture in a plane that is perpendicular to the longitudinal axis of an irrigated ablation electrode to form a square or rectangle pattern when their geometric centers are connected by a line. FIGS. 23A thru 23E are each a plan view of one of a plurality of other geometric patterns of some embodiments of the present invention. In some embodiments, apertures 2308 are arranged in a triangular pattern as shown in FIG. 23B. In some embodiments, apertures are oriented parallel to the longitudinal axis of an electrode, FIG. 23A while in other embodiments the apertures are oriented perpendicular to the longitudinal axis, as in FIG. 23C. In some embodiments the apertures are oriented at an angle to the longitudinal axis of an electrode, FIG. 23D. In some embodiments, selected apertures are oriented perpendicular to the longitudinal axis of the electrode while other selected apertures are oriented parallel to this axis as illustrated in FIG. 23E to provide good fluid distribution in electrode orientations both perpendicular and parallel to tissue. In some embodiments, the geometric pattern is non-uniform, to provide more fluid to selected regions than to other regions of an irrigated ablation electrode, especially ones more susceptible to overheating, for example, junction of a shell cylindrical surface with shell bottom plate or shell top plate with catheter shaft. Other geometric patterns are contemplated within the scope of the present invention and are not limited to the illustrated exemplary patterns.

In some embodiments, flow exiting an aperture surface of an ablation electrode is directed at angles less than 90 degrees to the exterior surface. This directed flow provides additional cooling to the distal edge of an ablation electrode and increases fluid momentum to impinge fluid on the surface of cardiac tissue in contact with an ablation electrode especially when an ablation electrode is oriented perpendicular to tissue. Is some embodiments, the aperture directs flow proximally towards the junction between an electrode and catheter shaft. In some embodiments, flow is directed circumferentially from apertures whose long axis is oriented longitudinally to augment cooling of tissue when an electrode is oriented with its cylindrical shape or side in contact with tissue. In some embodiments, a combination of two or more flow directions is incorporated into the apertures of an ablation electrode.

In some embodiments, manufacturing of microapertures in thin materials is done in one or more of several different ways. In some embodiments, for rectangular aperture with heights larger than 0.004 inches (0.106 mm), a slitting saw is mounted in a milling machine. For smaller holes, laser microdrilling using a UV diode-pumped solid-state laser (DPSSL) can make holes as small as 0.0004 inch (0.0106 mm). Also, electron-beam drilling processes can produce aperture widths as small as 0.002 inch (0.0508 mm) and electron discharge micro-machining (EDM) as small as 0.0002 inches (0.00508 mm). Most of these processes can make apertures with non-circular geometries by trepanning which traces an outline of a geometric shape in the material. Generally, a micromachining process leaves artifacts or residual features within the aperture which result in variations along its depth. For example, laser machining can produce apertures with a slight edge taper in the cross-sectional profile with the exterior surface have the smallest dimension. Other variations are anticipated within the scope of the present invention.

In one embodiment, apertures with a rectangular cross section or slots are used as the sole means for distributing fluid along the exterior surface of an irrigated ablation electrode. In this embodiment, an irrigated electrode is made of platinum with a shell structure having a flat bottom and a cylindrical side with a uniform wall thickness. In some embodiments, the ablation electrode has an outer diameter of 8 French (2.66 mm), a length of 0.197 inches (5.00 mm) and a wall thickness of 0.010 inches (0.254 mm). In some embodiments, twenty-seven (27) rectangular apertures are machined into the shell, each 0.0005 inches (0.0123 mm) high by 0.020 inches (0.508 mm) width, yielding an aspect ratio of forty (40). In some embodiments, in operation, a fluid, for example saline, fills the interior of an ablation electrode in contact with the inside surface of the shell. In some embodiments, the fluid passes from the interior space to its exterior surface through each aperture. At an overall flow rate of 5 ml/min of saline at 20° C., each hole has a volumetric flow of 0.00308 cm$^3$/sec resulting in a pressure drop estimated to be at least about 1.00 psi (6,895 pascals). Because of the high pressure drop through each aperture, flow through each aperture is generally identical.

In another embodiment, apertures with a rectangular cross section or slots are used in conjunction with an insert placed in the interior space of a shell similar to that shown in FIGS. 10A and 10B. Both the apertures and fluid passageways provide a means to distribute fluid along the exterior surface of an irrigated ablation electrode. In this embodiment, an irrigated electrode is made of platinum with a shell structure having a flat bottom and a cylindrical side with a uniform wall thickness. In some embodiments, the ablation electrode has an outer diameter of 8 Fr (2.66 mm), a length of 0.197 inches (5.00 mm) and a wall thickness of 0.004 inches (0.102 mm). Twenty-seven (27) rectangular apertures are machined into the shell, each 0.0005 inches (0.127 mm) high by 0.020 inches (0.508 mm) width, yielding an aspect ratio of forty (40). In some embodiments, an insert is made of PEEK with an outer diameter of 0.085 inches (2.159 mm) and an inner diameter of 0.025 inches (0.635 mm) and circular fluid passageways with a diameter of 0.003 inches (0.0762 mm). This yields a fluid gap between the interior surface of the ablation electrode and the outer surface of the insert of 0.005 inches (0.127 mm). In some embodiments, a fluid, for example saline, fills the center and the proximal space contiguous with the insert and passes into the gap between the insert exterior and shell interior surfaces. Fluid also passes from the interior of the insert through the fluid passageways through an aperture to the exterior surface of an electrode. At an overall flow rate of 5 ml/min of saline at 20° C., each fluid passageway and aperture has a volumetric flow of 0.00308 cm$^3$/sec resulting in an estimated pressure drop of about 0.415 psi (292 pascals) through the fluid passageway and about 1.00 psi (6,895 pascals) through the aperture yielding a total pressure drop from the interior to exterior surface of about 1.452 psi (10,011 pascals). Because of this high pressure drop, flow through each aperture is generally identical.

The present invention describes a system for delivering pressures pulses to fluid channels within an ablation electrode to provide a hydraulic force for removing obstructions in one or more apertures and to dislodge incipient thrombus formations in the vicinity of an ablation electrode before they become clinically dangerous. Historically, irrigated ablation electrodes used overall fluid flow rates ranging from about 15 to 30 ml/min to maintain clear fluid passages and prevent thrombus formation on an ablation electrode exterior surface or on tissue in contact or in the vicinity of an ablation electrode. Currently, conventional fluid-flow rates typically range from about 8-15 ml/min. Despite this reduction, fluid overload in patients undergoing cardiac ablations using irrigated ablation electrodes remains a clinical issue for most procedures. It is not uncommon for ablation times for treatment of atrial fibrillation to exceed 120 minutes. At the lowest flow rates, a liter of fluid is injected into a patient, and even more at higher flow rates. Even for a healthy patient, medical intervention is generally necessary to reestablish fluid equilibrium sometimes requiring an extended hospital stay to return to normal levels. Reducing flow rates through an irrigated ablation electrode increases the risk of thrombus formation to an unacceptable level. Some embodiments of the present invention include a method of effecting pressure pulses in a fluid path supplying an ablation electrode to provide a brief increase in hydraulic pressure to disrupt obstructions or thrombus formations before they become clinically dangerous.

In some embodiments, the present invention uses the ability of water to transmit a pressure wave of pulse over a fluid path connecting the ablation electrode to a fluid pump assembly. From a theoretical perspective, an induced pressure wave will travel at a speed of 4721 ft/sec (1438 msec) in water. Kinetic energy induced by the pressure pulse will be absorbed by elastic expansion of material containing the water and by frictional losses and reflection of the wave at the ends of the fluid channel. Since the materials containing the fluid are somewhat rigid and the path length short relative to the speed of travel, pressure pulses can be transmitted rapidly from one end of the fluid pathway to the other. For a one-meter (1-m) path, the pulse will take less than a millisecond to travel the entire length of the fluid channel. A common phenomenon which illustrates this principle is water hammer in fluid pumping systems. Sudden closure of an open valve in a water pipe can lead to 'water hammer' which is essentially a pressure wave rapidly travelling through the pipes and being reflected at bends and closed valves. The rapid and sometimes violent response is indicative of the force that can be applied via pressure waves within closed fluid filled spaces.

Figure 24:
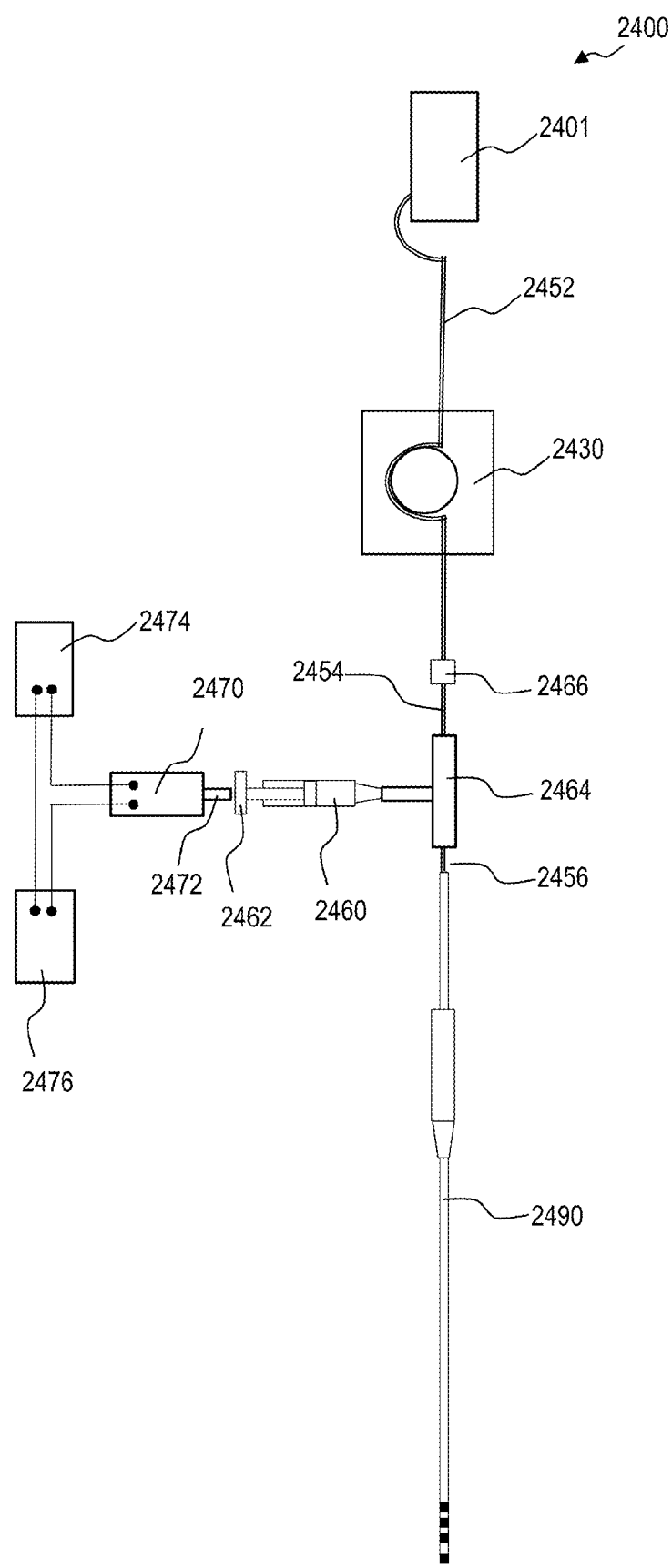
FIG. 24 is a diagram of a system 2400 for delivering pressure pulses to fluid within a catheter with the irrigated ablation electrode.

FIG. 24 shows a system for creating pressure pulses within a fluid loop used to supply fluid to an irrigated ablation electrode. Pump assembly 2430 is operably coupled to fluid reservoir 2440 and check valve 2466 by tubing 2452. 2466 is operably coupled to T-assembly 2464 by fluid tubing 2454. In some embodiments, fluid tubing 2464 is operably couple to ablation catheter 2490 by fluid tubing 2456. Syringe body 2460 is operably coupled to T-Assembly 2464 and syringe plunger 2462. Syringe plunger 2462 is mechanically activated by plunger 2472 of solenoid 2470. In some embodiments, solenoid 2470 is electrically connected to power supply 2476 and timer 2474.

In operation, syringe 2460 is filled with the same fluid as the irrigation fluid ablation catheter 2490. Solenoid 2470 is electrically energized extending plunger 2472 toward syringe plunger 2462 thereby pushing fluid from syringe 2560 into T-Assembly 2464 and thereafter into fluid tubing 2556. One way check valve 2466 directs flow towards ablation catheter 2490 and prevents backflow in the direction of fluid pump 2430. Because liquid is essentially incompressible, pressure is increased in syringe body 2560 which is then transmitted to fluid passageways connecting the ablation catheter to the syringe pump. Solenoid 2570 is then de-energized, allowing plunger 2572 to retract and allowing the pressure in syringe body 2560 to return to systemic pressure of the fluid passageway at T-Assembly 2464. The effect is a temporary increase in pressure throughout the catheter fluid system which also increases the hydraulic forces at the exit of each aperture in an ablation electrode. The amplitude of the pressure spike depends on the length of travel of syringe plunger and the speed with which force is applied to the plunger 2462.

Plunger 2462 is mechanically pushed by solenoid actuator 2472. Solenoid 2470 is activated by applying voltage to its coils using power source 2476 which is controlled by timer 2474. In operation, timer 2474 closes a relay which the powers solenoid 2470. The timer controls the duration of a pulse $t_c$, and the interval between pulses $t_r$.

Figure 25:
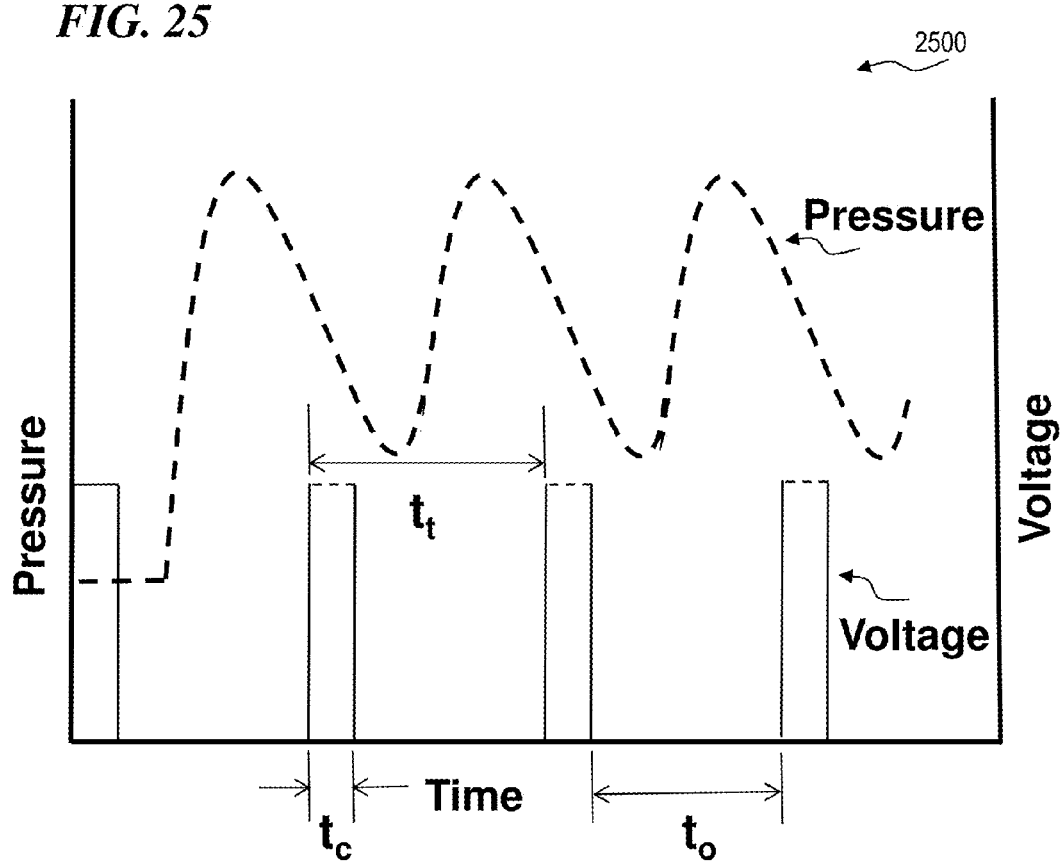
FIG. 25 is a graph 2500 of actuator energization and of fluid pressure with time.

FIG. 25 is a graph 2500 that shows a graphical representation of a transient pressure wave created by energizing solenoid 2570 with a pulse repetition rate at a time interval $t_r$ for a pulse duration period of time $t_c$. The voltage trace is shown by a solid line and the fluid pressure trace by a dashed line. The pressure response lags the voltage trace because of the response time of the system. In operation of some embodiments, the time $t_r$ is in a range of 0.001 to 30 seconds, but preferably is in a range of 0.1 to 5 seconds, inclusive.

In some embodiments, other methods are used to push the plunger such as hydraulic cylinders actuated by air pressure or an eccentric disk rotating at a fixed speed. In some embodiments, the pulsing is controlled by a microprocessor or by circuits within an RF ablation generator. In some embodiments, repetitive pulses are applied to the system for the entirety of an ablation procedure. In some embodiments pulses are applied based on a value of an ablation parameter such as electrode tip temperature or contact force exerted by an ablation electrode.

Figure 26:
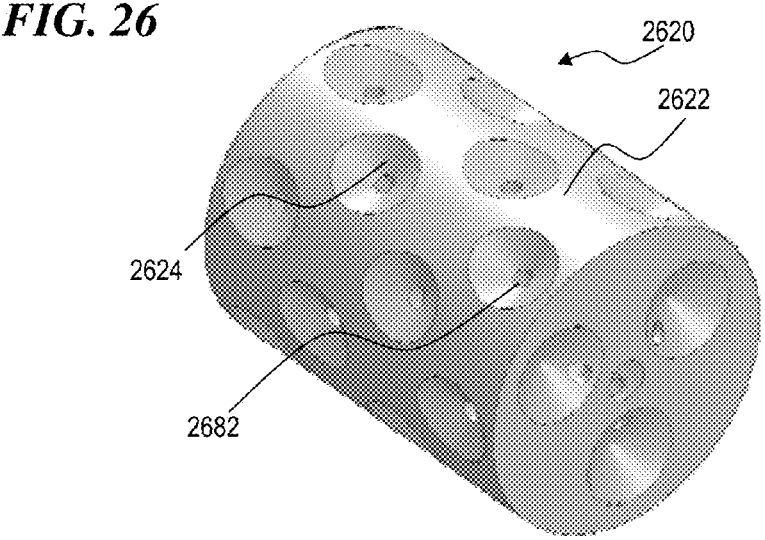
FIG. 26 is an isometric view of an insert 2620 with internal fluid passageways in which the passageways have a changing diameter wherein the diameter expands near the external surface of the insert, according to some embodiments of the present invention.

FIG. 26 is an isometric view of an insert 2600 with internal passageways 2682 in which each passageway 2682 has an expanded diameter (i.e., countersunk depression 2624) at the external surface of the insert 2600, according to some embodiments of the present invention. In some embodiments, each passageway 2682 is drilled through insert material 2622 using a small-diameter drill bit or otherwise formed, and each countersunk depression 2624 is drilled or machined using a suitably shaped bit to align with its corresponding passageway 2682. The countersunk depressions 2624 are used in conjunction with slit-shaped apertures, and provide at least two advantages: delivery of fluid across most or all of the slot length, and a reduced requirement to accurately align the shell and its slit apertures to the passageways 2682 of the insert 2600.

FIGS. 27A and 27B are a cross-sectional views of alternate embodiments of an ablation electrode according to some embodiments of the present invention. FIG. 27A is a cross-sectional view along a longitudinal axis of irrigated ablation electrode 2701 which contains insert 2722 contained within shell 2710. Insert 2722 contains circular fluid passageways 2782 whose diameter is larger than the largest dimension of aperture 2708. A fluid passageway which is larger than the mating aperture allows the insert passageways and apertures to be processed separately and the parts assembled after fabrication potentially reducing manufacturing costs. FIG. 27B shows ablation electrode 2702 with insert 2722 in which a porous material insert 2722 with porous material 2788 inserted within fluid passageway 2782 such that the outside surfaces of 2788 are in substantial contact with the inside surface of passageway 2782. The use of a porous material with an open cell porosity allows fluid to pass therethrough and also serves as a filter for particulate contained in the fluid to remove particles of sufficient size thus preventing partial or complete blockage of an aperture 2708.

In some embodiments, the present invention provides an ablation electrode with a plurality of the following features:
a. outer shell made of a metal with a uniform wall thickness in which the shell wall thickness divided by the shell cylindrical radius is significantly less than 1;
b. fluid in contact with the interior surfaces of an ablation electrode shell in which the inside surface area of the ablation electrode shell in contact with fluid divided by the total inside surface area of the shell is greater than 0.50;
c. in some embodiments, the layer of fluid in contact with the inside surface of an ablation electrode shell in which the radial thickness of the fluid layer divided by the outer cylindrical radius of the ablation electrode shell is less than 0.5;
d. in some embodiments, a portion of the outer surface of the insert in contact with the inside surface of an ablation electrode shell at discrete locations such that the ratio of surface contact area of the insert to total inside surface area of the shell is less than 0.5;
e. In some embodiments, the insert contains one or more grooves on its exterior surface for the purpose of maintaining a fluid layer in contact with the interior surface of an ablation electrode shell in which the ablation electrode shell forms at least one boundary for one or more fluid channels;
f. in some embodiments, the ratio of the wall thickness of the insert to the outer radius of the insert is less than 0.75;
g. in some embodiments, the insert has fluid channels along the insert external surfaces or through the insert internal mass for the purpose of directing fluid to holes located in the outer shell;
h. in some embodiments, the insert has fluid channels in which at least one of the channels has an combined length divided by hydraulic diameter greater than 5; and
i. in some embodiments, the insert has a connecting member for joining an ablation catheter electrode to a catheter shaft which contains an annular fluid channel in which width of the fluid channel divided by the radius of the connecting member is less than 0.50.

In some embodiments, the present invention provides an ablation electrode in which the weight of the tip divided by the weight of another tip having the same external dimensions but made entirely of the same material as the outer shell of the tip is less than 0.50.

In some embodiments, the present invention provides an ablation electrode in which the time to decrease a step change in temperature to 1/e of the initial temperature difference divided the time to decrease a step change in 1/e of the initial temperature difference of a tip made entirely of the same metal as the ablation electrode shell is less than 0.50.

In some embodiments, the present invention provides an ablation electrode shell with holes for passage of fluid from a location within the electrode to external surfaces of the electrode shell for purposes of cooling the outside surfaces of the electrode shell.

In some embodiments, the present invention provides an ablation electrode insert made of a porous material in which the external surface of the porous medium is in contact with the interior surface of an ablation electrode shell for the purpose of providing a fluid layer in contact with the interior surface of the shell and for supplying fluid to holes for the purpose of cooling the external surface of an ablation electrode shell.

In some embodiments, the present invention provides a method for using an ablation electrode that includes one or more of the following:
a. placing fluid in contact with the interior surfaces of an electrode shell to maintain a shell surface temperature below that required for formation of coagulum;
b. using fluid channels within an ablation electrode to direct flow to each opening in an ablation electrode shell to insure uniform distribution of fluid to each opening over a range of fluid flow operating conditions;

c. using fluid channels within an ablation electrode with sufficient pressure drop to maintain each opening in an ablation electrode shell free of debris and temporary flow restrictions over a range of fluid flow operating conditions;
d. providing uniform distribution of fluid over the exterior surface of an electrode at flow rates lower than present ablation irrigated electrodes without formation of coagulum on the exterior surfaces of an electrode;
e. varying coolant flow rate to an ablation electrode to change the ablation electrode temperature from 30 to 85° C. at a fixed power setting;
f. choosing electrode materials of lower density to increase electrode thermal responsiveness by decreasing overall electrode mass and heat capacity;
g. performing cardiac ablations by selecting a delivered power and electrode operating temperature and adjusting fluid flow rate through the electrode to achieve the selected electrode operating temperature while simultaneously minimizing blood coagulation and collateral tissue damage;
h. performing cardiac ablations using an electrode with low thermal capacitance to more rapidly sense aberrations or anomalies in tissue heating and consequently alter ablation conditions to minimize collateral damage to tissue such as perforations or lacerations cause by steam formation within tissue and reduce coagulum formation;
i. using aperture shape and/or aspect ratio for apertures in the shell of an ablation electrode to provide a sufficient pressure drop to maintain each opening in an ablation electrode shell free of debris and temporary flow restrictions over a range of fluid flow operating conditions;
j. maintaining a pressure drop of at least 0.05 psi (345 pascals) between irrigation fluid inside the irrigated ablation electrode and fluid immediately outside the electrode when the irrigation fluid has a flow rate of no more than five milliliters per minute (5 ml/min); and/or
k maintaining a pressure drop of at least 0.1 psi (689 pascals) between irrigation fluid inside the irrigated ablation electrode and fluid immediately outside the electrode when the irrigation fluid has a flow rate of no more than five milliliters per minute (5 ml/min).

In some embodiments, the present invention provides an apparatus that includes an ablation electrode including an ablation electrode shell having an interior surface with a total inside surface area, the shell having a wall thickness, wherein the ablation electrode shell has holes for passage of fluid from a location within the ablation electrode to external surfaces of the ablation electrode shell for purposes of cooling the outside surfaces of the electrode shell; and an insert made of a porous material in which the external surface of the porous medium is in contact with the interior surface of an ablation electrode shell for the purpose of providing a fluid layer in contact with the interior surface of the shell and for supplying fluid to holes for the purpose of cooling the external surface of an ablation electrode shell.

In some embodiments, the present invention provides a method that includes: providing an ablation catheter tip; and placing fluid in contact with the interior surfaces of an electrode shell of the ablation catheter tip to maintain a shell surface temperature below that required for formation of coagulum.

In some embodiments, the present invention provides a method that includes: providing an ablation catheter tip; and using fluid channels within the ablation electrode tip to direct flow to each one of a plurality of openings in an ablation electrode shell of the ablation catheter tip to insure uniform distribution of fluid to each opening over a range of fluid flow operating conditions.

In some embodiments, the present invention provides a method that includes: providing an ablation catheter tip; and using fluid channels within the ablation catheter tip with sufficient pressure drop to maintain each one of a plurality of openings in an ablation electrode shell of the ablation catheter tip free of debris and temporary flow restrictions over a range of fluid flow operating conditions.

In some embodiments, the present invention provides a method that includes: providing an ablation catheter tip; and providing uniform distribution of fluid over the exterior surface of an electrode of the ablation catheter tip at flow rates lower than conventional ablation irrigated electrodes without formation of coagulum on the exterior surfaces of the electrode.

In some embodiments, the present invention provides a method that includes: providing an ablation catheter tip; and varying coolant flow rate to an ablation electrode to change the ablation electrode temperature in a range of 30 to 85 degrees C., inclusive, at a fixed RF power setting.

In some embodiments, the present invention provides a method that includes: providing an ablation catheter tip; and choosing electrode materials of lower density for the ablation catheter tip in order to increase electrode thermal responsiveness by decreasing overall electrode mass and heat capacity.

In some embodiments, the present invention provides a method that includes: providing an ablation catheter tip; and performing cardiac ablations by selecting a delivered power and electrode operating temperature and adjusting fluid flow rate through an electrode on the ablation catheter tip in order to achieve a selected electrode operating temperature while simultaneously minimizing blood coagulation and collateral tissue damage.

In some embodiments, the present invention provides a method that includes: providing an ablation catheter tip; and performing cardiac ablations using the ablation catheter tip having an electrode with low thermal capacitance to more rapidly sense aberrations or anomalies in tissue heating and consequently alter ablation conditions to minimize collateral damage to tissue such as perforations or lacerations cause by steam formation within tissue and reduce coagulum formation.

In some embodiments, the present invention provides an apparatus that includes: an irrigated ablation electrode shell having a plurality of apertures each having an aspect ratio greater than two.

In some embodiments, the present invention provides an apparatus that includes: an irrigated electrode shell having a plurality of apertures, wherein at least one of the plurality of apertures has a hydraulic pressure drop greater than 0.10 psi (689.5 pascals) at a fluid flow rate of 5 ml/min of water at 20 degrees C.

In some embodiments, the present invention provides an irrigated ablation apparatus that includes an irrigated electrode shell having a plurality of apertures, wherein the irrigated ablation apparatus has a hydraulic pressure drop greater than 0.20 psi (1379 pascals) at a fluid flow rate of 15 ml/min of water at 20 degrees C.

In some embodiments, the present invention provides an apparatus that includes: an ablation electrode that includes: a plurality of high L/d channels and slit-shaped apertures to give a high pressure drop through the electrode to provide for more uniform flow over exterior of shell and reduce propensity for aperture blockage; and an insert and shell having reduced electrode mass to provide a more thermally responsive tip to temperature anomalies in tissue during an ablation; wherein the electrode is configured to have a thin layer of water in contact with the interior of the electrode's shell through which fluid flows to enhance shell cooling and provide a thermal capacitor for thermal hot spots in a shell.

In some embodiments, the present invention provides an apparatus that includes: an ablation electrode that includes: a plurality of high L/d channels and slit-shaped apertures to give a high pressure drop through the electrode to provide for more uniform flow over exterior of shell and reduce propensity for aperture blockage; and an insert and shell having reduced electrode mass to provide a more thermally responsive tip to temperature anomalies in tissue during an ablation; wherein the electrode is configured to have a thin layer of water in contact with the interior of the shell to enhance cooling and provide a thermal capacitor for thermal hot spots in a shell.

In some embodiments, the present invention provides an apparatus that includes: an ablation electrode that includes: a plurality of high L/d channels and slit-shaped apertures to give a high pressure drop through the electrode to provide for more uniform flow over exterior of shell and reduce propensity for aperture blockage; and an insert and shell having reduced electrode mass to provide a more thermally responsive tip to temperature anomalies in tissue during an ablation.

In some embodiments, the present invention provides an apparatus that includes: an ablation electrode that includes a plurality of high L/d channels and slit-shaped apertures to provide for more uniform distribution of fluid over an exterior surface of the electrode and reduce propensity for aperture blockage.

In some embodiments, the present invention provides an apparatus that includes an ablation electrode that has an outer metal shell with a uniform wall thickness, wherein the shell wall thickness divided by the shell cylindrical radius is significantly less than 1, and wherein the electrode holds fluid in contact with more than half of an interior surface of the outer shell. In some embodiments, a ratio of an inside surface area of the interior surface of the outer shell that is in contact with fluid divided by the total inside surface area of the shell is greater than 0.50. In some embodiments, a layer of the fluid is in contact with the inside surface of the outer metal shell, and wherein a radial thickness of the fluid layer divided by the outer cylindrical radius of the ablation electrode shell is less than 0.5.

In some embodiments, the present invention provides an apparatus that includes: an ablation electrode that includes: an ablation electrode shell that has an interior surface with a total inside surface area; and an insert within the ablation electrode shell, wherein a portion of an outer surface of the insert in contact with the interior surface of the ablation electrode shell at discrete locations such that a ratio of surface contact area of the insert with the shell to the total inside surface area of the shell is less than 0.5.

In some embodiments, the present invention provides an apparatus that includes: an ablation electrode that includes: an ablation electrode shell that has an interior surface with a total inside surface area; and an insert within the ablation electrode shell, wherein one or more grooves on the exterior surface of the insert maintain a fluid layer in contact with the interior surface of an ablation electrode shell in which the ablation electrode shell forms at least one boundary for one or more fluid channels.

In some embodiments, the present invention provides an apparatus that includes: an ablation electrode that includes: an ablation electrode shell that has an interior surface with a total inside surface area, wherein the shell has a wall thickness; and an insert within the ablation electrode shell, wherein the insert has a wall thickness and an outer radius, wherein a ratio of the wall thickness of the insert to the outer radius of the insert is less than 0.75.

In some embodiments, the present invention provides an apparatus that includes: an ablation electrode that has an ablation electrode shell that has an interior surface with a total inside surface area, wherein the shell has a wall thickness; and an insert within the ablation electrode shell, wherein the insert has a plurality of fluid channels along the insert's external surfaces or through the insert internal mass for the purpose of directing fluid to holes located in the outer shell.

In some embodiments, the present invention provides an apparatus that includes: an ablation electrode that includes: an ablation electrode shell that has an interior surface with a total inside surface area, wherein the shell has a wall thickness; and an insert within the ablation electrode shell, wherein the insert has a plurality of fluid channels, and wherein at least one of the plurality of fluid channels has an combined length divided by hydraulic diameter greater than 5.

In some embodiments, the present invention provides an apparatus that includes: an ablation electrode that includes: an ablation electrode shell that has an interior surface with a total inside surface area, wherein the shell has a wall thickness; and an insert within the ablation electrode shell, wherein the insert has a connection member that joins the ablation catheter electrode to a catheter shaft, wherein the connection member has a radius, wherein the catheter shaft has an annular fluid channel that has a width, and wherein the width of the fluid channel divided by the radius of the connection member is less than 0.50.

In some embodiments, the present invention provides an apparatus that includes an ablation electrode that has a tip, wherein the tip has a weight, wherein the tip has an outer shell made of a first material, wherein the tip has an interior structure made of a second material and wherein the weight of the tip divided by the weight of a tip made entirely of the first material as the outer shell is less than 0.50.

In some embodiments, the present invention provides an apparatus that includes an ablation electrode that has a tip, wherein the tip has a weight, wherein the tip has an outer shell made of a first material that has a first density, wherein the tip has an interior structure made of a second material that has a second density, and wherein the density of the second material divided by the density of the first material is less than 0.50.

In some embodiments, the present invention provides an apparatus that includes an ablation electrode, wherein a time period needed to decrease a step change in temperature to 1/e of the initial temperature difference divided the time to decrease a step change in 1/e of the initial temperature difference of a tip made entirely of the same metal as the ablation electrode shell is less than 0.50, wherein a natural logarithm has a base, and wherein e is the base of the natural logarithm.

In some embodiments, the present invention provides an apparatus that includes an ablation electrode that includes: an ablation electrode shell that has an interior surface with a total inside surface area, wherein the shell has a wall thickness, wherein the ablation electrode shell has holes for passage of fluid from a location within the ablation electrode to external surfaces of the ablation electrode shell to cool the outside surfaces of the electrode shell; and an insert made of a porous material in which the external surface of the porous medium is in contact with the interior surface of an ablation electrode shell to provide a fluid layer in contact with the interior surface of the shell and to supply fluid to holes to cool the external surface of an ablation electrode shell.

In some embodiments, the present invention provides a method that includes providing an ablation catheter tip; and placing fluid in contact with the interior surfaces of an electrode shell of the ablation catheter tip to maintain a shell surface temperature below that at which coagulum forms.

In some embodiments, the present invention provides a method that includes: providing an ablation catheter tip; and using fluid channels within the ablation electrode tip to direct flow to each one of a plurality of openings in an ablation electrode shell of the ablation catheter tip to insure uniform distribution of fluid to each opening over a range of fluid flow operating conditions.

In some embodiments, the present invention provides a method that includes: providing an ablation catheter tip; and using fluid channels within the ablation catheter tip with sufficient pressure drop to maintain each one of a plurality of openings in an ablation electrode shell of the ablation catheter tip free of debris and temporary flow restrictions over a range of fluid flow operating conditions.

In some embodiments, the present invention provides a method that includes: providing an ablation catheter tip; and providing uniform distribution of fluid over the exterior surface of an electrode of the ablation catheter tip at flow rates lower than conventional ablation irrigated electrodes without formation of coagulum on the exterior surfaces of the electrode.

In some embodiments, the present invention provides a method that includes: providing an ablation catheter tip; and varying coolant flow rate to an ablation electrode to change the ablation electrode temperature in a range of 30 to 85 degrees C., inclusive, at a fixed RF power setting.

In some embodiments, the present invention provides a method that includes: providing an ablation catheter tip; and choosing electrode materials of lower density for the ablation catheter tip in order to increase electrode thermal responsiveness by decreasing overall electrode mass and heat capacity.

In some embodiments, the present invention provides a method that includes: providing an ablation catheter tip; and performing cardiac ablations by selecting a delivered power and electrode operating temperature and adjusting fluid flow rate through an electrode on the ablation catheter tip in order to achieve a selected electrode operating temperature while simultaneously minimizing blood coagulation and collateral tissue damage.

In some embodiments, the present invention provides a method that includes: providing an ablation catheter tip; and performing cardiac ablations using the ablation catheter tip having an electrode with low thermal capacitance to more rapidly sense aberrations or anomalies in tissue heating and consequently alter ablation conditions to minimize collateral damage to tissue such as perforations or lacerations cause by steam formation within tissue and reduce coagulum formation.

In some embodiments, the present invention provides an apparatus that includes an irrigated ablation electrode shell having a plurality of apertures each having an aspect ratio greater than two.

In some embodiments, the present invention provides an apparatus that includes an irrigated electrode shell having a plurality of apertures, wherein at least one of the plurality of apertures has a hydraulic pressure drop greater than 0.1 psi (689.5 pascals) at a fluid flow rate of 5 ml/min of water at 20 degrees C.

In some embodiments, the present invention provides an apparatus that includes: an ablation electrode that includes: a plurality of high L/d channels and slit-shaped apertures to give a high pressure drop through the electrode to provide for more uniform flow over exterior of shell and reduce propensity for aperture blockage; and an insert and shell having reduced electrode mass to provide a more thermally responsive tip to temperature anomalies in tissue during an ablation; wherein the electrode is configured to have a thin layer of water in contact with the interior of the electrode's shell through which fluid flows to enhance shell cooling and provide a thermal capacitor for thermal hot spots in a shell.

In some embodiments, the present invention provides an apparatus that includes: an ablation electrode that includes: a plurality of high L/d channels and slit-shaped apertures to give a high pressure drop through the electrode to provide for more uniform flow over exterior of shell and reduce propensity for aperture blockage; and an insert and shell having reduced electrode mass to provide a more thermally responsive tip to temperature anomalies in tissue during an ablation; wherein the electrode is configured to have a thin layer of water in contact with the interior of the shell to enhance cooling and provide a thermal capacitor to avoid thermal hot spots in a shell.

In some embodiments, the present invention provides an apparatus that includes: an ablation electrode that includes: a plurality of high L/d channels and slit-shaped apertures to give a pressure drop of at least 0.1 psi (689 pascals) through the electrode at a flow rate of no more than 5 ml/min to provide for more uniform flow over exterior of shell and reduce propensity for aperture blockage; and an insert and shell having reduced electrode mass to provide a more thermally responsive tip to temperature anomalies in tissue during an ablation.

In some embodiments, the present invention provides an apparatus that includes an ablation electrode that includes a plurality of high L/d channels and a plurality of slit-shaped apertures to provide for more uniform distribution of fluid over an exterior surface of the electrode and reduce propensity for aperture blockage. In some embodiments, the present invention provides an irrigated ablation electrode shell which contains at least two or more apertures with an aspect ratio (a ratio of length to width) that is as least 2.5.

In some embodiments, the present invention provides an irrigated ablation electrode tip that has an electrode shell with a plurality of distinct (i.e., non-continuous) apertures, such that the electrode tip has a hydraulic pressure drop greater than 0.1 psi (689 pascals) (as measured between the pressure of fluid as it enters the tip and the pressure of fluid immediately outside the electrode shell) at a fluid flow rate of 5 ml/min (milliliters per minute) of water at 20 degrees C. In some embodiments, the method further includes using aperture shape and/or aspect ratio for apertures in the shell of an ablation electrode to provide a sufficient pressure drop to maintain each opening in an ablation electrode shell free of debris and temporary flow restrictions over a range of fluid flow operating conditions.

In some embodiments, the method further includes maintaining a pressure drop of at least 0.05 psi (345 pascals) between irrigation fluid inside the irrigated ablation electrode and fluid immediately outside the electrode when the irrigation fluid has a flow rate of no more than five milliliters per minute (5 ml/min). In some embodiments, the method includes maintaining a pressure drop of at least 0.1 psi (689 pascals) at a flow rate of no more than five milliliters per minute.

In some embodiments, the present invention provides an apparatus that includes an elongate catheter body that has a longitudinal axis; an electrode shell that has a metal outer surface and has a first plurality of slits formed through the electrode shell, wherein the electrode shell is coupled to and located at a distal end portion of the elongate catheter body, and wherein each one of the first plurality of slits has a maximum dimension along the slit's length that is more than twice as long as a maximum dimension across the slit's width; an electrical conductor that extends through the elongate catheter body and that is electrically coupled to the electrode shell; and an irrigation lumen that extends through elongate catheter body and that is fluidly coupled to the plurality of slits. In some embodiments, the cup-shaped electrode shell has a cylindrical outer side-wall surface and a domed end-wall surface. Some embodiments further include an insert having a heat capacity no larger than 20% of the heat capacity of water.

In some embodiments, a pressure drop across each one of the first plurality of holes is at least 0.5 psi when 5 ml/minute of irrigation fluid collectively flows through the first plurality of holes. In some embodiments, the insert is characterized by a volume, and the volume of the insert is at least 30% of the total inner volume of the electrode shell. In some embodiments, the outer surface of the insert has a plurality of recesses extending laterally from an outer end of each of the first plurality of holes. In some embodiments, each respective one of the first plurality of slits is straight as viewed from a vector normal to the outer surface of the electrode shell next to the respective slit. In some embodiments, a line extending centrally along the length of each of the first plurality of slits is parallel to the longitudinal axis of elongate catheter body at the distal end. In some embodiments, a line extending centrally along the length of each of the first plurality of slits follows a helical path around the longitudinal axis of the elongate catheter body at the distal end. In some embodiments, a line extending centrally along the length of each of the first plurality of slits follows a circular path around and perpendicular to the longitudinal axis of elongate catheter body at the distal end.

In some embodiments, the present invention provides a method that includes: providing an elongate catheter body having an electrical conductor and an irrigation lumen that both extend through the elongate catheter body; providing an electrode shell that has a metal outer surface; forming a first plurality of slits the electrode shell, wherein each one of the first plurality of slits has a maximum dimension along a length of the slit that is more than twice as long as a maximum dimension across a width of the slit; mechanically coupling the electrode shell to a distal end portion of the elongate catheter body; electrically coupling the electrical conductor to the electrode shell; and fluidly coupling the irrigation lumen to the plurality of slits.

In some embodiments, the present invention provides an apparatus that includes: an electrode shell that has a metal outer surface; an elongate catheter body having an electrical conductor and an irrigation lumen that both extend through the elongate catheter body; means for forming a first plurality of slits the electrode shell, wherein each one of the first plurality of slits has a maximum dimension along a length of the slit that is more than twice as long as a maximum dimension across a width of the slit; means for mechanically coupling the electrode shell to a distal end portion of the elongate catheter body; means for electrically coupling the electrical conductor to the electrode shell; and means for fluidly coupling the irrigation lumen to the plurality of slits.

In some embodiments, the present invention provides an apparatus that includes: an elongate catheter body that has a longitudinal axis; a generally cup-shaped thin electrode shell that has a metal outer surface, an inner surface that has an area and that surrounds a total inner volume of the electrode shell, and a first plurality of holes formed through the electrode shell from the inner surface to the outer surface, wherein the electrode shell is mechanically coupled to and located at a distal end portion of the elongate catheter body, and wherein a thickness of the thin electrode shell is no more than 10% of a maximum outer diameter of the electrode shell; an insert that has an outer surface with a shape and size that substantially matches the inner surface of the electrode shell, wherein the outer surface of the insert is in contact with at least 70% of the inner surface of the electrode shell, and wherein the insert has a heat capacity that is no more than 30% of that of water; an electrical conductor that extends through the elongate catheter body and that is electrically coupled to the electrode shell; and an irrigation lumen that extends through elongate catheter body and that is fluidly coupled to the plurality of holes.

In some embodiments, the cup-shaped electrode shell has a cylindrical outer side-wall surface. In some embodiments, the cup-shaped electrode shell has a domed end-wall surface. In some embodiments, each one of the first plurality of holes are slit shaped. In some embodiments, a pressure drop across each one of the first plurality of holes is at least 0.5 psi when 5 ml/minute of irrigation fluid collectively flows through the first plurality of holes. In some embodiments, the insert is characterized by a volume, and the volume of the insert is at least 30% of the total inner volume of the electrode shell. In some embodiments, the outer surface of the insert has a plurality of recesses extending laterally from an outer end of each of the first plurality of holes.

In some embodiments, the present invention provides a method that includes: providing an elongate catheter body having an electrical conductor and an irrigation lumen that both extend through the elongate catheter body; providing an electrode shell that has a metal outer surface; forming a first plurality of slits the electrode shell, wherein each one of the first plurality of slits has a maximum dimension along a length of the slit that is more than twice as long as a maximum dimension across a width of the slit; mechanically coupling the electrode shell to a distal end portion of the elongate catheter body; electrically coupling the electrical conductor to the electrode shell; and fluidly coupling the irrigation lumen to the plurality of slits.

In some embodiments, the present invention provides an apparatus that includes: an electrode shell that has a metal outer surface; an elongate catheter body having an electrical conductor and an irrigation lumen that both extend through the elongate catheter body; means for forming a first plurality of slits the electrode shell, wherein each one of the first plurality of slits has a maximum dimension along a length of the slit that is more than twice as long as a maximum dimension across a width of the slit; means for mechanically coupling the electrode shell to a distal end portion of the elongate catheter body; means for electrically coupling the electrical conductor to the electrode shell; and means for fluidly coupling the irrigation lumen to the plurality of slits.

In some embodiments, the present invention provides an apparatus that includes: an elongate catheter body that has a longitudinal axis; a generally cup-shaped thin electrode shell that has a metal outer surface, an inner surface that has an area and that surrounds a total inner volume of the thin electrode shell, and a first plurality of holes formed through the thin electrode shell from the inner surface to the outer surface, wherein the thin electrode shell is mechanically coupled to and located at a distal end portion of the elongate catheter body, and wherein a thickness of the thin electrode shell is no more than 10% of a maximum outer diameter of the electrode shell; an insert that has an outer surface with a plurality of protuberances each with an end that has a shape and size that substantially matches the inner surface of the electrode shell and each having a lumen for flowing irrigation fluid that extends to a corresponding one of the first plurality of holes, wherein at least a portion of the outer surface of the insert other than the ends of the plurality of protuberances is not in contact with the inner surface of the electrode shell, and forms a space that holds a substantially non-flowing layer of irrigation fluid that is in contact with the inner surface of the electrode shell; an electrical conductor that extends through the elongate catheter body and that is electrically coupled to the electrode shell; and an irrigation lumen that extends through elongate catheter body and that is fluidly coupled to the plurality of holes. In some embodiments, the cup-shaped electrode shell has a cylindrical outer side-wall surface. In some embodiments, the cup-shaped electrode shell has a domed end-wall surface. In some embodiments, each one of the first plurality of holes are slit shaped. In some embodiments, a pressure drop across each one of the first plurality of holes is at least 0.5 psi when 5 ml/minute of irrigation fluid collectively flows through the first plurality of holes. In some embodiments, the insert is characterized by a volume, and the volume of the insert is at least 30% of the total inner volume of the electrode shell. In some embodiments, the outer surface of the insert has a plurality of recesses extending laterally from an outer end of each of the first plurality of holes.

In some embodiments, the present invention provides a method that includes: providing an elongate catheter body having an electrical conductor and an irrigation lumen that both extend through the elongate catheter body; providing an electrode shell that has a metal outer surface; forming a first plurality of slits the electrode shell, wherein each one of the first plurality of slits has a maximum dimension along a length of the slit that is more than twice as long as a maximum dimension across a width of the slit; mechanically coupling the electrode shell to a distal end portion of the elongate catheter body; electrically coupling the electrical conductor to the electrode shell; and fluidly coupling the irrigation lumen to the plurality of slits.

In some embodiments, the present invention provides an apparatus that includes: an electrode shell that has a metal outer surface; an elongate catheter body having an electrical conductor and an irrigation lumen that both extend through the elongate catheter body; means for forming a first plurality of slits the electrode shell, wherein each one of the first plurality of slits has a maximum dimension along a length of the slit that is more than twice as long as a maximum dimension across a width of the slit; means for mechanically coupling the electrode shell to a distal end portion of the elongate catheter body; means for electrically coupling the electrical conductor to the electrode shell; and means for fluidly coupling the irrigation lumen to the plurality of slits.

In some embodiments, the present invention provides an apparatus that includes: an elongate catheter body that has a longitudinal axis; a generally cup-shaped thin electrode shell that has a metal outer surface, an inner surface that has an area and that surrounds a total inner volume of the electrode shell, and a first plurality of holes formed through the thin electrode shell from the inner surface to the outer surface, wherein the thin electrode shell is mechanically coupled to and located at a distal end portion of the elongate catheter body, and wherein a thickness of the thin electrode shell is no more than 10% of a maximum outer diameter of the electrode shell; an insert that has an outer surface with a plurality of protuberances that define one or more spaces that extend to each one of the first plurality of holes for flowing irrigation fluid to and through the holes, wherein the one or more spaces are configured to increase a velocity of the irrigation fluid along the inner surface of the electrode shell; an electrical conductor that extends through the elongate catheter body and that is electrically coupled to the electrode shell; and an irrigation lumen that extends through elongate catheter body and that is fluidly coupled to the plurality of holes. In some embodiments, the cup-shaped electrode shell has a cylindrical outer side-wall surface. In some embodiments, the cup-shaped electrode shell has a domed end-wall surface. In some embodiments, each one of the first plurality of holes are slit shaped. In some embodiments, a pressure drop across each one of the first plurality of holes is at least 0.5 psi when 5 ml/minute of irrigation fluid collectively flows through the first plurality of holes. In some embodiments, the insert is characterized by a volume, and the volume of the insert is at least 30% of the total inner volume of the electrode shell. In some embodiments, the outer surface of the insert has a plurality of recesses extending laterally from an outer end of each of the first plurality of holes.

In some embodiments, the present invention provides a method that includes: providing an elongate catheter body having an electrical conductor and an irrigation lumen that both extend through the elongate catheter body; providing an electrode shell that has a metal outer surface; forming a first plurality of slits the electrode shell, wherein each one of the first plurality of slits has a maximum dimension along a length of the slit that is more than twice as long as a maximum dimension across a width of the slit; mechanically coupling the electrode shell to a distal end portion of the elongate catheter body; electrically coupling the electrical conductor to the electrode shell; and fluidly coupling the irrigation lumen to the plurality of slits.

In some embodiments, the present invention provides an apparatus that includes: an electrode shell that has a metal outer surface; an elongate catheter body having an electrical conductor and an irrigation lumen that both extend through the elongate catheter body; means for forming a first plurality of slits the electrode shell, wherein each one of the first plurality of slits has a maximum dimension along a length of the slit that is more than twice as long as a maximum dimension across a width of the slit; means for mechanically coupling the electrode shell to a distal end portion of the elongate catheter body; means for electrically coupling the electrical conductor to the electrode shell; and means for fluidly coupling the irrigation lumen to the plurality of slits.

In some embodiments, the present invention provides an apparatus that includes: an elongate catheter body that has a longitudinal axis; a generally cup-shaped thin electrode shell that has a metal outer surface, an inner surface that has an area and that surrounds a total inner volume of the electrode shell, and a first plurality of holes formed through the thin electrode shell from the inner surface to the outer surface, wherein the thin electrode shell is mechanically coupled to and located at a distal end portion of the elongate catheter body, and wherein a thickness of the thin electrode shell is no more than 10% of a maximum outer diameter of the electrode shell; an electrical conductor that extends through the elongate catheter body and that is electrically coupled to the electrode shell; an irrigation lumen that extends through elongate catheter body and that is fluidly coupled to provide irrigation fluid to the plurality of holes; and a fluid-pressure-adjustment device that applies pressure pulses to the irrigation fluid conveyed to the electrode shell. In some embodiments, the cup-shaped electrode shell has a cylindrical outer side-wall surface. In some embodiments, the cup-shaped electrode shell has a domed end-wall surface. In some embodiments, each one of the first plurality of holes are slit shaped. In some embodiments, a pressure drop across each one of the first plurality of holes is at least 0.5 psi when 5 ml/minute of irrigation fluid collectively flows through the first plurality of holes. In some embodiments, the insert is characterized by a volume, and the volume of the insert is at least 30% of the total inner volume of the electrode shell. In some embodiments, the outer surface of the insert has a plurality of recesses extending laterally from an outer end of each of the first plurality of holes.

In some embodiments, the present invention provides a method that includes: providing an elongate catheter body having an electrical conductor and an irrigation lumen that both extend through the elongate catheter body; providing an electrode shell that has a metal outer surface; forming a first plurality of slits the electrode shell, wherein each one of the first plurality of slits has a maximum dimension along a length of the slit that is more than twice as long as a maximum dimension across a width of the slit; mechanically coupling the electrode shell to a distal end portion of the elongate catheter body; electrically coupling the electrical conductor to the electrode shell; and fluidly coupling the irrigation lumen to the plurality of slits.

In some embodiments, the present invention provides an apparatus that includes: an electrode shell that has a metal outer surface; an elongate catheter body having an electrical conductor and an irrigation lumen that both extend through the elongate catheter body; means for forming a first plurality of slits the electrode shell, wherein each one of the first plurality of slits has a maximum dimension along a length of the slit that is more than twice as long as a maximum dimension across a width of the slit; means for mechanically coupling the electrode shell to a distal end portion of the elongate catheter body; means for electrically coupling the electrical conductor to the electrode shell; and means for fluidly coupling the irrigation lumen to the plurality of slits.

In some embodiments, the present invention provides an apparatus that includes: an elongate catheter body having a longitudinal axis; an electrode shell having a first plurality of slit-shaped holes formed through the electrode shell, wherein the electrode shell is coupled to and located at a distal end portion of the elongate catheter body, and wherein each one of the first plurality of slit-shaped holes has a maximum dimension along its length that is more than twice as long as a maximum dimension across its width; a conductor extending through the elongate catheter body and electrically coupled to the electrode shell; and an irrigation channel extending through elongate catheter body and fluidly coupled to the plurality of slit-shaped holes. Some embodiments further include means for conducting electricity through the elongate catheter body. Some embodiments further include means for transferring irrigation fluid through the elongate catheter body.

In some embodiments, the present invention provides a temperature-responsive irrigated ablation electrode with reduced coolant flow. Some such embodiments include a tip electrode shell with slits only such as shown in FIGS. 20-24. Some embodiments further include a shell in the form of a cup with cylindrical walls and an integral flat bottom disc with apertures in the form of slits residing in the planar surfaces of the shell and traversing through the shell wall thickness. The slits are defined by a geometric shape with two axes: a long axis and a short axis. The geometric shape has an aspect ratio defined as the maximum length along the shape long axis, L, divided by the maximum length along the shape short axis, W. For this concept, this ratio is at least 3.0. The inside of the shell is filled with water which exits the interior space of the shell to its exterior surface through the slits. Water cools the inside surface of the shell, bathes/cools the outside surface of the shell and bathes/cools tissue in contact with the shell. The use of slits increases the hydraulic pressure drop thru the apertures and is designed to give a pressure drop greater than 0.5 psi, which is greater than current practice. The use of a higher pressure drop through the slits accomplishes the following results: produces a more uniform flow through each slit so that the maximum flow rate though any aperture vs. the lowest flow rate through any aperture is minimized, minimizes the effect of tip contact with tissue on uniformity of flow through each aperture and reduces the blockage of apertures by blood, coagulated blood and/or desiccated tissue by creating a sufficiently high hydraulic pressure to prevent particle engagement entrapment within an aperture. Some embodiments further include a thin shell, a pressure drop across slit greater than 0.5 psi at 5.0 ml/min of total flow through all apertures, various patterns of slits, various geometric shapes of slits, and tip material.

In some embodiments, the present invention provides a tip electrode shell with an insert and minimal fluid contact on shell inner surface, as shown in FIGS. 10-12. Some such embodiments include a thin, uniform outer shell in the form of a cup with cylindrical walls and an integral flat bottom disc with apertures which reside in the planar surfaces of the shell and traverse the shell wall thickness. The inside volume of the shell contains a cylindrically shaped insert which minimizes contact between fluid passing there through and the interior surface of the shell. The insert is preferably made of a low-density material and has internal flow passages to direct fluid to each aperture in the shell for passage through each aperture to the outside surface of the shell. A thin/uniform shell is defined as the cup consisting of a cylindrical shell and integral bottom disc in which the ratio of the shell wall thickness, defined as the outer diameter minus the inner diameter divided by two, at any point along the cup divided by the shell outer diameter is less than 0.20. The outer surface of the insert shall be in contact with the inner surface of the shell cup over at least 75% of the surface area of the inner shell cup. Major Characteristics of this embodiment include an ablation tip that includes an outer shell in the shape of a metal cup with a cylindrical surface and integral bottom disc in which the ratio of the wall thickness of the shell at any point along the shell outer surface divided by the average diameter of the cylindrical shell is less than 0.20; apertures in the planar surfaces of the outer shell which traverse the wall thickness; and a cylindrical insert in contact with the inner surface of the shell over at least 75% of the internal surface area of the shell cup. Some embodiments further include an insert made of low-density material, an insert that includes at least 30% of total volume of tip, individual internal passageways connecting each aperture to fluid, an insert with individual recesses in its outer surface to accommodate alignment of internal fluid passageways and apertures in shell, a pressure drop across slit greater than 0.5 psi at 5.0 ml/min collectively through the passageway/aperture; and/or thin shell material.

In some embodiments, the present invention provides a shell with insert and passive water cooling of inner surface such as shown in FIGS. 8, 9, and 16. Some such embodiments include a thin, uniform outer shell in the form of a cup with cylindrical walls and an integral flat bottom disc with apertures which reside in the planar surfaces of the shell and traverse the shell wall thickness. The inside volume of the shell contains a cylindrically shaped insert which contains protuberances from its outer surfaces in which the outer surface of the raised protuberances contact the inner wall of the outer shell. When the insert is placed in the interior of the shell, a space is created between the inside surface of the shell and outer surface of the insert without protuberances, a space whose thickness is the height of the protuberance above the outside surface of the insert. Each protuberance in the insert is aligned with an aperture in the shell and passageway in the insert connects the inner lumen of the insert with the outer surface of the shell. The insert is made of a low-density material and/or has hollow cavities or forms hollow cavities when inserted into the shell. A thin and uniform shell is defined as the cup consisting of a cylindrical shell and integral bottom plate in which the ratio of the shell wall thickness, defined as the outer diameter minus the inner diameter divided by two, at any point along the cup divided by the outer diameter is less than 0.20. The inner surface of the shell in contact with fluid is greater than 50% of its total surface area and the space between the inner surface of the shell and outer surface of the insert shall not be in direct fluid communication with flowing fluid within the insert. Major characteristics of this embodiment include an ablation tip comprising an outer shell consisting of a metal cup with a cylindrical surface and integral bottom disc in which the ratio of the wall thickness of the shell at any point along the cup divided by the average diameter of the cylindrical shell is less than 0.20; apertures in the planar surfaces of the outer shell which traverse the wall thickness; and an insert in contact with the inner surface of the shell cup which holds a fluid layer in contact with the inside surface area of the shell such that the fluid layer is not in direct contact with flowing fluid. Some embodiments further include the inner surface of the shell in contact with fluid is greater than 50% of its total surface area, volume of water in contact with the inner shell surface is less than 20% of the total volume of the shell tip, insert of low-density material, an insert which comprises at least 33% of total volume of tip, individual internal passageways connecting each aperture to fluid, a pressure drop across slit greater than 0.5 psi at 5.0 ml/min collectively through all each passageway/aperture, a pattern of protuberances, variability of passageway diameters, and/or thin shell material.

In some embodiments, the present invention provides a shell with insert and active cooling of shell inner surface such as shown in FIGS. 3 thru 7, and 17. Some such embodiments include a thin, uniform outer shell in the form of a cup with cylindrical walls and an integral flat bottom disc with apertures which reside in the planar surfaces of the shell and traverse the shell wall thickness. The inside surface of the shell is cooled by fluid flowing in direct contact with an interior/internal surface of the shell or in indirect contact through an intermediate material with a conductivity of a metal in contact with the shell metal. The velocity of fluid in direct contact with the inner surfaces of the shell is at least two times greater than the average velocity of the fluid calculated using the inside cross sectional area of shell. Apertures within the shell wall are in fluid communication with at least one of the fluid passages within the shell which contain flowing fluid. A thin and uniform shell is defined as the cup consisting of a cylindrical shell and integral bottom plate in which the ratio of the shell wall thickness, defined as the outer diameter minus the inner diameter divided by two, at any point along the cup divided by the outer diameter is less than 0.20. Major characteristics of this embodiment include an ablation tip comprising an outer shell in the shape of a cup with a cylindrical surface and integral bottom disc in which the ratio of the wall thickness of the shell at any point along the cup divided by the average diameter of the cylindrical shell is less than 0.20, and apertures in the planar surfaces of the outer shell which traverse the wall thickness; fluid passageways within the shell which direct fluid to flow in direct contact with the interior surfaces of a shell or fluid passageways in the shell such that the average velocity in the passageways is at least two times greater than the average velocity calculated using the internal cross sectional area of the shell. Some embodiments further include a thin shell, a shaped insert, low-mass insert, cross-sectional geometric shape of passageways, longitudinal geometric shape of passageways, longitudinal pattern of passageways, variable cross sectional area of passageways, flow parallel or perpendicular to shell interior surface, percent of shell interior surface in contact with fluid, and a pressure drop across fluid passageways greater than 0.5 psi at 5.0 ml/min collectively through all each passageway/aperture; shell material.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
   an irrigated ablation electrode that has an outer metal shell,
   wherein the shell has a shell-wall thickness defined as an outer diameter of the shell minus an inner diameter of the shell divided by two,
   wherein a ratio of the shell-wall thickness to the shell outer diameter is less than 0.2,
   wherein the shell has a first plurality of slit apertures, wherein each of the first plurality of slit apertures has an aspect ratio of aperture length along a centerline of the aperture to maximum aperture width in a direction perpendicular to the centerline in a range from three to one thousand, inclusive, and
   wherein the first plurality of slit apertures is sized such that the maximum aperture width of each of the first plurality of slit apertures is no more than 0.0010 inches (0.0254 millimeters), in order to maintain a pressure drop value of about 0.1 psi to 25 psi between irrigation fluid inside the irrigated ablation electrode and fluid outside the electrode when the irrigation fluid has a flow rate through the first plurality of slit apertures of no more than five milliliters per minute.

2. The apparatus of claim 1, wherein the irrigated ablation electrode includes an insert, wherein the insert is constructed of one or more solid polymers, wherein the shell has an interior surface, wherein a portion of the interior surface of the shell is in contact with irrigation fluid, and wherein a ratio of a total area of the portion of the interior surface of the shell that is in contact with fluid to a total area of the interior surface of the shell is at least 0.5.

3. The apparatus of claim 2, wherein the irrigated ablation electrode has a plurality of fluid passageways that operably couple fluid to the first plurality of apertures, wherein a portion of an outer surface of the insert is in contact with the interior surface of the shell at a plurality of separated locations, and wherein a ratio of an area of the interior surface of the shell in contact with the outer surface of the insert to a total area of the interior surface of the shell is less than 0.5.

4. The apparatus of claim 2, wherein an exterior surface of the insert has a plurality of grooves, and wherein the interior surface of the shell forms at least one boundary for fluid channels formed by the plurality of grooves and the interior surface of the shell.

5. The apparatus of claim 1, wherein the irrigated ablation electrode includes an insert, wherein the insert is constructed of one or more closed-cell polymer-foam materials, wherein the insert has a central lumen surrounded by an insert wall, wherein the insert wall has a wall thickness, wherein the insert has an outer radius, and wherein a ratio of the wall thickness of the insert to the outer radius of the insert is less than 0.75.

6. The apparatus of claim 1, wherein the aspect ratio of each of the first plurality of slit apertures is in a range of five to forty, inclusive.

7. The apparatus of claim 1, wherein the aspect ratio of each of the first plurality of slit apertures is in a range of about four to about ten.

8. The apparatus of claim 1, wherein the irrigated ablation electrode includes an insert, wherein the insert has a density in a range from 5 milligrams-per-cubic-centimeter (mg/cm$^3$) to 3,000 mg/cm$^3$.

9. The apparatus of claim 1, wherein the irrigated ablation electrode further includes:
a delivery tube operatively coupled to the shell, wherein the delivery tube includes an interior fluid passageway, and
an insert, wherein the insert has a density in a range from 5 milligrams-per-cubic-centimeter (mg/cm$^3$) to 3,000 mg/cm$^3$, wherein the insert includes a central lumen through which wiring is passed, and wherein the central lumen is filled with a silicone sealant configured to seal the central lumen from fluid communication with the fluid passageway of the delivery tube.

10. A method comprising:
providing an outer metal shell of an irrigated ablation electrode, wherein the shell has a shell-wall thickness defined as an outer diameter of the shell minus an inner diameter of the shell divided by two, wherein a ratio of the shell-wall thickness to the shell outer diameter is less than 0.2;
forming a first plurality of slit apertures in the shell, wherein each of the first plurality of slit apertures has an aspect ratio of aperture length along a centerline of the aperture to maximum aperture width in a direction perpendicular to the centerline in a range from three to one thousand, inclusive, and wherein each one of the first plurality of slit apertures is sized such that the maximum aperture width of each of the first plurality of slit apertures is no more than 0.0010 inches (0.0254 millimeters), in order to maintain a pressure drop value in a range of about 0.1 psi to 25 psi between irrigation fluid inside the irrigated ablation electrode and fluid outside the electrode when the irrigation fluid has a flow rate through the first plurality of slit apertures of no more than five milliliters per minute.

11. The method of claim 10, further comprising:
providing an insert for the irrigated ablation electrode, wherein the insert is constructed of one or more solid polymers;
forming a plurality of fluid passageways in the insert for operably coupling fluid to the first plurality of apertures;
placing the insert in the shell of the irrigated ablation electrode to form an electrode tip;
using the fluid passageways within the electrode tip to force a sufficient pressure drop to maintain each one of the first plurality of slit apertures in the shell of the electrode tip free of debris and temporary flow restrictions.

12. The method of claim 11, wherein the shell includes a temperature sensor operatively coupled to the shell, the method further comprising:
forming the insert and shell with reduced thermal capacitance; and
altering ablation conditions to reduce temperature overshoot sensed by the temperature sensor.

13. The method of claim 10, further comprising:
varying irrigation-fluid-flow rate through the electrode tip to change the ablation electrode temperature in a range of 30 to 85 degrees C., inclusive, at a fixed RF power setting.

14. The method of claim 10, further comprising:
pulsing a pressure of the irrigation fluid to a pressure of at least 25% higher than otherwise maintained to clear debris from the plurality of slit apertures.

15. The method of claim 10, further comprising:
performing cardiac ablations by selecting a delivered power and electrode operating temperature and adjusting fluid flow rate through the electrode tip in order to achieve the selected electrode operating temperature.

16. An apparatus comprising:
an outer metal shell of an irrigated ablation electrode, wherein the shell has a shell-wall thickness defined as an outer diameter of the shell minus an inner diameter of the shell divided by two, wherein a ratio of the shell-wall thickness to the shell outer diameter is less than 0.2;
a first plurality of slit apertures in the shell, wherein a maximum aperture width of each of the first plurality of slit apertures is no more than 0.0010 inches (0.0254 millimeters);
an insert for the irrigated ablation electrode;
means for operably coupling fluid to the first plurality of apertures when the insert is located in the shell of the irrigated ablation electrode to form an electrode tip; and
means for, during operation of the irrigated ablation electrode, maintaining a pressure drop of about 0.1 psi to 25 psi between irrigation fluid inside the irrigated ablation electrode and fluid outside the electrode when the irrigation fluid has a flow rate of no more than five milliliters per minute.

17. The apparatus of claim 16, further comprising:
means for varying irrigation-fluid-flow rate through the electrode tip to change the ablation electrode temperature in a range of 30 to 85 degrees C., inclusive, at a fixed RF power setting.

18. The apparatus of claim 16, further comprising:
means for pulsing a pressure of the irrigation fluid to a pressure of at least 25% higher than otherwise maintained to clear debris from the plurality of slit apertures.

19. The apparatus of claim 16, further comprising:
means for forming the insert and the shell to have reduced thermal capacitance; and
means for altering ablation conditions to reduce temperature overshoot.

20. The apparatus of claim 16, wherein each of the first plurality of slit apertures has an aspect ratio of aperture length along a centerline of the aperture to the maximum aperture width in a direction perpendicular to the centerline is in a range of five to forty, inclusive.

* * * * *